US007575748B1

(12) United States Patent
Erickson et al.

(10) Patent No.: US 7,575,748 B1
(45) Date of Patent: *Aug. 18, 2009

(54) METHODS OF TREATMENT USING ANTI-ERBB ANTIBODY-MAYTANSINOID CONJUGATES

(75) Inventors: Sharon Erickson, Hillsborough, CA (US); Ralph Schwall, Pacifica, CA (US); Mark Sliwkowski, San Carlos, CA (US); Walter Blattler, Brookline, MA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/488,545

(22) Filed: Jul. 17, 2006

Related U.S. Application Data

(63) Continuation of application No. 09/811,123, filed on Mar. 16, 2001, now Pat. No. 7,097,840.

(60) Provisional application No. 60/238,327, filed on Oct. 5, 2000, provisional application No. 60/327,563, filed on Jun. 23, 2000, provisional application No. 60/189,844, filed on Mar. 16, 2000.

(51) Int. Cl.
 *A61K 39/395* (2006.01)
(52) U.S. Cl. .................................. 424/178.1; 530/387.1
(58) Field of Classification Search ........................ None
 See application file for complete search history.

(56) References Cited

U.S. PATENT DOCUMENTS

| | | | |
|---|---|---|---|
| 3,896,111 A | 7/1975 | Kupchan et al. ...... 260/239.3 T |
| 4,137,230 A | 1/1979 | Hashimoto et al. ..... 260/239.3 P |
| 4,151,042 A | 4/1979 | Higashide et al. ............. 195/96 |
| 4,248,870 A | 2/1981 | Miyashita et al. ...... 424/248.54 |
| 4,256,746 A | 3/1981 | Miyashita et al. ...... 424/248.54 |
| 4,260,608 A | 4/1981 | Miyashita et al. ...... 424/248.54 |
| 4,265,814 A | 5/1981 | Hashimoto et al. .... 260/239.3 P |
| 4,294,757 A | 10/1981 | Asai ...................... 260/239.3 P |
| 4,307,016 A | 12/1981 | Asai et al. ............. 260/239.3 P |
| 4,308,268 A | 12/1981 | Miyashita et al. ...... 424/248.54 |
| 4,308,269 A | 12/1981 | Miyashita et al. ...... 424/248.54 |
| 4,309,428 A | 1/1982 | Miyashita et al. ...... 424/248.54 |
| 4,313,946 A | 2/1982 | Powell et al. ........... 424/248.54 |
| 4,315,929 A | 2/1982 | Freedman et al. ...... 424/248.54 |
| 4,317,821 A | 3/1982 | Miyashita et al. ...... 424/248.54 |
| 4,322,348 A | 3/1982 | Asai et al. ............. 260/239.3 P |
| 4,331,598 A | 5/1982 | Hasegawa et al. ..... 260/239.3 P |
| 4,361,650 A | 11/1982 | Asai et al. ................... 435/119 |
| 4,362,663 A | 12/1982 | Kida et al. ............. 260/239.3 P |
| 4,364,866 A | 12/1982 | Asai et al. ............. 260/239.3 P |
| 4,371,533 A | 2/1983 | Akimoto et al. ........ 424/248.54 |
| 4,424,219 A | 1/1984 | Hashimoto et al. ..... 424/248.54 |
| 4,450,254 A | 5/1984 | Isley et al. ................... 524/399 |
| 4,968,603 A | 11/1990 | Slamon et al. .................. 435/6 |
| 4,981,979 A * | 1/1991 | Sivam ...................... 530/391.9 |
| 5,183,884 A | 2/1993 | Kraus et al. ................. 536/23.5 |
| 5,208,020 A * | 5/1993 | Chari et al. .............. 424/181.1 |
| 5,416,064 A | 5/1995 | Chari et al. .............. 514/229.5 |
| 5,480,968 A | 1/1996 | Kraus et al. .................. 530/326 |
| 5,677,171 A | 10/1997 | Hudziak et al. ........ 435/240.27 |
| 5,725,856 A * | 3/1998 | Hudziak |
| 5,772,997 A | 6/1998 | Hudziak et al. .......... 424/130.1 |
| 5,783,186 A | 7/1998 | Arakawa et al. ......... 424/143.1 |
| 5,821,337 A | 10/1998 | Carter et al. ............. 530/387.3 |
| 5,824,311 A | 10/1998 | Green et al. ............. 424/138.1 |
| 5,837,234 A | 11/1998 | Gentile et al. .............. 424/93.7 |
| 5,840,525 A | 11/1998 | Vandlen et al. ............ 435/69.1 |
| 5,968,517 A | 10/1999 | Duncan et al. ........... 424/195.1 |
| 6,022,541 A * | 2/2000 | Senger et al. ............ 424/172.1 |
| 6,054,297 A * | 4/2000 | Carter et al. ............... 435/69.6 |
| 6,436,931 B1 * | 8/2002 | Chari et al. |

FOREIGN PATENT DOCUMENTS

| | | |
|---|---|---|
| EP | 0 425 235 A2 | 5/1991 |
| WO | 89/06692 | 7/1989 |
| WO | 93/21319 | 10/1993 |
| WO | 94/00136 | 1/1994 |
| WO | 94/22478 | 10/1994 |
| WO | 96/16173 | 5/1996 |
| WO | 97/00271 | 1/1997 |
| WO | 97/04801 | 2/1997 |
| WO | 98/02463 | 1/1998 |
| WO | 98/17797 | 4/1998 |
| WO | 99/31140 | 6/1999 |
| WO | 00/20579 | 4/2000 |
| WO | 00/69460 | 11/2000 |
| WO | 01/00238 A1 | 1/2001 |
| WO | 01/00244 A2 | 1/2001 |
| WO | 01/15730 A1 | 3/2001 |

OTHER PUBLICATIONS

Lewis, G.D. et al, Cancer Immunol. Immunother. 37: 255-263, 1993.*
Xu et al. (Clinical Cancer Research vol. 3(9), pp. 1629-1634, 1997) Abstract only.*
Arteaga, C. L., et al., "p185$^{c\text{-}erbB\text{-}2}$ Signaling Enhances Cisplatin-Induced Cytotoxicity in Human Breast Carcinoma Cells: Association Between an Oncogenic Receptor Tyrosine Kinase and Drug-Induced DNA Repair" Cancer Research, vol. 54, pp. 3758-3765 (1994).
Bacus, S. S. et al., "Tumor-inhibitory Monoclonals Antibodies to the HER-2/Neu Receptor Induce Differentiation of Human Breast Cancer Cells", Cancer Research, vol. 52, pp. 2580-2589 (1992).

(Continued)

*Primary Examiner*—Larry R. Helms
*Assistant Examiner*—Meera Natarajan
(74) *Attorney, Agent, or Firm*—Alex Andrus; James A. Fox; Ginger R. Dreger

(57) ABSTRACT

The application concerns methods of treatment using anti-ErbB receptor antibody-maytansinoid conjugates, and articles of manufacture suitable for use in such methods. In particular, the invention concerns ErbB receptor-directed cancer therapies, using anti-ErbB receptor antibody-maytansinoid conjugates.

27 Claims, 46 Drawing Sheets

OTHER PUBLICATIONS

Fendly, B. M. et al., "Characterization of Murine Monoclonal Antibodies Reactive to Either the Human Epidermal Growth Factor Receptor or HER2/neu Gene Product", Cancer Research, vol. 50, pp. 1550-1558 (1990).

Hancock, M.C. et al., A Monoclonal Antibody Against the c-erbB-2 Protein Enhances the Cytotoxicity of cis-Diamminedichloroplatinum Against Human Breast and Ovarian Tumor Cell Lines:, vol. 51, pp. 4575-4580 (1991).

Issell, B. F. et al., "Maytansine", Cancer Treatment Reviews, vol. 5, pp. 199-207 (1978).

Karsprzyk, P. G. et al., "Therapy of an Animal Model of Human Gastric Cancer Using a Combination of Anti-erbB-2 Monoclonals Antibodies", Cancer Research, vol. 52, pp. 2771-2776 (1992).

Kern, J. A. et al., "p185$^{neu}$ Expression in Human Lung Adenocarcinomas Predicts Shortened Survival", Cancer Research, vol. 50, pp. 5184-5191 (1990).

Lewis, G.D. et al., "Growth Regulation of Human Breast and Ovarian Tumor Cells by Heregulin: Evidence for the Requirement of ErbB2 as a Critical Component in Mediating Heregulin Responsiveness" Cancer Research, vol. 56, pp. 1457-1465 (1996).

Maier, L. A. et al., "Requirements for the Internalization of a Murine Monoclonal Antibody Directed Against the Her-2/neu Gene Product c-erbB-2" Cancer Research, vol. 51, pp. 5361-5369 (1991).

Park, Joo-Bae et al., "Amplification, Overexpression, and Rearrangement of the erbB-2 Protooncogene in Primary Human Stomach Carcinomas", Cancer Research, vol. 49, pp. 6605-6609 (1989).

Database Chemabs Online! Chemical Abstracts Service, Columbus, Ohio, US; Skrepnik, Nebojsa et al., "Effects of anti-erbB-2 (HER-2/neu) Recombinant Oncotoxin Ar209 on Human Non-Small Cell Lung Carcinoma Grown Orthotopically in Athymic Nude Mice" retrieved from STN Database Accession No. 126:14452 XP002164007, Abstract & Clin. Cancer Research Res. (1996), 2(11), 1851-1857.

Sarup, J. C. et al., "Characterization of an Anti-p185$^{HER2}$ Monoclonal Antibody that Stimulates Receptor Function and Inhibits Tumor Cell Growth", Growth Regulation, vol. 1, pp. 72-82 (1991).

Shawyer, L. K. et al., "Ligand-like Effects Induced by Anti-c-erbB2 Antibodies Do Not Correlate with and Are Not Required for Growth Inhibition of Human Carcinoma Cells", Cancer research, vol. 54, pp. 1367-1373 (1994).

Skrepnik, N. et al., "Effects of Anti-erbB2 (HER-2/neu) Recombinant Oncotoxin AR209 on Human Non-Small Cell Lung Carcinoma Grown Orthotopically in Athymic Nude Mice", Clinical Cancer Research, vol. 2, pp. 1851-1857 (1996).

Vitetta, E. S. et al., "Monoclonal Antibodies as Againsts: An Expanded Role for their Use in Cancer Therapy", Cancer Research, vol. 54, pp. 5301-5309 (1994).

Weiner, D. B. et al., "Expression of the neu Gene-encoded Protein (P185$^{neu}$) in Human Non-Small Cell Carcinomas of the Lung", Cancer Research, vol. 50, pp. 421-425 (1990).

Yokota, J. et al., "Amplification of c-erbB2 Oncogene in Human Adenocarcinomas in Vivo", The Lancet, vol. 1, pp. 765-767 (1986).

Yonemura, Y. et al., "Evaluation of Immunoreactivity for erbB-2 Protein as a Marker of Poor Short Term Prognosis in Gastric Cancer", Cancer Research, vol. 51, pp. 1034-1038 (1991).

Aasland et al., "Expression of Oncogenes in Thyroid Tumours Coexpression of c-erbB2/neu and c-erbB", Br. J. Cancer, vol. 57, pp. 358-363 (1988).

Bacus et al., "Differentiation of Cultured Human Breast Cancer Cells (AU-565 and MCF-7) Associated with Loss of Cell Surface HER-2/neu Antigen", Molecular Carcinogenesis, vol. 3, pp. 350-362 (1990).

Baselga et al., "Phase II Study of Weekly Intravenous Recombinant Humanized Anti-p185$^{HER2}$ Monoclonal Antibody in Patients with HER2/neu Overexpressing Metastatic Breast Cancer", J. Clin. Oncol., vol. 14, pp. 737-744 (1996).

Borst et al., "Oncogene Alterations in Endometrial Carcinoma", Gynecol. Oncol., vol. 38, pp. 364-366 (1990).

Carter et al., "Humanization of anti-p185$^{HER2}$ Antibody for Human Cancer Therapy", Proc. Natl. Acad. Sci. USA. vol. 89, pp. 4285-4289 (1992).

Chari et al., "Immunoconjugates Containing Novel Maytansinoids: Promising Anticancer Drugs", Cancer Research, vol. 52, pp. 127-131 (1992).

Chari et al., "Targeted Delivery of Chemotherapeutics: Tumor-Activated Prodrug Therapy", Advanced Drug Delivery Reviews, vol. 31, pp. 89-104 (1998).

Cobleigh et al., "Multinational Study of the Efficacy and Safety of Humanized Anti-HER2 Monoclonal Antibody in Women Who Have HER2-Overexpressing Metastatic Breast Cancer that has Progressed after Cehmotherapy for Metastatic Disease", J. Clin. Oncol., vol. 17, pp. 2639-2648 (1999).

Cohen et al., "Expression Pattern of the neu (NGL) Gene-Coded Growth factor Receptor Protein (p185$^{neu}$) in Normal and Transformed Epithelial Tissues of the Digestive Tract", Oncogene, vol. 4, pp. 81-88 (1989).

Drebin et al., "Monoclonal Antibodies Reactive with Distinct Domains of the neu Oncogene-Encoded p185 Molecule Exert Synergistic Anti-tumor Effects in Vivo", Oncogene, vol. 2, pp. 273-277 (1988).

Drebin et al., "Down-Modulation of an Oncogene Protein Product and Reversion of the Transformed Phenotype by Monoclonal Antibodies", Cell, vol. 41, pp. 695-706 (1985).

D'Souza et al., "Overexpression of ERBB2 in Human Mammary Epithelial Cells Signals Inhibition of Transcription of the E-cadherin Gene", Proc. Natl. Acad. Sci., USA, vol. 91, pp. 7202-7206 (1994).

Guerin et al., "Overexpression of Either c-myc or c-erbB-2/neu Proto-Oncogenes in Human Breast Carcinomas: Correlation with Poor Prognosis" Oncogene Research, vol. 3, pp. 21-31 (1988).

Gu et al., "Overexpression of her-2/neu in Human Prostate Cancer and Benign Hyperplasia", Cancer Letters, vol. 99, pp. 185-189 (1996).

Harweth et al., "Monoclonal Antibodies Against the Extracellular Domain of the erbB-2 Receptor Function as Partial Ligand Agonists", The Journal of Biological Chemistry, vol. 267, No. 21, pp. 15160-15167 (1992).

Hudziak et al., "p185$^{HER2}$ Monoclonal Antibody has Antiproliferative Effects in Vitro Effects in Vitro and Sensitizes Huamn Breast Tumor Cells to Tumor Necrosis Factor", Molecular and Cellular Biology, vol. 9, No. 3, pp. 1165-1172 (1989).

Klapper et al., A Subclass of Tumor-inhibitory Monoclonal Antibodies to ErbB-2/HER2 Blocks Crosstalk with Growth Receptors:, Oncogene, vol. 14, pp. 2099-2109 (1997).

Kraus et al., Isolation and Characterization of ERBB3, a Third Member of the ERBB/epidermal Growth Factor Receptor Family: Evidence for Overexpression in a Subset of Human Mammry Tumors: Proc. Natl. Acad. Sci. USA, vol. 86, pp. 9193-9197 (1989).

Kumar et al., "Regulation of Phosphorylation of the c-erbB-2/HER2 Gene Product by a Monoclonal Antibody and Serum Growth Factor(s) in Human Mammry Carcinoma Cells", Molecular and Cellular Biology, vol. 11, No. 2, pp. 979-986 (1991).

Lewis et al., "Differential Responses of Human Tumor Cell Lines to Anti-p185$^{HER2}$ Monoclonal Antibodies", Cancer Immunol. Immunother, vol. 37, pp. 255-263 (1993).

McCann et al., "c-erbB-2 Oncoprotein Expression in Primary Human Tumors", Cancer, vol. 65, pp. 89-92 (1990).

McKenzie et al., "Generation and Characterization of Monoclonal Antibodies Specific for the Human neu Oncogene Product, p185", Oncogene, vol. 4, pp. 543-548 (1989).

Myers et al., "Biological Effects of Monoclonal Antireceptor Antibodies Reactive with neu Oncogene Product, p185$^{neu}$", Methods in Enzymology, vol. 198, pp. 277-290 (1991).

Pietras et al., "Antibody to HER-2/neu Receptor Blocks DNA Repair after Cisplatin in Human Breast and Ovarian Cancer Cells", Oncogene, vol. 9, pp. 1829-1838 (1994).

Plowman et al., "Heregulin Induces Tyrosine Phosphorylation of HER4/P180$^{ERBb4}$", Letters to Nature, vol. 366, pp. 473-475 (1993).

Plowman et al., "Ligand-specific Activation of HER4/p180$^{erbB4}$, a Fourth Member of the Epidermal Growth Factor Receptor Family", Proc. Natl. Acad. Sci. USA, vol. 90, pp. 1746-1750 (1993).

Liu et al., "Eradication of Large Colon Tumor Xenografts by Targeted Delivery of Maytansinoids", Proc. Natl. Acad. Sci. USA, vol. 93, pp. 8618-8623 (1996).

Ross et al., "Prognostic Significance of HER-2/neu Gene Amplification Status by Fluorescence in Situ Hybridization of Prostate Carcinoma", Cancer, vol. 79, pp. 2162-2170 (1997).

Ross et al., "HER-2/neu Gene Amplification Status in Prostate Cancer by Fluorescense in Situ Hybridization", Human Pathology, vol. 28, No. 7, pp. 827-833 (1997).

Sadasivan et al., "Overexpression of HER-2/NEU May be an Indicator of Poor Prognosis in Prostate Cancer", The Journal of Urology, vol. 150, pp. 126-131 (1993).

Schaefer et al., "γ-Heregulin: A Novel Heregulin Isoform that is an Autocrine Growth Factor for the Human Breast Cancer Cell Line, MDA-MB-175", Oncogene, vol. 15, pp. 1385-1394 (1997).

Scott et al., "p185$^{HER2}$ Signal Transduction in Breast Cancer Cells", The Journal of Biological Chemistry, vol. 266, No. 22, pp. 14300-14305 (1991).

Shepard et al., "Monoclonal Antibody Therapy of Human Cancer: Taking the HER2 Protoocogene to the Clinic", Journal of Clinical Immunology, vol. 11, No. 3 (1991).

Slamon et al., "Human Breast Cancer: Correlation of Relapse and Survival with Amplification of the HER-2/neu Oncogene", Science, vol. 235, pp. 177-182 (1987).

Slamon et al., "Studies of the HER-2/neu Proto-Oncogene in Human Breast and Ovarian Cancer", Science, vol. 244, pp. 707-712 (1989).

Sliwkowski et al., "Coexpression of erbB2 and erbB3 Proteins Reconstitutes a High Affinity Receptor for Heregulin", Yhe Journal of Biological Chemistry, vol. 269, No. 20, pp. 14661-1665 (1994).

Spector et al., "Study of the Biologic Effects of Lapatinib, a Reversible Inhibitor of ErbB1 and ErbB2 Tyrosine Kinases, on Tumor Growth and Survival Pathyways in Patients With Advanced Malignancies", Jour. of CLin. Onc., vol. 23, No. 11, pp. 2502-2512 (2005).

Stancovski et al., "Mechanistic Aspects of the Opposing Effects of Monoclonal Antibodies to the ERBB2 Receptor on Tumor Growth", Proc. Natl. Acad. Sci. USA, vol. 88, pp. 8691-8695 (1991).

Tagliabue et al., "Selection of Monoclonal Antibodies which Induce Internalization and Phosphorylation of p185$^{HER2}$ and Growth Inhibition of Cells with HER2/NEU Gene Amplification", Int. J. Cancer, vol. 47, pp. 933-937 9 (1991).

Williams et al., "Expression of c-erbB-2 in Human Pancreatic Adenocarcinomas", Pathobiology, vol. 59, pp. 46-52 (1991).

Xu et al., "Antibody-Induced Growth Inhibition is Mediated Through Immunochemically and Functionally Distinct Epitopes on the Extracellular Domain of the c-erbB-2 (HER-2/neu) Gene Product", Int. J. Cancer, vol. 53, pp. 401-408 (1993).

Zhau et al., "Amplification and Expression of the c-erb B-2/neu Proto-Oncogene in Human Bladder Cancer", Molecular Carcinogenesis, vol. 3, pp. 254-257 (1990).

King et al., "Amplification of a Novel v-erbB-Related Gene in a Human Mammary Carcinoma", Science, vol. 229, pp. 974-976 (1985).

Fukushige et al., "Localization of a Novel v-erbB-Related Gene, c-erbB-2, on Human Chromosome 17 and its Amplification in a Gastric Cancer Cell Line", Molecular and Cellular Biology, vol. 6, No. 3, pp. 955-958 (1986).

Database Chemabs Online!, Chemical Abstracts Service, Columbus, Ohio, US; Brechbiel, Martin W. et al.: "Synthesis and Evaluation of Antiproliferative Activity of a Geldanamycin-herceptin Immunoconjugate" Retrieved from STN Database Accession No. 2000:796068, XP002164006, Abstract & Abstr. Pap.-Am. Chem. Soc. (2000), 220$^{th}$, Medi-071.

Erickson H.K et al., "Antibody-Maytansinoid Conjugates are activated in targeted cancer cells by Lysosomal degradation and Linker-Dependent Intracellular Processing", Cancer Res. 66: (8), pp. 4426-4433, (2006).

Chari, RVJ "Targeted delivery of chemotherapeutics: tumor-activated prodrug therapy," Advanced Drug Delivery Reviews 31:89-104 (1998).

Spector et al., "Study of the Biologic Effects of Lapatinib, a Reversible Inhibitor of ErbB1 and ErbB2 Tyrosine Kinases, on Tumor Growth and Survival Pathways in Patients With Advanced Malignancies," Jour. of Clin. Onc. 23(11):2502-2512 (2005).

Arteaga, C.L. et al., "p185$^{c-erbB-2}$ Signaling Enhances Cisplatin-induced Cytotoxicity in Human Breast Carcinoma Cells: Association between an oncogenic Receptor Tyrosine Kinase and Drug-induced DNA Repair," Cancer Research, vol. 54, pp. 3758-3765 (1994).

Bacus, S.S. et al., "Tumor-inhibitory Monoclonal Antibodies to the HER-2/Neu Receptor Induce Differentiation of Human Breast Cancer Cells," Cancer Research, vol. 52, pp. 2580-2589 (1992).

Fendly, B.M. et al., "Characterization of Murine Monoclonal Antibodies Reactive to Either the Human Epidermal Growth Factor Receptor or HER2/neu Gene Product," Cancer Research, vol. 50, 1550-1558 (1990).

Hancock, M.C. et al., "A Monoclonal Antibody against the c-erbB-2 Protein Enhances the Cytotoxicity of cis-Diamminedichloroplatinum against Human Breast and Ovarian Tumor Cell Lines," vol. 51, pp. 4575-4580 (1991).

Issell, B.F. et al., "Maytansine," Cancer Treatment Reviews, vol. 5, pp. 199-207 (1978).

Kasprzyk, P.G. et al., "Therapy of an Animal Model of Human Gastric Cancer Using a Combination of Anti-erbB-2 Monoclonal Antibodies," Cancer Research, vol. 52, pp. 2771-2776 (1992).

Kern, J.A. et al., "p185$^{neu}$ Expression in Human Lung Adenocarcinomas Predicts Shortened Survival," Cancer Research, vol. 50, pp. 5184-5191 (1990).

Maier, L.A. et al., "Requirements for the Internalization of a Murine Monoclonal Antibody Directed against the HER-2/neu Gene Product c-erbB-2," Cancer Research, vol. 51, pp. 5361-5369 (1991).

Park, Joo-Bae et al., "Amplification, Overexpression, and Rearrangement of the erbB-2 Protooncogene in Primary Human Stomach Carcinomas," Cancer Research, vol. 49, pp. 6605-6609 (1989).

Database Chemabs 'Online! Chemical Abstracts Service, Columbus, Ohio, US; Skrepnik, Nebojsa et al: "Effects of anti-erbB-2(HER-2/neu) recombinant oncotoxin Ar209 on human non-small cell lung carcinoma grown orthotopically in athymic nude mice" retrieved from STN Database accession No. 126:14452 XP002164007, abstract & Clin. Cancer Res. (1996), 2(11), 1851-1857.

Sarup, J.C. et al., "Characterization of an Anti-p185$^{HER2}$ Monoclonal Antibody that Stimulates Receptor Function and Inhibits Tumor Cell Growth," Growth Regulation, vol. 1, pp. 72-82 (1991).

Shawver, L.K. et al., "Ligand-like Effects Induced by Anti-c-erbB-2 Antibodies Do Not Correlate with and Are Not Required for Growth Inhibition of Human Carcinoma Cells," Cancer Research, vol. 54, pp. 1367-1373 (1994).

Skrepnik, N. et al., "Effects of Anti-erbB2 (HER-2/neu) Recombinant Oncotoxin AR209 on Human Non-Small Cell Lung Carcinoma Grown Orthotopically in Athymic Nude Mice," Clinical Cancer Research, vol. 2, pp. 1851-1857 (1996).

Vitetta, E.S. et al., "Monoclonal Antibodies as Agonists: An Expanded Role for Their Use in Cancer Therapy," Cancer Research, vol. 54, pp. 5301-5309 (1994).

Weiner, D.B. et al., "Expression of the neu Gene-encoded Protein (P185$^{neu}$) in Human Non-Small Cell Carcinomas of the Lung," Cancer Research, vol. 50, pp. 421-425 (1990).

Yokota, J. et al., "Amplification of c-erbB2 Oncogene in Human Adenocarcinomas in Vivo," The Lancet, vol. 1, pp. 765-767 (1986).

Yonemura, Y. et al., "Evaluation of Immunoreactivity for erbB-2 Protein as a Marker of Poor Short Term Prognosis in Gastric Cancer," Cancer Research, vol. 51, pp. 1034-1038 (1991).

* cited by examiner

VARIABLE HEAVY DOMAIN

```
              10          20             30           40
2C4     EVQLQQSGPELVKPGTSVKISCKAS [GFTFTDYTMD] WVKQS
          **           *   *                     * *
574     EVQLVESGGGLVQPGGSLRLSCAAS [GFTFTDYTMD] WVRQA
                                              ***  *
hum III EVQLVESGGGLVQPGGSLRLSCAAS [GFTFSSYAMS] WVRQA 50   a      60           70           80
2C4     HGKSLEWIG [DVNPNSGGSIYNQRFKG] KASLTVDRSSRIVYM
         *   *                        *         *
574     PGKGLEWVA [DVNPNSGGSIYNQRFKG] RFTLSVDRSKNTLYL
                                      ****  *
hum III PGKGLEWVA [VISGDGGSTYYADSVKG] RFTISRDNSKNTLYL abc    90     100ab           110
2C4     ELRSLTFEDTAVYYCAR [NLGPSFYFDY] WGQGTTLTVSS
        ***  *                            *
574     QMNSLRAEDTAVYYCAR [NLGPSFYFDY] WGQGTLVTVSS
                                       *********
hum III QMNSLRAEDTAVYYCAR [GRVGYSLYDY] WGQGTLVTVSS
```

FIG. 1

Variable Light Domain

```
            10         20         30         40
2C4    DTVMTQSHKIMSTSVGDRVSITC [KASQDVSIGVA] WYQQRP
         **    *****          *                *
574    DIQMTQSPSSLSASVGDRVTITC [KASQDVSIGVA] WYQQKP
                                             ** ***
hum KI DIQMTQSPSSLSASVGDRVTITC [KASQDVSIGVA] WYQQKP 50         60         70         80
2C4    GQSPKLLIY [SASYRYT] GVPDRFTGSGSGTDFTFTISSVQA
         **                    *    *       *   * *
574    GKAPKLLIY [SASYRYT] GVPSRFSGSGSGTDFTLTISSLQP
                    *****
hum KI GKAPKLLIY [AASSLES] GVPSRFSGSGSGTDFTLTISSLQP 90        100
2C4    EDLAVYYC [QQYYIYPYT] FGGGTKLEIKRT
         * *                  *
574    EDFATYYC [QQYYIYPYT] FGQGTKVEIKRT
                  *** *
hum KI EDFATYYC [QQYNSLPWT] FGQGTKVEIKRT
```

FIG. 2

```
                                              rmaI
            hgiAI/aspHI                       maeI
   sau3AI                sau3AI
   mboI/ndeII   tru9I    mboI/ndeII
   dpnII bsp1286         dpnII    nheI         nlaIII  tseI
   pvuI/bspCI    mseI    dpnI cac8I    tseI    sphI    fnu4HI/bsoFI
   mcrI  bsiHKAI nlaIII thaI cac8I             nspHI   bbvI
   bsiEI bmyI tsp509I    fnuDII/mvnI  cac8I            scfI
      taqI    asel/asnI/vspI bstUI bfaI aluI nspI      pstI
   aluI dpnI  apaLI/snoI   rcaI   bsh1236I fnu4HI/bsoFI cac8I
           alw44I/snoI bspHI nruI aluI bbvI   cac8I bsgI            aval
 1 AAGCTCGATC GGTGCACATT AATTCATGAT CGCGAGCTAG CAGCTTGCAT GCCTGCAGCA GAAATGGTTG AACTCCCGAG AGTGTCCTAC ACCTAGGGGA
   TTCGAGCTAG CCACGTGTAA TTAAGTACTA GCGCTCGATC GTCGAACGTA CGGACGTCGT CTTTACCAAC TTGAGGGCTC TCACAGGATG TGGATCCCCT
   ^start of linker 1                                           ^end of linker 1       ^start of MMTV promoter hgiJII
                                                     bsp1286
                                             hinPI   bmyI
          styI                               hhaI/cfoI        banII
          bsaJI                       msaI   aviII/fspI foki
       tseI       styI       bcgI            bstF5I
       fnu4HI/bsoFI  bsaJI   ahdI/eam1105I
       bbvI
101 GAAGCAGCCA AGGGGTTGTT TCCCACCAAG GACGACCCGT CTGCGCACAA ACGGATGAGC CCATCAGACA AAGACATATT CATTCTCTGC TGCAAACTTG
    CTTCGTCGGT TCCCCAACAA AGGGTGGTTC CTGCTGGGCA GACGCGTGTT TGCCTACTCG GGTAGTCTGT TTCTGTATAA GTAAGAGACG ACGTTTGAAC mwoI
                                             mwoI                                              tseI
                                             cac8I  hgiJII                                     fnu4HI/bsoFI
                                             hgiAI/aspHI                                       bbvI
                                   mwoI      bsp1286          bmyI                    mboII
                                   acil      bsiHKAI  bmyI    banII hphI    pleI      earI/ksp632I
       aluI                                  bmyI             banII hphI    plel    tru9I sapI     mamI
                                                                                    msel aluI      bsaBI
201 GCATAGCTCT GCTTTGCTGG GGCATTGGGG GAAGTTGCGG TTCGTGCTCG CAGGGCTCTC ACCCTTGACT CTTTTAATAG CTCTTCTGTG CAAGATTACA
    CGTATCGAGA CGAAACGACC CCGTAACCCC CTTCAACGCC AAGCACGAGC GTCCCGAGAG TGGGAACTGA GAAAATTATC GAGAAGACAC GTTCTAATGT
```

```
                rmaI
                maeI                                                                          rmaI
                bfaI           styI                                           nlaIII          maeI
     pleI       aluI           bsaJI              smlI                        rsaI            bfaI      bsmI
     hinfI      mnlI           bsmAI      mboII        nlaIII                 csp6I   GGTACATGAT TATATTTATC TAGGAACAGG
801 AAAGACTCGC CAGAGCTAGA CCTCCTTGGT GTATGTTGTC TCAAGAAGAA AAAGACGACA TGAAACAACA                TATATTTATC TAGGAACAGG
    TTTCTGAGCG GTCTCGATCT GGAGGAACCA CATACAACAG AGTTCTTCTT TTTCTGCTGT ACTTTGTTGT CCATGTACTA ATATAAATAG ATCCTTGTCC tspRI
                                                          alwNI
                              styI                                                      nlaIII
                              bsII        bsmFI
                              bsII bsaJI mnlI       alw26I/bsmAI
 01 AATGCACTTT TGGGAAAGA TTTTCCATAC CAAGGAGGGG ACAGTGGCTG GACTAATAGA ACATTATTCT GCAAAAACTT ATGGCATGAG TTATTATGAA
    TTACGTGAAA ACCCCTTTCT AAAAGGTATG GTTCCTCCCC TGTCACCGAC CTGATTATCT TGTAATAAGA CGTTTTTGAA TACCGTACTC AATAATACTT tru9I
                         styI       mseI                                foreI
               sau96I               smlI                                bstF5I
               haeIII/palI nlaIV    aflII/bfrI     maeIII               mnlI   bsmAI
               asuI     acII bsaJI  CAAGGCTTAA GTAAGTTTTT GGTTACAAAC TGTTCTTAAA ACGAGGATGT GAGACAAGTG CTTTGGTGAC
001 TAGCCTTTAT TGGCCCAACC TTGCGGTTCC                               ACAAGAATTT TGCTCCTACA CTCTGTTCAC CAAAGGACTG
    ATCGGAAATA ACCGGGTTGG AACGCCAAGG GTTCCGAATT CATTCAAAAA CCAATGTTTG sstI
               sacI
               hgiJII
               hgiAI/aspHI
               ecl136II
               bsp1286
               bsiHKAI                                                        tsp509I
               bmyI                                                           apoI
               ddeI                               TCTATTTTCC TATGTTCTTT TGGAATTTAT CCAAATCTTA TGTAAATGCT TATGTAAACC
               sau3AI
               mboII/ndeII
               dpnII aluI
               dpnI banII ddeI
101 TTGGTTTGGT ATCAAAGGTT CTGATCTGAG CTCTGAGTGT                               TGGAATTTAT CCAAATCTTA TGTAAATGCT TATGTAAACC
    AACCAAACCA TAGTTTCCAA GACTAGACTC GAGACTCACA AGATAAAAGG ATACAAGAAA ACCTTAAATA GGTTTAGAAT ACATTTACGA ATACATTTGG

```
                                                                              fnu4HI/bsoFI
                                                                      ncrI
                                                                      eagI/xmaIII/eclXI
                                                                      eaeI
                                                            scrFI     cfrI
                                                            mvaI      notI
                                                            ecoRII    fnu4HI/bsoFI
                                                            dsaV      tru9I haeIII/palI              tsp509I
                                                            bstNI     mseI bsiEI hindIII             ecoRI
                                                            bssKI           alul smlI acil acil aluI taqI
                                    fokI                    apyI      tsp509I afIII/bfrI cacBI       ecoRV apoI
                                    bstF5I                  bslI bsaJI
 501 CACCTATTGG TCTTACTGAC ATCCACTTTG CCTTTCTCTC CACAGGTGTC CACTCCCAGG TTCAATTACA GCTCTTAAGC GGCGCAAGC TTGATATCGA
     GTGGATAACC AGAATGACTG TAGGTGAAAC GGAAAGAGAG GTGTCCACAG GTGAGGGTCC AAGTTAATGT CGAGAATTCG CCGCCGTTCG AACTATAGCT
                                                                      ^end of chimeric intron at pCI 989
                                                                                           end of BS insert at HindIII^ hinPI
                                      hhaI/cfoI
                                      thaI
                                      fnuDII/mvnI
                                      bstUI
                                      bsh1236I
                                      mwoI      sau96I
                                      hinPI     mspI                                              mwoI
                                      hhaI/cfoI                                                   hinPI  thaI
                                      cacBI hpaII                                                 thaI   fnuDII/
                                      bssHII    nlaIV                                             hhaI/cfoI
                                      thaI      scrFI                                             thaI   fnuDII/
                                      fnuDII/mvnI                                         mwoI    fnuDII/mvnI
                                 mnlI bstUI nclI                                                  bstUI bstUI
                                 xhoI bsh1236I haeIII/palI                                tseI    bsh1236I
                                 smlI hinPI dsaV                                          fnu4HI/bsoFI bsh1236
                                 paeR7I hhaI/cfoI asuI                                    mnlI bbvI acil  acil
                  alul  avaI cacBI     cauII
           hindIII taqI bssHII bssKI
 601 ATTCCTGCAG CCCGGGGGAT CCACTAGTGG ATCCAAAGAA TTCAAAAAGC TTCTCGAGGG CCCCCACCC GCCCCCACCC CTCGCAGCAC CCCGGGCCCC
     TAAGGACGTC GGGCCCCCTA GGTGATCACC TAGGTTTCTT AAGTTTTTCG AAGAGCTCCC GCGCGGGGGC CGGGGGTGGG GAGCGTCGTG GGGCGGCGGG
                                             ^end of BS intron insert at spe
                                                                                  ^start of human HER2 from BS at xhol
```

```
                                                                haeIII/palI
                                                                eaeI
                                                                cfrI
                                                                scrFI
                                                                mvaI
                                                                ecoRII
                                                                dsaV
                                                                bstNI
                                                                bssKI         rmaI
                                                                apyI  maeI              bsmAI mspAII/nspBII
                                                                bsaJI bfaI              bsaI  aciI
          bsmFI       alwNI
          sau96I      alw26I/bsmAI
          nlaIV       mwoI
          avaII       bstAPI
          asuI    scfI       mwoI                                mnlI
          ppuMI   pstI  tseI                nlaIV
          bspMI   bsgI fnu4HI/bsoFI  hgiCI
              mnlI tspRI    bbvI       banI
              mnlI ecoO109I/draII mnlI aciI  mnlI    aluI   mnlI
001 GTGAGGCAGG TCCCACTGCA GAGGCTGCGG ATTGTGCGAG GCACCCAGCT CTTTGAGGAC AACTATGCCC TGGCCGTGCT AGACAATGGA GACCCGGTGA
    CACTCCGTCC AGGGTGACGT CTCCGACGCC TAACACGCTC CGTGGGTCGA GAAACTCCTG TTGATACGGG ACCGGCACGA TCTGTTACCT CTGGGCGACT
 91  V  R  Q  V  P  L  Q   R   L  R   I  V  R  G   T  Q  L   F  E  D   N  Y  A   L  A  V  L   D  N  G   D  P  L  N scrFI            tseI
                                           mvaI             fnu4HI/bsoFI
                                           ecoRII           bbvI
                                           dsaV             scfI     taqI
                                     mnlI  bstNI            pstI     sfuI                              mspAII/nspB
                                     haeIII/palI            bsgI     bstBI             sau3AI
                          tsp45I sau96I bssKI cac8I haeIII/palI tseI  bsiCI            mboI/ndeII
                          maeIII asuI  apyI stuI               fnu4HI/bsoFI            dpnII
                                ecoNI   nlaIV bsaJI mnlI  mwoI bbvI asuI              bstYI/xhoI         dpnI    nlaIV
                          bsiI      ecoO109I/draII haeI aciI aluI aluI          mnlI   bglII      mnlI  alwI  aciI
101 ACAATACCAC CCCTGTCACA GGGGCCTCCC CAGGAGGCCT GCGGGAGCTG CAGCTTCGAA GCCTCACAGA GATCTTGAAA GGAGGGGTCT TGATCCAGCG
    TGTTATGGTG GGGACAGTGT CCCCGGAGGG GTCCTCCGGA CGCCCTCGAC GTCGAAGCTT CGGAGTGTCT CTAGAACTTT CCTCCCCAGA ACTAGGTCGC
125  N  T  T   P  V  T   G  A  S  P   G  G  L   R  E  L   Q  L  R  S   L  T  E   I  L  K   G  G  V  L   I  Q  R haeIII/
                                                                  cac8I                           bsrBI  sau96I
                                           scrFI                  aluI                            bslI   asuI
                                           mvaI                   pvuII                           aciI  avaI
                                           ecoRII                 mspAII/nspBII tspRI
                                           dsaV
                                           bstNI                      mboII
                                           bssKI
    aluI                                   apyI
201 GAACCCCCAG CTCTGCTACC AGGACACGAT TTTGTGGAAG GACATCTTCC ACAAGAACAA CCAGCTGGCT CTCACACTGA TAGACACCAA CCGCTCTCGG
    CTTGGGGGTC GAGACGATGG TCCTGTGCTA AAACACCTTC CTGTAGAAGG TGTTCTTGTT GGTCGACCGA GAGTGTGACT ATCTGTGGTT GGCGAGAGCC
158  N  P  Q  L  C  Y  Q  D  T  I   L  W  K  D  I  F  H   K  N  N  Q  L  A  L  T  L  I   D  T  N  R  S  R
```

FIG. 7G

```
                                                                  hinPI
                                                                  hhaI/cfoI
                                    mspAII/nspBII                 thaI
                            mwoI tseI                             fnuDII/mvnI
                            nlaIV fnu4HI/bsoFI                    bstUI
                      hgiJII bslI                           mwoI bshl236I                                             mspI
                      bsp1286 bbvI                          mnlI alwNI hgaI                                           hpaII mwoI
                      bmyI   aciI                           ddeI alw26I/bsmAI        tspRI                            cfr10I/bsrFI
        cac8I         banII bslI                                                                                      GCCGGTGGCT
301 GCCTGCCACC CCTGTTCTCC GATGTGTAAG GGCTCCCGCT GCTGGGGAGA GAGTTCTCAG GCCTGACGCG CACTGTCTGT CCCGGTGGCT
    CGGACGGTGG GGACAAGAGG CTACACATTC CCGAGGGCGA CGACCCCTCT CTCAAGAGTC CGGACTGCGC GTGACAGACA CGGCCACCGA
191  A  C  H  P  C  S  P  M  C  K  G  S  R  C  W  G  E  S  S  E  D  C  Q  S  L  T  R  ?  V  C  A  G  G  C sau96I
                                                  nlaIV
                                                  haeIII/paII                    haeIII/paII
                                                  sau96I                         haeI
                                          tseI    pspOMI/bsp120I                 scrFI
                                          mwoI    nlaIV                          mvaI
                                          mspI    hgiJII                         ecoRII
                                          hpaII   ecoO109I/draII                 dsaV
                                          naeI/ngoMI bsp1286                     bstNI
                                          cfr10I/bsrFI bmyI                      bssKI
                            tseI          cac8I   asuI                           apyI
                            fnu4HI/bsoFI  tseI    fnu4HI/bsoFI                   mwoI cac8I mnlI
                            bbvI nlaIII tspRI     fnu4HI/bsoFI bbvI              CCTGCCTCCA
            tseI                                  bbvI bbvI     apaI             GGACGGAGGT
            fnu4HI/bsoFI
            mspAII/nspBII   tspRI
            bslI    sau96I
            aciI    asuI    haeIII/paII
        cac8I
        bsp1286
        bmyI bbvI  nlaIV    tspRI
401 GTGCCCGCTG CAAGGGCTG CTGCCCACTG ACTGCTGCCA TGAGCAGTGT GCTGCCGGCT GCACGGGCCC CAAGCACTCT GACTGCTGG CCTGCCTCCA
    CACGGGCGAC GTTCCCGAC GACGGGTGAC TGACGACGGT ACTCGTCACA CGACGGCCGA CGTGCCCGGG GTTCGTGAGA CTGACGGACC GGACGGAGGT
225  A  R  C  K  G  P  L  P  T  D  C  C  H  E  Q  C  A  A  G  C  T  G  P  K  H  S  D  C  L  A  C  L  H
```

FIG. 7H

```
                                                    bstEII
                                                     scrFI
                                                      mvaI
                                                     ecoRII
                                                      dsaV
                                      tseI          bstNI
                                   fnu4HI/bsoFI    bssKI hphI                                                              bst2171
                                      bbvI       apyI tsp45I                                                                mspI
                              aluI tspRI bsII bsaJI maeIII                                                            sau96I bstll07I
                                                  afllII hinfI nlaIII                            tail              mnlI hpaII
       tspRI sfanI                                                                              maeII pleI     bslI haeIII/palI
                                                                                                            bsaJI cfr10I/bsrFI
2501 CTTCAACCAC AGTGGCATCT GTGAGCTGCA CTCCCAGCC CTGGTCACCT ACAACACAGA CACGTTTGAG TCCATGCCCA ATCCCGAGGG CCGTATACA
     GAAGTTGGTG TCACCGTAGA CACTCGACGT GACGGGTCGG GACCAGTGA TGTTGTGTCT GTGCAAACTC AGGTACGGGT TAGGGCTCCC GGCCATATGT
 258  F  N  H  S  G  I  C  E  L  H  C  P  A  L  V  T  Y  N  T  D  T  F  E  S  M  P  N  P  E  G  R  Y  T cac8I
         hinPI
        hhaI/cfoI
         nlaIV
         narI
         kasI
        hinII/acyI
         hgiCI
       haeII aluI   ahdI/eam1105I
      eheI pvuII    tsp45I                                                                                      tsp45I
      banI mspAlI/nspBII                                       sau3AI                                          maeIII
     ahaII/bsaHI maeIII                                      mboI/ndeII                                         hphI
                          bsmFI                               dpnII                                             mnlI
                                                 bslI         dpnI                                              mnII
                                               taiI banHI     alwI                                 hgiAI/aspHI
                                              maeII alwI      nlaIV                                  bspl286
                                                            bstYI/xhoII                              bsiHKAI
                                                                                        mnlI         bmyI          hphI      bsrI
2601 TTCCGGCGCCA GCTGTGTGAC TGCCTGTCCC TACAACTACC TTTCTACGGA CGTGGGATCC TGGCCCCTCG TGCACCCTCG GCACAACCRA GAGGTGACAG
     AAGCCGCGGT CGACACACTG ACGGACAGGG ATGTTGATGG AAAGATGCCT GCACCCTAGG ACGTGGGAGC ACGTGGGGGA CGTGTTGGTT CTCCACTGTC
 291  F  G  A  S  C  V  T  A  C  P  Y  N  Y  L  S  T  D  V  G  S  C  T  L  V  C  P  L  H  N  Q  E  V  T  A fokI           acil        aval                                                                        mnlI   maeIII
        bstF5I       mspAlI/nspBII  tseI                                               nlaIII         mnlI mnlI  hphI
         mnlI          msII      fnu4HI/bsoFI bspl286                                                mnlI mnlI hphI     mnlI
                                      bbvI        bmyI
2701 CAGAGGATGG AACACAGCGG TGTGAGAAGT GCAGCAAGCC CTGTGCCCGA GTGTGCTATG GTCTGGGCAT GTCTGGGCTTG CGAGAGGTGA GGGCAGTTAC
     GTCTCCTACC TTGTGTCGCC ACACTCTTCA CGTCGTTCGG GACACGGGCT CACACGATAC CAGACCCGTA CAGACCCGAAC GCTCTCCACT CCCGTCAATG
 325  E  D  G  T  Q  R  C  E  K  C  S  K  P  C  A  R  V  C  Y  G  L  G  M  E  H  L  R  E  V  R  A  V  T
```

FIG. 7I

```
                                                                    sau96I
                                                                    nlaIV
                                       sau3AI         scrFI         avaII
                                       mboI/ndeII    mvaI           asuI
                                       dpnII         ecoRII         sanDI
                     xcmI              dpnI          dsaV           ppuMI
                     scrFI                    bstYI/xhoII  bstNI    nlaIV
                     mvaI                     tseI           bssKI           ecoO109I/draII
                     ecoRII                   fnu4HI/bsoFI          apyI                    bsmFI        mnlI       tspRI
                     dsaV                     bbvI            bglII           mspI                      
      tspRI          bstNI      apyI         cac8I            mboII          hpaII aluI    bsmFI
                     bssKI                                    nlaIV
801  CAGTGCCAAT ATCCAGGAGT TTGCTGGCTG CAAGAAGATC TTTGGAGCC TGGCATTTCT GCCGGAGCC TTTGATGGGC ACCCAGCCTC CAACACTGCC
     GTCACGGTTA TAGGGTCCTCA AACGACCGAC GTTCTTCTAG AAACCCTCGG ACCGTAAAGA CGGCCTCCGG AAACTACCCG TGGGTCGGAG GTTGTGACGG
358    S  A  N    I  Q  E  F    A  G  C      K  K  I      F  G  S    L  A  F  L      P  E  S      F  D  G  D      P  A  S      N  T  A mspI
                                                                                             hpaII
                                                        sau3AI                               haeIII/paII
                                                        mboI/ndeII                           eaeI                  ddeI    bpuAI
                                   alluI                dpnII                                cfrI                  mnlI    bbsI
       bpmI/gsuI    tseI           pleI     mboII   dpnI     maeIII                          nlaIII               drdI    hgaI
       bsrBI        fnu4HI/bsoFI   hinfI    earI/ksp632I     bstEII              ddeI        cac8I     CAGCCTGCCT GACCTCAGCG
       aciI   mwoI  bbvI           bsmAI  GAGACCTGG AAGAGATCA AGTTACCTA  TACACTCAG ATGTAGAGTC  GTACGGCCCT GTCGGACGGA CTGGAGTCGC
901  CCCCTCCAGC CAGAGCAGT CCAAGTGTTT GAGACCTGG AAGAGATCA AGTTACCTA TACACTCAG ATGTAGAGTC CATGGCCGGA CAGCCTGCCT GACCTCAGCG
     GGGCGAGGTCG GTCTCGTCA GGTTCACAAA CTCTGGACC TTCTCTAGTG TCCAATGGAT ATGTAGAGTC GTACCGGCCT GTCGGACGGA CTGGAGTCGC
391    P  L  Q  P    E  Q  L      Q  V  F      E  T  L  E      E  I  T      G  Y  L    Y  I  S  A      W  P  D      S  L  P      D  L  S  V hinPI
                                                hhaI/cfoI
                                                nlaIV
                                                narI                                                                 hinPI
                        bsmFI                   kasI                                                                 hhaI/cfoI
                        scrFI                   hinII/acyI                                             pvuII         tseI
                        nciI                    hgiCI                                                  mspAII/nspBII fnu4HI/bsoFI
                        mspI                    haeII                                     bslI         sfaNI aluI mwoI bbvI        tspRI
          alwNI         hpaII         cauII     ehelI             ahaII/bsaHI mwoI
          alw26I/bsmAI  dsaV          bssKI     banI              
    mboII   bspMI                     bsaJI    tsp509I            
001  TCTTCCAGAA CCTGCAAGTA ATCCGGGAC GAATTCTGCA CAATGGCGCC TACTCGCTGA CCCTGCAAGG GCTGGGCATC AGCTGGCTGG GGCTGCGCTC
     AGAAGGTCTT GGACGTTCAT TAGGCCCTG CTTAAGACGT GTTACCGCGG ATGAGCGACT GGGACGTTCC CGACCCGTAG TCGACCGACC CCGACGCGAG
425    F  Q  N    L  Q  V      I  R  G      R  I  L  H      N  G  A      Y  S  L  T      L  Q  G      L  G  I  S      W  L  G      L  R  S

```
                                                                                            talI
                                                                                            maeII    esp3I
                                                                                            hinlI/acyI bsmAI
                                                                  tseI                      ahaII/bsaHI
                                          scrFI                   fnu4HI/bsoFI                          bsmBI   aciI
                                          mvaI                    bbvI  aciI      cac8I mnlI aatII
                                          ecoRII
                                          dsaV
                                          bstNI
                                          bssKI
                                          apyI
                              sau96I
                              avaII fokI
                   msII       asuI  bstF5I
3601 AGCCTTGCCC CATCAACTGC ACCCACTCCT GTGTGGACCT GGATGACAAG GCTGCCCCG CCGAGCAGAG AGCCAGCCCT CTGACGTCCA TGTCTCTGC
     TCGGAACGGG GTAGTTGACG TGGGTGAAGA CACACCTGGA CCTACTGTTC CCGACGGGGC GGCTCGTCTC TCGGTCGGGA GACTGCAGGT AGCAGAGACG
625   P  C  P  I  N  C  T  H  S  C  V  D  L  D  D  K  G  C  P  A  E  Q  R  A  S  P  L  T  S  I  V  S  A mspI
                                                                       mroI
                                                                       bspMII
                                                                       bspEI
                                          mnlI                         bsaWI
                                          sau3AI                       sau3AI
                                          mboI/ndeII                   mboI/ndeII
                                          manI                         dpnII
                                          dpnII                        dpnI
                                          dpnI                         alwI
                                          bsaBI
                                          alwI
                                          nlaIV                                          tseI
                                          bstYI/xhoII                                    fnu4HI/bsoFI                mwoI    tseI
                                          bamHI                         tseI  bstYI/xhoII  rsaI    csp6I sfaNI bsmAI  aciI    fnu4HI/
      bsmI                                alwI            mwoI  bbvI mboII accIII AGGCAGCAG AGTACACGAT GCGGAGACTG CGGAGACTG bbvI
3701 GGTGGTTGGC ATTCTGCTGG TCGTGTCTT GGGGGTGGTC TTTGGGATCC TCATCAAGCG ACGGCAGCAG AAGATCCGGA AGTACACGAT GCGGAGACTG CGGCCTCTGAC
     CCACCAACCG TAAGACGACC AGCACCAGAA CCCCCACCAG AAACCCTAGG AGTAGTTCGC TGCCGTCGTC TTCTAGGCCT TCATGTGCTA CGCCTCTGAC
658   V  V  G  I  L  L  V  V  V  L  G  V  V  F  G  I  L  I  K  R  R  Q  Q  K  I  R  K  Y  T  M  R  R  L
```

FIG. 7M

```
                                                        sau3AI
                                                        mboI/ndeII
                                              hinPI     dpnII
                                              hhaI/cfoI nlaIV
                                      scrFI             bstYI/xhoII
                                      mvaI              bamHI
                                      ecoRII            acil
                                      dsaV              sfaNI dpnI              esp3I     mnlI
                                      bstNI             mamI alwI               bsmBI     ddeI
                                      bssKI             bsaBI alwI              bsmAI alul hphI
                 rmaI                 apyI                                                
         mspAII/nspBII                
         acil    maeI                 
    mwoI fnu4HI/bsoFI acil            
psti nlaIV   bfaI    sfaNI
scfI bsgl
alul
801 CTGCAGGAAA CGGAGCTGGT GGAGCCGCTG ACACCTAGCC GAGCGATGCC CAACCAGGGG CAGATGCGGA TCCTGAAAGA GACGGAGCTG AGGAAGGTGA
    GACGTCCTTT GCCTCGACCA CCTCGGCGAC TGTGGATCGG CTCGCTACGG GTTGGTCCCC GTCTACGCCT AGGACTTTCT CTGCCTCGAC TCCTTCCACT
691  L  Q  E  T  E  L  V  E  P  L  T  P  S  G  E  A  M  P  N  Q  A  Q  M  R  I  L  K  E  T  E  L  R  K  V  R bslI
                          sau3AI
                          mboI/ndeII
                          dpnII
                          dpnI                                                    mscI/balI
                          alwI                                                    haeI
          sau3AI mwoI     nlaIV                                                   eaeI
          mboI/ndeII      bstYI/xhoII                                             tspRI
          dpnI hinPI      bamHI                                   tsp509I cfrI msII
          dpnI hhaI/cfoI          alwI                            apoI bsrI haeIII/palI     mnlI
          bstYI/xncII     accI    sfaNI
          alwI    haeII
901 AGGTGCTTGG ATCTGGCGCT TTTGGCACAG TCTACAAGGG CATCTGGATC CCTGATGGGG AGAATGTGAA AATTCCAGTG GCCATCAAAG TGTTGAGGGA
    TCCACGAACC TAGACCGCGA AAACCGTGTC AGATGTTCCC GTAGACCTAG GGACTACCCC TCTTACACTT TTAAGGTCAC CGGTAGTTTC ACAACTCCCT
725  V  L  G  S  G  A  F  G  T  V  Y  K  G  I  W  I  P  D  G  E  N  V  K  I  P  V  A  I  K  V  L  R  E nlaIV
                          hgiJII                                                 mwoI
                          bsp1286                                                bslI
          tail            bmyI                                                   acil
          maeII           banII    ndeI bsmAI bglI   sfaNI
    foki  ddeI  bsaAI
    bstF5I
001 AAACACATCC CCCAAAGCCA ACAAAGAAAT CTTAGACGAA GCATACGTGA TGGCTGGTGT GGGCTCCCCA TATGTCTCCC GCCTTCTGGG CATCTGCCTG
    TTTGTGTAGG GGGTTTCGGT TGTTTCTTTA GAATCTGCTT CGTATGCACT ACCGACCACA CCCGAGGGGT ATACAGAGGG CGGAAGACCC GTAGACGGAC
758  N  T  S  P  K  A  N  K  E  I  L  D  E  A  Y  V  M  A  G  V  G  S  P  Y  V  S  R  L  L  G  I  C  L
```

```
                                              mspI
                                              hpaII
                                              naeI/ngoMI
                                              cfr10I/bsrFI
                                         cac8I                                                                          haeIII/palI
                                         sgrAI                                            tsp45I                        sau96I
       pleI                         aciI  aciI hphI  mslI                                 maeIII    aluI                asuI       nlaIV                    bslI
       hinfI                                                                                                                                                
     bpmI/gsuI
4401 CTGGAGTCCA TTCTCCGCCG GCGGTTCACC CACCAGAGTG ATGTGTGGAG TTATGGTGTG ACTGTGTGGG AGCTGATGAC TTTTGGGGCC AAAACCTTACG
     GACCTCAGGT AAGAGGCGGC CGCCAAGTGG GTGGTCTCAC TACACACCTC AATACCACAC TGACACACCC TCGACTACTG AAAACCCCGG TTTGGAATGC
891  L  E  S  I  L  R  R  R  F  T  H  Q  S  D  V  W  S  Y  G  V  T  V  W  E  L  M  T  F  G  A  K  P  Y  D scrFI
                    nciI
                    mspI
                    hpaII
                    dsaV                                              tseI
                    cauII                                             mwoI
                    bssKI                                             fnu4HI/bsoFI
                  xmaI/pspAI                                          bbvI
            bslI  smaI                                                fnu4HI/bsoFI
          sau3AI  scrFI                                               aciI
         mboI/ndeII                                                   bsrBI                                               sau3AI
         dpnII   nciI                                                                                                     mboI/ndeII
         dpnI   dsaV    sau3AI                                                                                            dpnII
         alwI   cauII  mboI/ndeII                                                                                         dpnI
         nlaIV   bssKI  dpnII                                                                                              bclI
       bstYI/xhoII      dpnI                                                                                              nlaIII
         bamHI   bsaJI  alwI    bspMI                                                                     accI  mslI     nlaIII
         alwI   avaI  bstYI/xhoII                                                                                          
4501 ATGGGATCCC AGCCCGGGAG ATCCCTGACC TGCTGGAAAAA GGGGAGCGG CTGCCCCAGC CCCCCATCTG CACCATTGAT GTCTACATGA TCATGGTCAA
     TACCCTAGGG TCGGGCCCTC TAGGGACTGG ACGACCTTTT CCCCCTCGCC GACGGGGTCG GGGGGTAGAC GTGGTAACTA CAGATGTACT AGTACCAGTT
925  G  I  P  A  R  E  I  P  D  L  L  E  K  G  E  R  L  P  Q  P  P  I  C  T  I  D  V  Y  M  I  M  V  K

FIG. 7P
```

```
                                                                          sau96I
                                                                          sanDI
                                                                  scrFI
                                                                  mvaI nlaIV
                                                                  ecoRII
                                                                  dsaV avaII
                                         scrFI                    bstNI
                                         nciI                     bssKI
                                         mspI                     bsaJI
                                         hpaII                    apyI asuI
                                         dsaV                     haeIII/palI
                                         cauII                    mscI/balI
                                         bssKI                    haeI ppuMI              hinPI
                    haeIII/palI          bsII               tsp509I  eaeI nlaIV           hhaI/cfoI
            fokI    eaeI tfiI                               ecoRI    nlaIII eco0109I/draII haeII       bsII
            bstF5I  cfrI hinfI                              apoI     aciI cfrI bsmFI      afeI/eco47III bstF5I
    fokI    pleI    hinfI                                                                              fokI
    bstF5I                                                                                             
4601 ATGTTGGATG ATTGACTCTG AATGTCGGCC GAGTTGGTGT CTGAATTCTC CCGCATGGCC AGGGACCCCC AGCGCTTTGT GGTCATCCAG
     TACAACCTAC TAACTGAGAC TTACAGCCGG CTCAACCACA GACTTAAGAG GGCGTACCGG TCCCTGGGGG TCGCGAAACA CCAGTAGGTC
 958 C  W  M  I  D  S  E   C  R  P    R  E  L  V  S    E  F  S    R  M  A    R  D  P  Q    R  F  V  I  Q scrFI
                                                                          mvaI
                                                                          ecoRII
                                                                          dsaV
                                                                          bstNI
                                                                          bssKI
                                                                          apyI
                                                                          sexAI
                     sau96I                                               sau96I
                     haeIII/palI                                          avaII
                     asuI                                                 ppuMI
                     sau96I                                               nlaIV       sfaNIU
                     pspOMI/bsp120I                                       eco0109I/draII  mnlI
                     nlaIV                                                bsmFI asuI                 bseRI
                     hgiJII                                bsrBI          nlaIII asuI  bstF5I
                     bsp1286                   mnlI        aciI tspRI bpmI/gsuI       fokI ddeI
                     bmyI                                                             bstF5I
            mnlI     banII      bsmFI
                     asuI bstXI styI
                     apaI bsrI bsaJI
4701 AATGAGGACT TGGGCCCAGC CAGTCCCTTG GACAGCACCT TCTACCGCTC ACTGCTGGAG GACGATGACA TGGGGGACCT GGTGGATGCT GAGGAGTATC
     TTACTCCTGA ACCCGGGTCG GTCAGGGAAC CTGTCGTGGA AGATGGCGAG TGACGACCTC CTGCTACTGT ACCCCCTGGA CCACCTACGA CTCCTCATAG
 991 N  E  D  L  G  P  A  S  P  L    D  S  T  F  Y  R  S  L  L  E    D  D  D  M    G  D  L  V  D  A    E  E  Y  L

```
                                                                                                        sau96I
                                                                                                        avaII
                                                                                                        asuI
                                                                                 mnlI                   nlaIV
                                                                                 bseRI                  bsmFI
                         scrFI                                                   mnlI    eco57I         taqI    mnlI    bsrI
                         mvaI
                         ecoRII                                  tseI
                         dsaV                                    fnu4HI/bsoFI
                         bstNI                                   aluI
                         bssKi                          mnlI bbvI  ddeI
                rsaI     bsaJI     apyI                 bseRI
                csp6I    bsaJi     bslI
    avaI scaI
301 GTGGAGAACC CCGAGTACTT GACACCCCAG GGAGGAGCTG CCCCTCAGCC CCACCCTCCT CCTGCCTTCA GCCCAGCCTT CGACAACCTC TATTACTGGG
    CACCTCTTGG GGCTCATGAA CTGTGGGGTC CCTCCTCGAC GGGGAGTCGG GGTGGGAGGA GGACGGAAGT CGGGTCGGAA GCTGTTGGAG ATAATGACCC
191 V  E  N  P  E  Y  L  T  P  Q  G  G  A  P  Q  P  H  P  P  P  A  F  S  P  A  F  S  P  A  F  D  N  L  Y  Y  W  D scrFI
                                                                                          mvaI
                                                                                          ecoRII
                                                                                          dsaV
           sau96I                                                                         bstNI
           nlaIV                                                                          bssKi
           avaII                                                                          bslI
           asuI                  nlaIV                                                    bsaJI
           ppuMI                 hgiJII                                                   apyI
           eco01091/draII        bsp1286                                         rsaI              tailI   bsrI
    scrFI                        bmyI                                            csp6I    maeII   tspRI
    mvaI                         banII            bslI         bsmFI
    ecoRII
    dsaV
    bstNI
    bssKi
    apyI     bslI aciI
401 ACCAGGACCC ACCAGAGCGG GGGGCTCCAC CCAGCACCTT CAAAGGGACA CCTACGGCAG AGAACCCAGA GTACCTGGGT CTGCACGTGC CAGTGTGAAC
    TGGTCCTGGG TGGTCTCGCC CCCCGAGGTG GGTCGTGGAA GTTTCCCTGT GGATGCCGTC TCTTGGGTCT CATGGACCCA GACGTGCACG GTCACACTTG
225 Q  D  P  P  E  R  G  A  P  P  S  T  F  K  G  T  P  T  A  E  N  P  E  Y  L  G  L  D  V  P  V  Q
```

```
                                                           mspI
                                                           hpaII
                                                           scrFI
                                                           ncII
                                                           dsaV             mboII
                                                           cauII            sau3AI
                                                           bssKI            mboI/ndeII
                                                           bslI             dpnII
                                                    tseI   bslI             dpnI
                                                    fnu4HI/bsoFI            bstYI/xhoII
                                              mnlI  mboII  bbvI bsaJI bsrI  bglII        scfI          taqI
    rmaI
    maeI
    bfaI
    sau96I
    avaII
    asuI              fokI
    ppuMI    mnlI    bstF5I
    eco0109I/draII   sfaNI
701 AGGACCTAGA GGAAGGCATC CAAACGCTGA TGGGGAGGCT GGAAGATGGC AGCCCCCGGA CTGGGCAGAT CTTCAAGCAG ACCTACAGCA AGTTCGACAC
    TCCTGGATCT CCTTCCGTAG GTTTGCGACT ACCCCTCCGA CCTTCTACCG TCGGGGGCCT GACCCGTCTA GAAGTTCGTC TGGATGTCGT TCAAGCTGTG
                                            ^end of ex 4/ start ex 5

801 AAACTCACAC AACGATGACG CACTACTCAA GAACTACGGG CTGCTCTACT GCTTCAGGAA GGACATGGAC AAGGTCGAGA CATTCCTGCG CATCGTGCAG
    TTTGAGTGTG TTGCTACTGC GTGATGAGTT CTTGATGCCC GACGAGATGA CGAAGTCCTT CCTGTACCTG TTCCAGCTCT GTAAGGACGC GTAGCACGTC
```

```
                                                                                                            bsp1286
                                                                                              sau96I        bmyI
                                                                                              haeIII/palI   bsrI
                                                                                              asuI          bpmI/gsuI
                                                                                scrFI  scrFI                mslI tspRI
                                                                                mvaI   mvaI                 GCCACTCCAG
                                                                                ecoRII ecoRII               CGGTGAGGTC
                                                                                dsaV   dsaV
                                                                                bstNI  bstNI
                                                                                bssKI  bssKI
                                                                                bslI   apyI
                                            mslI        tspRI             bsrI  mnlI  apyI bsaJI CCTGGAAGTT
                                            fokI        mnlI              CTGTGACCC CTCTCCTGGC CCTGGAAGTT
                                            bstF5I tsp45I                 CTGTGACCTGC CTCTCCTGGC
                                            sfaNI  maeIII                 GACACTGGGG AGGGGTCACG GGACCTTCAA
                                                                          CCACCGTAGG ATCGACGGGC
                                            ^end of spe-sma pBK-CMV/hgh insert to replace intron
                                                           rmaI
                                                           maeI                                    ^TG PCR 3' primer
                                                           bfaI
                                            ahdI/eam1105I      sspI                 mnlI
        tru9I                TAGGTGTCCT TCTATAATAT TATGGGGTGG AGGGGGGTGG TATGGAGCAA
        mseI                 AAACAGACTG ATCCACAGGA AGATATTATA ATACCCCACC TCCCCCACC ATACCTCGTT
        tsp509I sfaNI
      TGCCCCACCAG CCTTGTCCTA ATAAAATTAA GTTGCATCAT TTTGTCTGAT
      ACGGGGTGGTC GGAACAGGAT TATTTTAATT CAACGTAGTA
        ^end of hgh exon5
```

FIG. 7X

```
                    scrFI
                    mval
                    ecoRII
                    ecoRII
                    dsaV
                    bstNI
                    bsSKI
                    apyI
                    haeIII/palI
                    mscI/balI
                    haeI                             sau3AI
              eaeI       bsmAI                       mboI/ndeII
         hphI   cfrI   bsaI           hphI  dpnII     dpnI    haeI    bstXI
                                                styI haeIII/palI                                                                tspRI
                              eaeI  bsmAI    ddeI  dpnI    bsaJI  mnlI  tsp509I
301 GGGGTTTCAC CATATTGGCC AGGTGGTCT CCAACTCCTA ATCTCAGGTG ATCTACCCAC CTTGGCCTCC CAAATTGCTG GGATTACAGG CGTGAACCAC
    CCCCAAAGTG GTATAACCGG TCCGACCAGA GGTTGAGGAT TAGAGTCCAC TAGATGGGTG GAACCGGAGG GTTTAACGAC CCTAATGTCC GCACTTGGTG
                                                                                                                   mspI
                                                                                                                   cfr10I/bsrFI
                                                                                                                   bsaWI
                                                          taiI                        styI sau96I hpaII
                                                          hinfI/acyI                  ncoI haeIII/palI
                                                          ahaII/bsaHI                 dsaI asuI ageI
                              tru9I                       aatII                       bsaJI  pflMI
                              mseI                                                    bspMI  nlaIII  bslI        bsmFI
                              ahaIII/draI  bslI  mnlI  maeII
401 TGCTCCCCTTC CCTGTCCTTC TGATTTTAAA ATAACTATAC CAGCAGGAGG ACGTCCAGAC ACAGGATAGG CTACCTGCCA TGGCCCAACC GGTGGGACCAT
    ACGAGGGGAAG GGACAGGAAG ACTAAAATTT TATTGATATG GTCGTCCTCC TGCAGGTCTG TGTCGTATCC GATGGACGGT ACCGGGTTGG CCACCCTGTA hgiAI/aspHI
                                                      sau3AI
                                                      mboI/ndeII       tru9I
                                                      dpnII bsp1286
                                                      dpnI  bsiHKAI                      tsp509I
                                                      pvuI/bspCI       mseI              nlaIII
                                   sau96I                       bmyI   aseI/asnI/vspI
                                   avaII                        bsiEI  apaLI/snoI  rcaI  apoI
              mwoI                 asuI       ddeI       sfaNI          alw44I/snoI  bspHI  tsp509I
              cac8I  tspRI  mnlI  nlaIII  nlaIV
501 TTGAGTTGCT TGCTTGGCAC TGTCCTCTCA TGCGTTGGGT CCACTCAGTA GATGCCTGTT GAATTACGAT CGGTGCACAT TAATTCATGA AATTCGTAAT
    AACTCAACGA ACGAACCGTG ACAGGAGAGT ACGCAACCCA GGTGAGTCAT CTACGGACAA CTTAATGCTA GCCACGTGTA ATTAAGTACT TTAAGCATTA
                                                              ^start of linker 2                           ^end of linker 2
```

FIG. 7Y

```
                                                                                              scrFI
                                                                                              mvaI
                                                                                              ecoRII
                                                                                              dsaV nlaIV
                                                                                              bstNI
                                                                                              bssKI
                                                                                              bsaJI
                                                                             mspI             apyI hgiCI
                         bsrBI                                               hpaII            mwoI banI
           tsp509I       aciI          tsp509I
    nlaIII aluI
601 CATGGTCATA GCTGTTTCCT GTGTGAAATT GTTATCCGCT CACAATTCCA CACAACATAC GAGCCGGAAG CATAAAGTGT AAAGCCTGGG GTGCCTAATG
    CTACCAGTAT CGACAAAGGA CACACTTTAA CAATAGGCGA GTGTTAAGGT GTGTTGTATG CTCGGCCTTC GTATTTCACA TTTCGGACCC CACGGATTAC aciI
                                                                                                         thaI
                                                                                                         fnuDII/mvnI
                                                                                                         bstUI
                                                                                                         bsh1236I
                                                                                                         hinPI
                                                                                                         hhaI/cfoI
                                                                              eaeI           thaI
                                                                aluI   tru9I  cfrI           fnuDII/mvnI
            tsp509I     mwoI                                    pvuII   mseI  tfiI haeIII/palI
            tru9I       hinPI                                   mspAII/nspBI  hinfI bslI bstUI
            mseI        hhaI/cfoI cac8I                         cac8I         aseI/asnI/vspI bsh1236I
    maeIII  aseI/asnI/vspI        tspRI aciI      bsrI
    mnlI                                          CGGGAAACCT GTCGTGCCAG CTGGATTAAT GAATCGGCCA ACGGCGGGG
701 AGTGAGGTAA CTCACATTAA TTGCGTTGCG CTCACTGCCC GCTTTCCAGT CGGGAAACCT GTCGTGCCAG CTGGATTAAT GAATCGGCCA ACGGCGGGG
    TCACTCCATT GAGTGTAATT AACGCAACGC GAGTGACGGG CGAAAGGTCA GCCCTTTGGA CAGCACGGTC GACCTAATTA CTTAGCCGGT TGCGCGCCCC mwoI
                 earI/ksp632I                        fnu4HI/bsoFI
                 sapI                  jinPI         aciI  aciI
                 hinPI   aciI          hhaI/cfoI     tseI  bsrBI
                 hhaI/cfoI             pleI  tseI    fnu4HI/bsoFI
         mwoI            mnlI          hinfI fnu4HI/bsoFI
    aciI         haeII mboII           bbvI         bsiEI      bbvI  cac8I       aluI        aciI
    mnlI                                          tspRI
801 AGAGGCGGTT TGGGTATTGG GCGCTCTTCC GCTTCCTCGC GCTCGGCTCG GTCGGCGAGC TGCGGGCGAG GGTATCAGCT CACTCAAAGG
    TCTCCGCCAA ACGCATAACC CGCGAGAAGG CGAAGGAGCG AGTGACTGAG CAGCAAGCCG ACGCCGCTCG CCATAGTCGA GTGAGTTTCC
```

```
                                        tru9I
                                        tsp509I
          tru9I                          tru9I                                                           nlaIV
          msel msel                      msel                                              tru9I        hgiCI
          ahaIII/draI                    ahaIII/draI                         maeIII        msel tspRI banI            ddeI
701 CTTTAAATT AAAAATGAAG TTTTAAATCA ATCTAAAGTA TATATGAGTA AACTTGGTCT GACAGTTACC AATGCTTAAT CAGTGAGGCA CCTATCTCAG
    GAAAATTTAA TTTTTACTTC AAAATTTAGT TAGATTCAT ATATACTCAT TTGAACCAGA CTGTCAATGG TTACGAATTA GTCACTCCGT GGATAGAGTC bsrI tseI
    sau3AI                                pleI                                                    sau96I fnu4HI/bsoFI
    mboI/ndeII                            hinfI                                                   nlaIV  bbvI
    dpnII       foKI                      ahdI/eamll05I                            mnlI           haeIII/paII
    dpnI        bstF5I                                                                            asuI tspRI   bsrDI
801 CGATCTGTCT ATTTCGTTCA TCCATAGTTG CCTGCTCCC CGTCCTGTAG ATAACTACGA TACGGGAGGG CTTACCATCT GGCCCCAGTG CTGCAATGAT
    GCTAGACAGA TAAAGCAAGT AGGTATCAAC GGACTGAGGG GCAGGACATC TATTGATGCT ATGCCCTCCC GAATGGTAGA CCGGGGTCAC GACGTTACTA bsmAI
    bsaI
    thaI                                                         mspI                                            fokI
    fnuDII/mvnI         mspI bpmI/gsuI                            mwoI    haeIII/paII         sau96I              mnlI
    bstUI               hpaII                                     bglI    sau96I hinPI        avaII              acII   bstF5I
    bsh1236I            cfr10I/bsrFI                              cac8I hpaII asuI  hhaI/cfoI asuI               acII   bstF5I
    acII       hphI    nlaIV
901 ACCGGAGAC CCACGCTCAC CGGCTCCAGA TTTATCAGCA ATAAACCAGC CAGCCGGAAG GGCCGAGCGC AGAAGTGGTC CTGCAACTTT ATCCGCCTCC
    TGGCCGCTCTG GGTGCGAGTG GCCGAGGAGT CGCCGGAGTG AAATAGTCGT TATTTGGTCG GTCGGCCTTC CCGGCTCCGG TCTTCACCAG GACGTTGAAA TAGGCGGAGG scrFI
                        ncII                                               taII
                        mspI                                               psp1406I maeII                tseI     msII
               tsp509I  dsaV       rmaI                              hinPI maeII                          fnu4HI/bsoFI
               tru9I    cauII     maeI                     tru9I     hhaI/cfoI                  bsrDI cac8I     sfaNI       tsp45I
               msel     bssKI     bfaI                     msel      mstI acII                  mwoI bbvI                  maeIII
    bsrI aseI/asnI/vspI alu I     bsrI                               aviII/fspI                                tsp45I
001 ATCCAGTCTA TTAATTGTTG CCGGGAAGCT AGAGTAAGTA GTTCCAACGT TAATAGTTTG CGCAACGTTG TGCCATTGC TGCTGGGCATC GTGTGTCAC
    TAGGTCAGAT AATTAACAAC GGCCCTTCGA TCTCATTCAT CAAGGGTCA ATTATCAAAC GGTTGCAAC ACGGTTGCAAC ACGACCGTAG CACACAGTG
```

```
     hgiAI/aspHI
     bsp1286
     bsiHKAI              eco57I
     bmyI                 mboII
     apaLI/snoI           sau3AI
     alw44IsnoI           mboI/ndeII                                                                         acII
     bssSI                dpnII    sfaNI              hphI                    hphI                           fnu4HI/bsoFI
501 CACTCGTGCA CCCAACTGAT CTTCAGCATC TTTTACTTTC ACCAGCGTTT CTGGGTGAGC AAAAACAGGA AGGCAAAATG CCGCAAAAA GGGAATAAGG
    GTGAGCACGT GGGTTGACTA GAAGTCGTAG AAAATGAAAG TGGTCGCAAA GACCCACTCG TTTTTGTCCT TCCGTTTTAC GGCGTTTTT CCCTTATTCC
                                                                                      nlaIII
                                                                                      rcaI      bclVI
                                                                                      bspHI aclI
                                             mboII                                    bsmAI bsrBI
    msII             earI/ksp6321         sspI
601 GCGACACGGA AATGTTGAAT ACTCATACTC TTCCTTTTTC AATATTATTG AAGCATTAT CAGGGTTATT GTCTCATGAG CGGATACATA TTTGAATGTA
    CGCTGTGCCT TTACAACTTA TGAGTATGAG AAGGAAAAAG TTATAATAAC TTCGTAATA GTCCCAATAA CAGAGTACTC GCCTATGTAT AAACTTACAT
                                                                         talI
                  hinPI                                                  maeII
                  thaI                                                   hinlI/acyI              nlaIII
                  fnuDII/mvnI                                            ahaII/bsaHI            rcaI      tru9I
                  bstUI                                                  aatII ddeI             bspHI     mseI
                  bsh1236I
                  acII
              nnaIV hhaI/cfoI
701 TTTAGAAAA TAAACAAATA GGGGTTCCGC GCACATTTCC CCGAAAAGTG CCACCTGACG TCTAAGAAAC CATTATTATC ATGACATTAA CCTATAAAA
    AAATCTTTT ATTGTTTAT CCCCAAGGCG CGTGTAAAGG GGCTTTTCAC GGTGGACTGC AGATTCTTTG GTAATAATAG TACTGTAATT GGATATTTT
                                                                                                                     mspI
                                                                                                                     scrFI
                                                                                                                     ncII esp3I
                                                                                                                     dsaV bsmBI
                                                            thaI                                                     tseI cauII
                                                            fnuDII/mvnI                                              fnu4HI/bsoFI
                                                            bsh1236I                                                 bssKI
                                                            hinPI                                                    nlaIII
        sau961  mboII                                       thaI                                                     nspHI aluI hpaII      tsp45I
        haeIII/palI                                         fnuDII/mvnI                                              nspI bbvI bsII bsmAI maeIII
        ecoO109I/draII                                      bstUI
     mnII       bpuAI                                       bsh1236I
     bssSI asuI bbsI                      mnII hhaI/cfoI hphI           hphI    mnII
801 TAGGCGTATC ACGAGGCCCT TTCGTCTTCA AGAATACTGC CTCGGCCGTT TCGGTGATGA CGGTGAAAAC CTCTGACACA TGCAGCTCCC GGAGACGGTC
    ATCCGCATAG TGCTCCGGGA AGCAGAAGT TCTTATGACG GAGCCGGCAA AGCCACTACT GCCACTTTTG GAGACTGTGT ACGTCGAGGG CCTCTGCCAG
```

```
                                      scrFI
                                      mvaI
                                      ecoRII
                                      dsaV
                                      bstNI
                                      bssKI                                          tspRI
                                      bsaJI              tsp45I                      bsrI
    tseI                              apyI               maeIII         taII         haeIII/paII
    fnu4HI/bsoFI tru9I                                   bsrI  maeII                 eaeI
    bbvI     mseI     maeIII                                                         cfrI
201 GTGCTGCAAG GCGATTAAGT TGGGTAACGC CAGGGTTTTC CCAGTCACGA CGTTGTAAAA CGACGGCCAG TGCC
    CACGACGTTC CGCTAATTCA ACCCATTGCG GTCCCAAAAG GGTCAGTGCT GCAACATTTT GCTGCCGGTC ACGG
```

*FIG. 7GG* ns of Treatment Using
Anti-ErbB Antibody-Maytansinoid
Conjugates

CROSS REFERENCE TO RELATED APPLICATIONS

This application claims priority to U.S. Provisional Application Nos. 60/238,327, filed Oct. 5, 2000, 60/189,844 filed Mar. 16, 2000, and 60/327,563 filed Jun. 23, 2000 under 35 USC §119(e) and is a continuation of U.S. application Ser. No. 09/811,123 filed Mar. 16, 2001 now U.S. Pat. No. 7,097, 840, from which priority is claimed under 35 USC §120; all of which applications are hereby incorporated by reference in their entireties.

BACKGROUND OF THE INVENTION

1. Field of the Invention

The present invention concerns methods of treatment, especially ErbB receptor-directed cancer therapies, using anti-ErbB receptor antibody-maytansinoid conjugates, and articles of manufacture suitable for use in such methods.

2. Description of the Related Art

1. Maytansine and Maytansinoids

Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and maytansinol analogues are disclosed, for example, in U.S. Pat. Nos. 4,137, 230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansine and maytansinoids are highly cytotoxic but their clinical use in cancer therapy has been greatly limited by their severe systemic side-effects primarily attributed to their poor selectivity for tumors. Clinical trials with maytansine had been discontinued due to serious adverse effects on the central nervous system and gastrointestinal system (Issel et al., *Can. Trtmnt. Rev.* 5:199-207 [1978]).

2. The ErbB Family of Receptor Tyrosine Kinases and Anti-ErbB Antibodies

Members of the ErbB family of receptor tyrosine kinases are important mediators of cell growth, differentiation and survival. The receptor family includes four distinct members, including epidermal growth factor receptor (EGFR or ErbB1), HER2 (ErbB2 or p185$^{neu}$), HER3 (ErbB3) and HER4 (ErbB4 or tyro2).

p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homologue of neu is observed in breast and ovarian cancers and correlates with a poor prognosis (Slamon et al., *Science,* 235:177-182 (1987); Slamon et al., *Science,* 244:707-712 (1989); and U.S. Pat. No. 4,968,603). To date, no point mutation analogous to that in the neu proto-oncogene has been reported for human tumors. Overexpression of ErbB2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science,* 229:974 (1985); Yokota et al., *Lancet:* 1:765-767 (1986); Fukushigi et al., *Mol Cell Biol.,* 6:955-958 (1986); Geurin et al., *Oncogene Res.,* 3:21-31 (1988); Cohen et al., *Oncogene,* 4:81-88 (1989); Yonemura et al., *Cancer Res.,* 51:1034 (1991); Borst et al., *Gynecol. Oncol.,* 38:364 (1990); Weiner et al., *Cancer Res.,* 50:421-425 (1990); Kern et al., *Cancer Res.,* 50:5184 (1990); Park et al., *Cancer Res.,* 49:6605 (1989); Zhau et al., *Mol. Carcinog.,* 3:354-357 (1990); Aasland et al. *Br. J. Cancer* 57:358-363 (1988); Williams et al. *Pathobiology* 59:46-52 (1991); and McCann et al., *Cancer,* 65:88-92 (1990). ErbB2 may be overexpressed in prostate cancer (Gu et al. *Cancer Lett.* 99:185-9 (1996); Ross et al. *Hum. Pathol.* 28:827-33 (1997); Ross et al. *Cancer* 79:2162-70 (1997); and Sadasivan et al. *J. Urol.* 150:126-31 (1993)).

A spliced form of erbB2 oncogen encoding a constitutively tyrosine phosphorylated ErbB2 receptor is disclosed in PCT publication WO 00/20579, published on Apr. 13, 2000. The erbB2 protein encoded by the splice variant has an in frame deletion of 16 amino acids (CVDLDDKGCPAEQRAS (SEQ ID NO: 11)), two of which are conserved cysteine residues.

Antibodies directed against the rat p185$^{neu}$ and human ErbB2 protein products have been described. Drebin and colleagues have raised antibodies against the rat neu gene product, p185$^{neu}$. See, for example, Drebin et al., *Cell* 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of p185$^{neu}$ result in synergistic anti-tumor effects on neu-transformed NIH-3T3 cells implanted into nude mice. See also U.S. Pat. No. 5,824,311 issued Oct. 20, 1998.

Other anti-ErbB2 antibodies with various properties have been described in Tagliabue et al. Int. *J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS (USA)* 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373 (1994); Arteaga et al. *Cancer Res.* 54:3758-3765 (1994); Harwerth et al. *J. Biol. Chem.* 267:15160-15167 (1992); U.S. Pat. No. 5,783,186; and Klapper et al. *Oncogene* 14:2099-2109 (1997).

Hudziak et al., *Mol. Cell. Biol.* 9(3): 1165-1172 (1989) describe the generation of a panel of anti-ErbB2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-α. See also U.S. Pat. No. 5,677,171 issued Oct. 14, 1997. The anti-ErbB2 antibodies discussed in Hudziak et al. are further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2):979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

The murine monoclonal anti-HER2 antibody inhibits the growth of breast cancer cell lines that overexpress HER2 at the 2+ and 3+ level, but has no activity on cells that express lower levels of HER2 (Lewis et al., *Cancer Immunol. Immunother.* [1993]). Based on this observation, antibody 4D5 was humanized (Carter et al., *Proc. Natl. Acad. Sci. USA* 89: 4285-4289 [1992]). The humanized version designated HERCEPTIN® (huMAb4D5-8, rhuMAb HER2, U.S. Pat. No. 5,821,337) was tested in breast cancer patients whose tumors overexpress HER2 but who had progressed after conventional chemotherapy (Baselga et al., *J. Clin. Oncol.* 14:737-744 [1996]); Cobleigh et al., *J. Clin. Oncol.* 17: 2639-2648 [1999]). Most patients in this trial expressed HER2 at the 3+ level, though a fraction was 2+ tumors. Remarkably, HERCEPTIN® induced clinical responses in 15% of patients (complete responses in 4% of patients, and partial responses in 11%) and the median duration of those responses was 9.1 months. HERCEPTIN® received marketing approval from the Food and Drug Administration Sep. 25, 1998 for the treatment of patients with metastatic breast cancer whose tumors overexpress the ErbB2 protein.

Homology screening has resulted in the identification of two other ErbB receptor family members; ErbB3 (U.S. Pat. Nos. 5,183,884 and 5,480,968 as well as Kraus et al. *PNAS (USA)* 86:9193-9197 (1989)) and ErbB4 (EP Pat Appln No 599,274; Plowman et al., *Proc. Natl. Acad. Sci. USA,* 90:1746-1750 (1993); and Plowman et al., *Nature,* 366:473-475 (1993)). Both of these receptors display increased expression on at least some breast cancer cell lines.

3. Maytansinoid-Antibody Conjugates

In an attempt to improve their therapeutic index, maytansine and maytansinoids have been conjugated to antibodies specifically binding to tumor cell antigens. Immunoconjugates containing maytansinoids are disclosed, for example, in U.S. Pat. Nos. 5,208,020; 5,416,064 and European Patent EP 0 425 235 B1, the disclosures of which are hereby expressly incorporated by reference. Liu et al, *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al. *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×10$^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Although HERCEPTIN® is a breakthrough in treating patients with ErbB2-overexpressing breast cancers that have received extensive prior anti-cancer therapy, generally approximately 85% of the patients in this population fail to respond, or respond only poorly, to HERCEPTIN® treatment, and in the clinical trial preceding marketing approval, the median time to disease progression in all treated patients was only 3.1 months. Therefore, there is a significant clinical need for developing further HER2-directed cancer therapies for those patients with HER2-overexpressing tumors or other diseases associated with HER2 expression that do not respond, or respond poorly, to HERCEPTIN® treatment.

SUMMARY OF THE INVENTION

The present invention is based on the unexpected experimental finding that HERCEPTIN®-maytansinoid conjugates are highly effective in the treatment of HER2 (ErbB2) overexpressing tumors that do not respond, or respond poorly, to HERCEPTIN® therapy. The anti-ErbB2-maytansinoid conjugates of the present invention are expected to have superior clinical activity compared to treatment with HERCEPTIN® alone, including a better objective response rate and/or longer duration of response and/or increased survival.

In one aspect, the present invention concerns a method for the treatment of a tumor in a mammal, wherein the tumor is characterized by the overexpression of an ErbB receptor and does not respond or responds poorly to treatment with a monoclonal anti-ErbB antibody, comprising administering to the mammal a therapeutically effective amount of a conjugate of the anti-ErbB antibody with a maytansinoid.

In a preferred embodiment, the patient is human. In another preferred embodiment, the ErbB receptor is (human) ErbB2 (HER2). The method is not limited by the mechanism of action of the anti-ErbB antibody used. Thus, the anti-ErbB antibody may, for example, have growth inhibitory properties and/or may induce cell death and/or apoptosis. In a particularly preferred embodiment, the method concerns the treatment of cancer including, without limitation, breast, ovarian, stomach, endometrial, salivary gland, lung, kidney, colon, colorectal, thyroid, pancreatic, prostate and bladder cancer. Preferably the cancer is breast cancer, in particular, breast cancer which overexpresses ErbB2 at a 2+ level or above, more preferably at a 3+ level. A preferred group of antibodies has a biological characteristic of a 4D5 monoclonal antibody, or binds essentially the same epitope as a 4D5 monoclonal antibody, a humanized form of the murine monoclonal antibody 4D5 (ATCC CRL 10463) being particularly preferred.

The maytansinoid used in the conjugates of the present invention may be maytansine or, preferably, maytansinol or a maytansinol ester. The antibody and maytansinoid may be conjugated by a bispecific chemical linker, such as N-succinimidyl-4-(2-pyridylthio)propanoate (SPDP) or N-succinimidyl-4-(2-pyridylthio)pentanoate (SPP). The linking group between the antibody and the maytansinoid may, for example, be a disulfide, thioether, acid labile, photolabile, peptidase labile, or esterase labile group.

In another aspect, the invention concerns an article of manufacture comprising a container and a composition contained therein, wherein the composition comprises an anti-ErbB antibody-maytansinoid conjugate, and further comprising a package insert or label indicating that the composition can be used to treat cancer characterized by overexpression of an ErbB receptor, preferably at a 2+ level or above.

BRIEF DESCRIPTION OF THE DRAWINGS

FIG. 1 shows the heavy chain variable region sequence of a humanized anti-HER2 antibody 2C4 (SEQ ID NO: 1) aligned with the heavy chain variable region sequences of antibody 574 (SEQ ID NO: 2) and the human subgroup V$_H$III upon which the humanized sequences are based (SEQ ID NO: 3).

FIG. 2 shows the light chain variable region sequence of a humanized anti-HER2 antibody 2C4 (SEQ ID NO: 4) aligned with the light chain variable region sequences of antibody 574 (SEQ ID NO: 5) and the sequence of the human subgroup upon which the humanized sequences are based (SEQ ID NO: 6).

FIGS. 7A-GG shows the nucleotide sequence of a HER2 transgene plasmid construct (SEQ ID NO: 7) directing the expression of native human HER2 (ErbB2) in the mammary gland of a transgenic mouse. The reverse strand is also depicted (SEQ ID NO: 10). The figure includes the nucleotide sequence of HER2 (ErbB2) cDNA insert (SEQ ID NO: 8) as well as the deduced amino acid sequence of HER2 (ErbB2) (SEQ ID NO: 9), including the signal sequence. Within SEQ ID NO: 9, residues from about 22 to about 645, inclusive represent the HER2 (ErbB2) extracellular domain.

DETAILED DESCRIPTION OF THE INVENTION

1. Definitions

Figure 3:
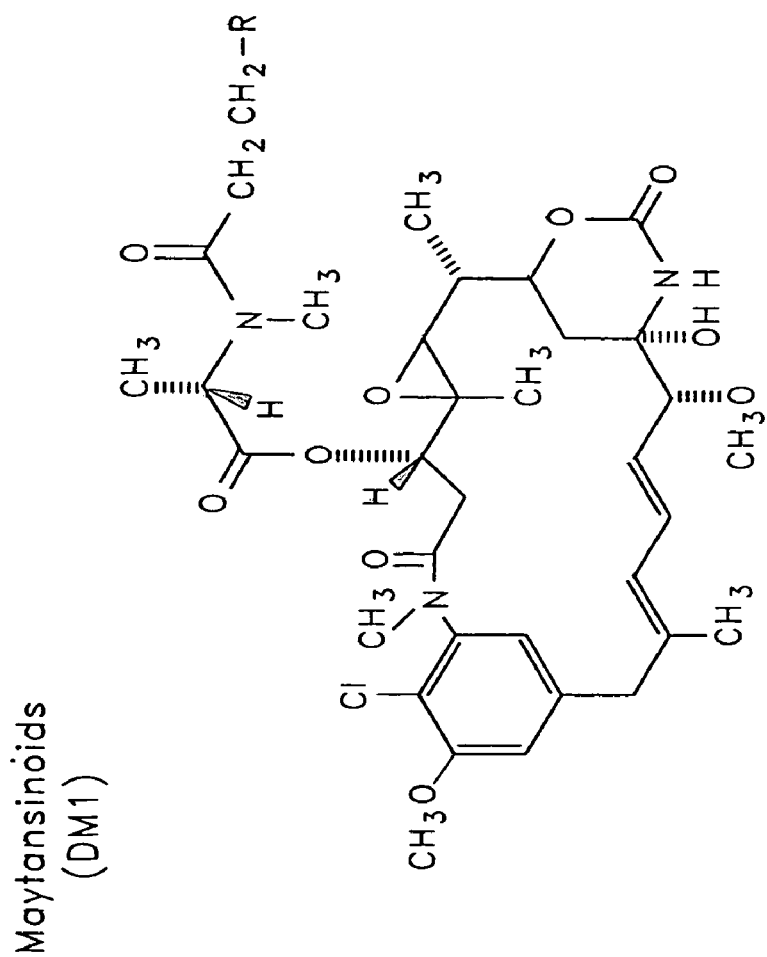
FIG. 3 shows the structure of the maytansinoid, designated "DM1." In the structure of DM1, "R" can be occupied by a variety of groups capable of forming a chemical bond with a selected linker. Preferably, "R" is an SH group or a protected derivative thereof, which forms an S—S bond with a linker, such as N-succinimidyl-4-(2-pyridylthio)pentanoate (SPP).

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994). One skilled in the art will recognize many methods and materials similar or equivalent to those described herein, which could be used in the practice of the present invention. Indeed, the present invention is in no way limited to the methods and materials described. For purposes of the present invention, the following terms are defined below.

An "ErbB receptor" or "ErbB" is a receptor protein tyrosine kinase which belongs to the ErbB receptor family and includes ErbB1 (EGFR), ErbB2 (HER2), ErbB3 (HER3) and ErbB4 (HER4) receptors and other members of this family to be identified in the future. The definition specifically includes ErbB receptors encoded by spliced forms of the corresponding erbB oncogens, including, without limitation, the deletion variant of ErbB2 disclosed in PCT publication No. WO 00/20579 (published on Apr. 13, 2000). The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a "native sequence" ErbB receptor or a functional derivative, such as an "amino acid sequence variant" thereof. Preferably the ErbB receptor is native sequence human ErbB receptor.

The terms "ErbB1", "epidermal growth factor receptor" and "EGFR" are used interchangeably herein and refer to native sequence EGFR as disclosed, for example, in Carpenter et al. *Ann. Rev. Biochem.* 56:881-914 (1987), including naturally occurring mutant forms thereof (e.g. a deletion mutant EGFR as in Humphrey et al. *PNAS (USA)* 87:4207-4211 (1990)), and its functional derivatives, such as amino acid sequence variants. erbB1 refers to the gene encoding the EGFR protein product.

The expressions "ErbB2" and "HER2" are used interchangeably herein and refer to native sequence human HER2 protein described, for example, in Semba et al., *PNAS (USA)* 82:6497-6501 (1985) and Yamamoto et al. *Nature* 319:230-234 (1986) (Genebank accession number X03363), and functional derivatives, such as amino acid sequence variants thereof. The term erbB2 refers to the gene encoding human HER2 and neu refers to the gene encoding rat $p185^{neu}$. Preferred HER2 is native sequence human HER2. Examples of antibodies which bind HER2 include MAbs 4D5 (ATCC CRL 10463), 2C4 (ATCC HB-12697), 7F3 (ATCC HB-12216), and 7C2 (ATCC HB 12215) (see, U.S. Pat. No. 5,772,997; WO98/77797; and U.S. Pat. No. 5,840,525, expressly incorporated herein by reference). Humanized anti-HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as described in Table 3 of U.S. Pat. No. 5,821,337 expressly incorporated herein by reference; humanized 520C9 (WO93/21319). Human anti-HER2 antibodies are described in U.S. Pat. No. 5,772,997 issued Jun. 30, 1998 and WO 97/00271 published Jan. 3, 1997.

"ErbB3" and "HER3" refer to the receptor polypeptide as disclosed, for example, in U.S. Pat. Nos. 5,183,884 and 5,480,968 as well as Kraus et al. *PNAS (USA)* 86:9193-9197 (1989), and functional derivatives, including amino acid sequence variants thereof. Examples of antibodies which bind HER3 are described in U.S. Pat. No. 5,968,511 (Akita and Sliwkowski), e.g. the 8B8 antibody (ATCC HB 12070) or a humanized variant thereof.

The terms "ErbB4" and "HER4" herein refer to the receptor polypeptide as disclosed, for example, in EP Pat Appln No 599,274; Plowman et al., *Proc. Natl. Acad. Sci. USA*, 90:1746-1750 (1993); and Plowman et al., *Nature*, 366:473-475 (1993), and functional derivatives, including amino acid sequence variants thereof such as the HER4 isoforms disclosed in WO 99/19488.

A "native" or "native sequence" EGFR, HER2, HER3 or HER4 polypeptide may be isolated from nature, produced by techniques of recombinant DNA technology, chemically synthesized, or produced by any combinations of these or similar methods.

"Functional derivatives" include amino acid sequence variants, and covalent derivatives of the native polypeptides as long as they retain a qualitative biological activity of the corresponding native polypeptide. Amino acid sequence variants generally differ from a native sequence in the substitution, deletion and/or insertion of one or more amino acids anywhere within a native amino acid sequence. Deletional variants include fragments of the native polypeptides, and variants having N- and/or C-terminal truncations. Ordinarily, amino acid sequence variants will possess at least about 70% homology, preferably at least about 80%, more preferably at least about 90% homology with a native polypeptide.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

By "ErbB ligand" is meant a polypeptide which binds to and/or activates an ErbB receptor. The ErbB ligand of particular interest herein is a native sequence human ErbB ligand such as Epidermal Growth Factor (EGF) (Savage et al., *J. Biol. Chem.* 247:7612-7621 (1972)); Transforming Growth Factor alpha (TGF-alpha) (Marquardt et al., *Science* 223: 1079-1082 (1984)); amphiregulin also known as schwanoma or keratinocyte autocrine growth factor (Shoyab et al. *Science* 243:1074-1076 (1989); Kimura et al. *Nature* 348:257-260 (1990); and Cook et al. *Mol. Cell. Biol.* 11:2547-2557 (1991)); betacellulin (Shing et al., *Science* 259:1604-1607 (1993); and Sasada et al. Biochem. *Biophys. Res. Commun.* 190:1173 (1993)); heparin-binding epidermal growth factor (HB-EGF) (Higashiyama et al., *Science* 251:936-939 (1991)); epiregulin (Toyoda et al., *J. Biol. Chem.* 270:7495-7500 (1995); and Komurasaki et al. *Oncogene* 15:2841-2848 (1997)), a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); or cripto (CR-1) (Kannan et al. *J. Biol. Chem.* 272 (6):3330-3335 (1997)). ErbB ligands which bind EGFR include EGF, TGF-alpha, amphiregulin, betacellulin, HB-EGF and epiregulin. ErbB ligands which bind HER3 include heregulins. ErbB ligands capable of binding HER4 include betacellulin, epiregulin, HB-EGF, NRG-2, NRG-3 and heregulins.

"Heregulin" (HRG) when used herein refers to a polypeptide which activates the ErbB2-ErbB3 and ErbB2-ErbB4 protein complexes (i.e. induces phosphorylation of tyrosine residues in the complex upon binding thereto). Various heregulin polypeptides encompassed by this term are disclosed in Holmes et al., *Science* 256:1205-1210 (1992); WO 92/20798; Wen et al., *Mol. Cell. Biol.* 14(3):1909-1919 (1994) and Marchionni et al., *Nature* 362:312-318 (1993), for example. The term includes biologically active fragments and/or variants of a naturally occurring HRG polypeptide, such as an EGF-like domain fragment thereof (e.g. $HRG\beta_{177\text{-}244}$).

An "ErbB hetero-oligomer" herein is a noncovalently associated oligomer comprising at least two different ErbB receptors. Such complexes may form when a cell expressing two or more ErbB receptors is exposed to an ErbB ligand and can be isolated by immunoprecipitation and analyzed by SDS-PAGE as described in Sliwkowski et al., *J. Biol. Chem.*, 269(20):14661-14665 (1994), for example. Examples of such ErbB hetero-oligomers include EGFR-HER2, HER2-HER3 and HER3—HER4 complexes. Moreover, the ErbB hetero-oligomer may comprise two or more HER2 receptors combined with a different ErbB receptor, such as HER3, HER4 or EGFR. Other proteins, such as a cytokine receptor subunit (e.g. gp130), may be included in the hetero-oligomer.

In the context of HER2 variants, such as HER2 fragments, the phrase "having the biological activity of a native human HER2" is used to refer to the qualitative ability of such fragments to induce tumor growth when overexpressed in an animal model (transgenic or non-transgenic) of the present invention.

"Tumor", as used herein, refers to all neoplastic cell growth and proliferation, whether malignant or benign, and all precancerous and cancerous cells and tissues.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A cancer which "overexpresses" an ErbB receptor is one which has significantly higher levels of an ErbB receptor, such as HER2, at the cell surface thereof, compared to a noncancerous cell of the same tissue type. Such overexpression may be caused by gene amplification or by increased transcription or translation. ErbB receptor overexpression may be determined in a diagnostic or prognostic assay by evaluating increased levels of the ErbB protein present on the surface of a cell (e.g. via an immunohistochemistry assay; IHC). Alternatively, or additionally, one may measure levels of ErbB-encoding nucleic acid in the cell, e.g. via fluorescent in situ hybridization (FISH; see WO98/45479 published October, 1998), Southern blotting, or polymerase chain reaction (PCR) techniques, such as real time quantitative PCR (RT-PCR). One may also study ErbB receptor overexpression by measuring shed antigen (e.g., ErbB extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

The tumors overexpressing HER2 are rated by immunohistochemical scores corresponding to the number of copies of HER2 molecules expressed per cell, and can been determined biochemically: 0=0–10,000 copies/cell, 1+=at least about 200,000 copies/cell, 2+=at least about 500,000 copies/cell, 3+=at least about 2,000,000 copies/cell. Overexpression of HER2 at the 3+ level, which leads to ligand-independent activation of the tyrosine kinase (Hudziak et al., *Proc. Natl. Acad. Sci. USA* 84: 7159-7163 [1987]), occurs in approximately 30% of breast cancers, and in these patients, relapse-free survival and overall survival are diminished (Slamon et al., *Science* 244: 707-712 [1989]; Slamon et al., *Science* 235: 177-182 [1987]).

Conversely, a cancer which is "not characterized by overexpression of an ErbB receptor" is one which, in a diagnostic assay, does not express higher than normal levels of ErbB receptor compared to a noncancerous cell of the same tissue type.

A "hormone independent" cancer is one in which proliferation thereof is not dependent on the presence of a hormone which binds to a receptor expressed by cells in the cancer. Such cancers do not undergo clinical regression upon administration of pharmacological or surgical strategies that reduce the hormone concentration in or near the tumor. Examples of hormone independent cancers include androgen independent prostate cancer, estrogen independent breast cancer, endometrial cancer and ovarian cancer. Such cancers may begin as hormone dependent tumors and progress from a hormone-sensitive stage to a hormone-refractory tumor following antihormonal therapy.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 (1984)). Chimeric antibodies of interest herein include primatized antibodies comprising variable domain antigen-binding sequences derived from a non-human primate (e.g. Old World Monkey, Ape etc) and human constant region sequences.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact" antibody is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

Humanized anti-ErbB2 antibodies include huMAb4D5-1, huMAb4D5-2, huMAb4D5-3, huMAb4D5-4, huMAb4D5-

5, huMAb4D5-6, huMAb4D5-7 and huMAb4D5-8 (HERCEPTIN®) as described in Table 3 of U.S. Pat. No. 5,821,337 expressly incorporated herein by reference; humanized 520C9 (WO93/21319) and humanized 2C4 antibodies. The heavy chain and light chain of humanized antibody 2C4 are shown in FIGS. 1 and 2, respectively.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500, 362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable", as used in connection with antibodies, refers to the fact that certain portions of the antibody variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al, *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" an antigen of interest, e.g. ErbB2 antigen, is one capable of binding that antigen with sufficient affinity such that the antibody is useful as a diagnostic and/or therapeutic agent in targeting a cell expressing the antigen and/or for targeted delivery of a cytotoxic or other chemotherapeutic agent, such as a maytansinoid. Where the antibody is one which binds ErbB2, it will usually preferentially bind ErbB2 as opposed to other ErbB receptors, and may be one which does not significantly cross-react with other proteins such as EGFR, ErbB3 or ErbB4. In such embodiments, the extent of binding of the antibody to these non-ErbB2 proteins (e.g., cell surface binding to endogenous receptor) will be less than 10% as determined by fluorescence activated cell sorting (FACS) analysis or radioimmunoprecipitation (RIA). Sometimes, the anti-ErbB2 antibody will not significantly cross-react with the rat neu protein, e.g., as described in Schecter et al. *Nature* 312:513 (1984) and Drebin et al., *Nature* 312:545-548 (1984).

Unless indicated otherwise, the expressions "monoclonal antibody 4D5", and "4D5 monoclonal antibody" refer to an antibody that has antigen binding residues of, or derived from, the murine 4D5 antibody. For example, the monoclonal antibody 4D5 may be murine monoclonal antibody 4D5 (ATCC CRL 10463) or a variant thereof, such as humanized antibody 4D5, possessing antigen binding amino acid residues of murine monoclonal antibody 4D5. Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as in U.S. Pat. No. 5,821,337, with huMAb4D5-8 (HERCEPTIN®) being a preferred humanized 4D5 antibody.

An antibody having a "biological characteristic" of a designated antibody, such as the monoclonal antibody designated 4D5, is one which possesses one or more of the biological characteristics of that antibody which distinguish it from other antibodies that bind to the same antigen (e.g. ErbB2). For example, an antibody with a biological characteristic of 4D5 may show growth inhibitory effect on ErbB2 overexpressing cells in a manner that is dependent on the ErbB2 expression level and/or bind the same epitope in the extracellular domain of ErbB2 as that bound by 4D5 (e.g. which blocks binding of monoclonal antibody 4D5 to ErbB2).

A "growth inhibitory agent" when used herein refers to a compound or composition which inhibits growth of a cell, especially an ErbB expressing cancer cell either in vitro or in vivo. Thus, the growth inhibitory agent may be one which significantly reduces the percentage of ErbB expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (W B Saunders: Philadelphia, 1995), especially p. 13.

Examples of "growth inhibitory" antibodies are those which bind to ErbB2 and inhibit the growth of cancer cells overexpressing ErbB2. Preferred growth inhibitory anti-ErbB2 antibodies inhibit growth of SK-BR-3 breast tumor cells in cell culture by greater than 20%, and preferably greater than 50% (e.g. from about 50% to about 100%) at an antibody concentration of about 0.5 to 30 µg/ml, where the growth inhibition is determined six days after exposure of the SK-BR-3 cells to the antibody (see U.S. Pat. No. 5,677,171 issued Oct. 14, 1997). The SK-BR-3 cell growth inhibition assay is described in more detail in that patent and hereinbelow. The preferred growth inhibitory antibody is monoclonal antibody 4D5, e.g., humanized 4D5.

A molecule (e.g. antibody) which "induces cell death" is one which causes a viable cell to become nonviable. The cell is generally one which expresses the ErbB2 receptor, especially where the cell overexpresses the ErbB2 receptor. Preferably, the cell is a cancer cell, e.g. a breast, ovarian, stomach, endometrial, salivary gland, lung, kidney, colon, thyroid, pancreatic, prostate or bladder cancer cell. In vitro, the cell may be a SK-BR-3, BT474, Calu 3, MDA-MB-453, MDA-MB-361 or SKOV3 cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e. in the absence of complement) and in the absence of immune effector cells. To determine whether the molecule is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies are those which induce PI uptake in the PI uptake assay in BT474 cells. Examples of antibodies which induce cell death include anti-ErbB2 antibodies 7C2 and 7F3 (WO 98/17797, expressly incorporated herein by reference), including humanized and/or affinity matured variants thereof.

A molecule (e.g. antibody) which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the ErbB2 receptor. Preferably the cell is a tumor cell, e.g. a breast, ovarian, stomach, endometrial, salivary gland, lung, kidney, colon, thyroid, pancreatic, prostate or bladder cancer cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the molecule which induces apoptosis is one which results in about 2 to 50 fold, preferably about 5 to 50 fold, and most preferably about 10 to 50 fold, induction of annexin binding relative to untreated cell in an annexin binding assay using BT474 cells. Sometimes the pro-apoptotic molecule will be one which further blocks ErbB ligand activation of an ErbB receptor. In other situations, the molecule is one which does not significantly block ErbB ligand activation of an ErbB receptor. Further, the molecule may induce apoptosis, without inducing a large reduction in the percent of cells in S phase (e.g. one which only induces about 0-10% reduction in the percent of these cells relative to control). Examples of antibodies which induce apoptosis include anti-ErbB2 antibodies 7C2 and 7F3 (WO 98/17797, expressly incorporated herein by reference), including humanized and/or affinity matured variants thereof.

An antibody which "blocks" ligand activation of an ErbB receptor is one which reduces or prevents such activation as hereinabove defined, wherein the antibody is able to block ligand activation of the ErbB receptor substantially more effectively than monoclonal antibody 4D5, e.g. about as effectively as monoclonal antibodies 7F3 or 2C4 or Fab fragments thereof and preferably about as effectively as monoclonal antibody 2C4 or a Fab fragment thereof. For example, the antibody that blocks ligand activation of an ErbB receptor may be one which is about 50-100% more effective than 4D5 at blocking formation of an ErbB hetero-oligomer. Blocking of ligand activation of an ErbB receptor can occur by any means, e.g. by interfering with: ligand binding to an ErbB receptor, ErbB complex formation, tyrosine kinase activity of an ErbB receptor in an ErbB complex and/or phosphorylation of tyrosine kinase residue(s) in or by an ErbB receptor. Examples of antibodies which block ligand activation of an ErbB receptor include monoclonal antibodies 2C4 and 7F3 (which block HRG activation of ErbB2/ErbB3 and ErbB2/ErbB4 hetero-oligomers; and EGF, TGF-α, amphiregulin, HB-EGF and/or epiregulin activation of an EGFR/ErbB2 hetero-oligomer); and L26, L96 and L288 antibodies (Klapper et al. *Oncogene* 14:2099-2109 (1997)), which block EGF and NDF binding to T47D cells which express EGFR, ErbB2, ErbB3 and ErbB4. Humanized and/or affinity matured variants these and other antibodies within the definition are specifically included.

The term "epitope" is used to refer to binding sites for (monoclonal or polyclonal) antibodies on protein antigens.

Antibodies that bind to a certain epitope are identified by "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. Competition assays are discussed below. According to the gene fragment expression assays, the open reading frame encoding the protein is fragmented either randomly or by specific genetic constructions and the reactivity of the expressed fragments of the protein with the antibody to be tested is determined. The gene fragments may, for example, be produced by PCR and then transcribed and translated into protein in vitro, in the presence of radioactive amino acids. The binding of the antibody to the radioactively labeled protein fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. The latter approach is suitable to define linear epitopes of about 5 to 15 amino acids.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The "epitope 4D5" is the region in the extracellular domain of ErbB2 to which the antibody 4D5 (ATCC CRL 10463) binds. This epitope is close to the transmembrane domain of ErbB2, and extends from about residue 519 to about residue 625, inclusive within the ErbB2 extracellular domain sequence included in SEQ ID NO: 3, FIG. 4. To screen for antibodies which bind to the 4D5 epitope, a routine cross-blocking assay such as that described in Harlow and Lane, supra, can be performed. Alternatively, epitope mapping can be performed to assess whether the antibody binds to the 4D5 epitope of ErbB2 (e.g. any one or more residues in the region from about residue 529 to about residue 625, inclusive in SEQ ID NO: 3).

The "epitope 3H4" is the region in the extracellular domain of ErbB2 to which the antibody 3H4 binds. This epitope includes residues from about 541 to about 599, inclusive, in the amino acid sequence of ErbB2 extracellular domain (see FIG. 4 and SEQ ID NO: 3).

The "epitope 7C2/7F3" is the region at the N terminus of the extracellular domain of ErbB2 to which the 7C2 and/or 7F3 antibodies (each deposited with the ATCC, see below) bind. To screen for antibodies which bind to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2/7F3 epitope on ErbB2 (e.g. any one or more of residues in the region from about residue 22 to about residue 53 of ErbB2; see FIG. 4, and SEQ ID NO: 3).

A tumor which "does not respond, or responds poorly, to treatment with a monoclonal anti-ErbB antibody" does not show statistically significant improvement in response to anti-ErbB antibody treatment when compared to no treatment or treatment with placebo in a recognized animal model or a human clinical trial, or which responds to initial treatment with anti-ErbB antibodies but grows as treatment is continued. A particularly suitable animal model for testing the efficacy of anti-ErbB antibodies is the transgenic animal model disclosed herein, and illustrated in Example 3.

The terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "disorder" is any condition that would benefit from treatment of the present invention. This includes chronic and acute disorders or diseases including those pathological conditions which predispose the mammal to the disorder in question. Non-limiting examples of disorders to be treated herein include benign and malignant tumors; leukemias and lymphoid malignancies, in particular breast, ovarian, stomach, endometrial, salivary gland, lung, kidney, colon, thyroid, pancreatic, prostate or bladder cancer. A preferred disorder to be treated in accordance with the present invention is malignant tumor, such as breast cancer, that overexpresses an ErbB receptor (e.g. ErbB2 and/or EGFR), and does not respond or responds poorly to treatment with antibody to the receptor(s) that is/are overexpressed. A particularly preferred disorder is an ErbB2-overexpressing breast cancer that does not respond or responds poorly to HERCEPTIN® therapy.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "objective response rate" refers to the number of treated individuals that respond to treatment as determined by a quantitative measure.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2'-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, β-fluorocytosine and other β-fluorouridine prodrugs which can be converted into the more active cytotoxic free drug. Examples of cytotoxic drugs that can be derivatized into a prodrug form for use in this invention include, but are not limited to, those chemotherapeutic agents described above.

The term "nucleic acid" refers to polynucleotides such as deoxyribonucleic acid (DNA), and, where appropriate, ribonucleic acid (RNA). The term also includes, as equivalents, analogs of either DNA or RNA made from nucleotide analogs, and as applicable, single (sense or antisense) and double-stranded polynucleotides. An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

As used herein, the term "vector" refers to a nucleic acid molecule capable of transporting another nucleic acid to which it has been linked. The term "expression vector" includes plasmids, cosmids or phages capable of synthesizing the subject HER2 protein encoded by the respective recombinant gene carried by the vector. Preferred vectors are those capable of autonomous replication and/expression of nucleic acids to which they are linked. In the present specification, "plasmid" and "vector" are used interchangeably, as the plasmid is the most commonly used form of vector.

As used herein, the terms "transcriptional regulatory elements" and "transcriptional regulatory sequences" are used interchangeably and refer to nucleic acid, e.g. DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, enhancers, splicing signals and polyadenylation signals. These terms are intended to encompass all elements that promote or regulate transcription, including promoters, core elements required for basic interaction of RNA polymerase and transcription factors, upstream elements, enhancers, and response elements (Lewin, "Genes V" (Oxford University Press, Oxford) pages 847-873). Reference herein to the transcriptional regulatory elements of a gene or class of gene includes both all or an intact region of the naturally occurring transcriptional regulatory elements and modified forms of the transcriptional regulatory elements of the gene or group of genes. Such modified forms include rearrangements of the elements, deletions of some elements or extraneous sequences, and insertion of heterologous elements. The modular nature of transcriptional regulatory elements and the absence of position-dependence of the function of some regulatory elements such as enhancers make such modifications possible. Numerous techniques are available for dissecting the regulatory elements of genes to determine their location and function. Such information can be used to direct modification of the elements, if desired. It is preferred, however, that an intact region of the transcriptional regulatory elements of a gene be used.

The term "tissue-specific promoter" means a nucleotide sequence that serves as a promoter, i.e., regulates expression of a selected DNA sequence operably linked to the promoter, and which effects expression of the selected DNA sequence in specific cells of a tissue, such as cells of a mammary gland. In an illustrative embodiment, gene constructs utilizing mammary gland-specific promoters can be used to preferentially direct expression of a HER2 protein or protein fragment in the mammary gland tissue.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "transfection" refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of HER2.

As used herein, the term "transgene" refers to a nucleic acid sequence which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can be operably linked to one or more transcriptional regulatory sequences and any other nucleic acid, such as introns, that may be necessary for optimal expression of a selected nucleic acid.

Accordingly, the term "transgene construct" refers to a nucleic acid which includes a transgene, and (optionally) such other nucleic acid sequences as transcriptionally regulatory sequence, polyadenylation sites, replication origins, marker genes, etc., which may be useful in the general manipulation of the transgene for insertion in the genome of a host organism.

The term "transgenic" is used herein as an adjective to describe the property, for example, of an animal or a construct, of harboring a transgene. For instance, as used herein, a "transgenic organism" is any animal, preferably a non-human mammal, in which one or more of the cells of the animal-contain heterologous nucleic acid introduced by way of human intervention, such as by trangenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express or overexpress a recombinant form of the subject HER2 proteins. The terms "founder line" and "founder animal" refer to those animals that are the mature product of the embryos to which the transgene was added, i.e., those animals that grew from the embryos into which DNA was inserted, and that were implanted into one or more surrogate hosts.

The terms "progeny" and "progeny of the transgenic animal" refer to any and all offspring of every generation subsequent to the originally transformed mammals. The term "non-human mammal" refers to all members of the class Mammalia except humans. "Mammal" refers to any animal classified as a mammal, including humans, domestic and farm animals, and zoo, sports, or pet animals, such as mouse, rat, rabbit, pig, sheep, goat, cattle and higher primates.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

A "cardioprotectant" is a compound or composition which prevents or reduces myocardial dysfunction (i.e. cardiomyopathy and/or congestive heart failure) associated with administration of a drug, such as an anti-ErbB antibody or its maytansinoid conjugate, to a patient. The cardioprotectant may, for example, block or reduce a free-radical-mediated cardiotoxic effect and/or prevent or reduce oxidative-stress injury. Examples of cardioprotectants encompassed by the present definition include the iron-chelating agent dexrazoxane (ICRF-187) (Seifert et al. *The Annals of Pharmacotherapy* 28:1063-1072 (1994)); a lipid-lowering agent and/or anti-oxidant such as probucol (Singal et al. *J. Mol. Cell. Cardiol.* 27:1055-1063 (1995)); amifostine (aminothiol 2-[(3-aminopropyl)amino]ethanethiol-dihydrogen phosphate ester, also called WR-2721, and the dephosphorylated cellular uptake form thereof called WR-1065) and S-3-(3-methylaminopropylamino)propylphosphorothioic acid (WR-151327), see Green et al. *Cancer Research* 54:738-741 (1994); digoxin (Bristow, M. R. In: Bristow M R, ed. *Drug-Induced Heart Disease*. New York: Elsevier 191-215 (1980)); beta-blockers such as metoprolol (Hjalmarson et al. *Drugs* 47:Suppl 4:31-9 (1994); and Shaddy et al. *Am. Heart J.* 129: 197-9 (1995)); vitamin E; ascorbic acid (vitamin C); free radical scavengers such as oleanolic acid, ursolic acid and N-acetylcysteine (NAC); spin trapping compounds such as alpha-phenyl-tert-butyl nitrone (PBN); (Paracchini et al., *Anticancer Res.* 13:1607-1612 (1993)); selenoorganic compounds such as P251 (Elbesen); and the like.

2. Detailed Description

The present invention is based on results obtained in a novel murine HER2-transgenic tumor model in which HERCEPTIN® or the murine antibody 4D5 from which HERCEPTIN® was derived, had little effect on tumor growth. Using this model to test the efficacy of HERCEPTIN® and HERCEPTIN®-maytansinoid conjugates, it was surprisingly found that while the transplanted tumor obtained from such transgenic mice responded poorly to HERCEPTIN® treatment, the HERCEPTIN®-maytansinoid conjugates were highly efficacious.

Accordingly, the present invention is based on the use of anti-ErbB antibody-maytansinoid conjugates in the treatment of ErbB overexpressing tumors that do not respond well to anti-ErbB antibody and/or maytansinoid treatment.

A. Production of Anti-ErbB Antibodies

A description follows as to exemplary techniques for the production of the antibodies used in accordance with the present invention. The production of antibodies will be illustrated with reference to anti-ErbB2 antibodies but it will be apparent for those skilled in the art that antibodies to other members of the ErbB receptor family can be produced and modified in a similar manner.

The ErbB2 antigen to be used for production of antibodies may be, e.g., a soluble form of the extracellular domain of ErbB2 or a portion thereof, containing the desired epitope. Alternatively, cells expressing ErbB2 at their cell surface (e.g. NIH-3T3 cells transformed to overexpress ErbB2; or a carcinoma cell line such as SK-BR-3 cells, see Stancovski et al. *PNAS* (USA) 88:8691-8695 (1991)) can be used to generate antibodies. Other forms of ErbB2 useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Example 1 below describes production of an exemplary humanized anti-ErbB2 antibody. The humanized antibody herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest*, 5th Ed. Public Health Service, National Institutes of Health, Bethesda, Md. (1991). In one embodiment, the humanized antibody comprises FR substitutions at two or all of positions 69H, 71H and 73H.

Various forms of the humanized antibody are contemplated. For example, the humanized antibody may be an antibody fragment, such as a Fab. Alternatively, the humanized antibody may be an intact antibody, such as an intact IgG1 antibody.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); nd U.S. Pat. Nos. 5,591,669, 5,589,369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human anti-ErbB2 antibodies are described in U.S. Pat. No. 5,772,997 issued Jun. 30, 1998 and WO 97/00271 published Jan. 3, 1997.

(v) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10: 163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the ErbB2 protein. Other such antibodies may combine an ErbB2 binding site with binding site(s) for EGFR, ErbB3 and/or ErbB4. Alternatively, an anti-ErbB2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the ErbB2-expressing cell. Bispecific antibodies may also be used to localize cytotoxic agents to cells which express ErbB2. WO 96/16673 describes a bispecific anti-ErbB2/anti-FcγRI antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli,* which can be chemically coupled to form bispecific antibodies. Shalaby et al., *J. Exp. Med.,* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.,* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al. *J. Immunol* 147: 60 (1991).

(vii) Other Amino Acid Sequence Modifications

Amino acid sequence modification(s) of the anti-ErbB2 antibodies described herein are contemplated. For example, it may be desirable to improve the binding affinity and/or other biological properties of the antibody. Amino acid sequence variants of the anti-ErbB2 antibody are prepared by introducing appropriate nucleotide changes into the anti-ErbB2 antibody nucleic acid, or by peptide synthesis. Such modifications include, for example, deletions from, and/or insertions into and/or substitutions of, residues within the amino acid sequences of the anti-ErbB2 antibody. Any combination of deletion, insertion, and substitution is made to arrive at the final construct, provided that the final construct possesses the desired characteristics. The amino acid changes also may alter post-translational processes of the anti-ErbB2 antibody, such as changing the number or position of glycosylation sites.

A useful method for identification of certain residues or regions of the anti-ErbB2 antibody that are preferred locations for mutagenesis is called "alanine scanning mutagenesis" as described by Cunningham and Wells Science, 244: 1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with ErbB2 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-ErbB2 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-ErbB2 antibody with an N-terminal methionyl residue or the antibody fused to a cytotoxic polypeptide. Other insertional variants of the anti-ErbB2 antibody molecule include the fusion to the N- or C-terminus of the anti-ErbB2 antibody to an enzyme (e.g. for ADEPT) or a polypeptide which increases the serum half-life of the antibody.

Another type of variant is an amino acid substitution variant. These variants have at least one amino acid residue in the anti-ErbB2 antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |

TABLE 1-continued

| Original Residue | Exemplary Substitutions | Preferred Substitutions |
|---|---|---|
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the anti-ErbB2 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human ErbB2. Such contact residues and neighboring residues are candidates for substitution according to the techniques elaborated herein. Once such variants are generated, the panel of variants is subjected to screening as described herein and antibodies with superior properties in one or more relevant assays may be selected for further development.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(viii) Glycosylation Variants

Antibodies are glycosylated at conserved positions in their constant regions (Jefferis and Lund, *Chem. Immunol.* 65:111-128 [1997]; Wright and Morrison, *TibTECH* 15:26-32 [1997]). The oligosaccharide side chains of the immunoglobulins affect the protein's function (Boyd et al., *Mol. Immunol.* 32:1311-1318 [1996]; Wittwe and Howard, *Biochem.* 29:4175-4180 [1990]), and the intramolecular interaction between portions of the glycoprotein which can affect the conformation and presented three-dimensional surface of the glycoprotein (Hefferis and Lund, supra; Wyss and Wagner, *Current Opin. Biotech.* 7:409-416 [1996]). Oligosaccharides may also serve to target a given glycoprotein to certain molecules based upon specific recognition structures. For example, it has been reported that in agalactosylated IgG, the oligosaccharide moiety 'flips' out of the inter-CH2 space and terminal N-acetylglucosamine residues become available to bind mannose binding protein (Malhotra et al., *Nature Med.* 1:237-243 [1995]). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., *Mol. Immunol.* 32:1311-1318 [1996]), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., *Mature Biotech.* 17:176-180 [1999]).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetyl-galactosamine, galactose, or xylose to a hydroxyamino acid, most commonly serine or threonine, although 5-hydroxyproline or 5-hydroxylysine may also be used.

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. Nucleic acid molecules encoding amino acid sequence variants of the anti-ErbB2 antibody are prepared by a variety of methods is known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-ErbB2 antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g. antibodies, as potential therapeutics is rarely the native cell, significant variations in the glycosylation pattern of the antibodies can be expected (see, e.g. Hse et al., *J. Biol. Chem.* 272:9062-9070 [1997]). In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5.278,299). Glycosylation, or certain types of glycosylation, can be enzymatically removed from the glycoprotein, for example using endoglycosidase H (Endo H). In addition, the recombinant host cell can be genetically engineered, e.g. make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

(viii) Screening for Antibodies with the Desired Properties

Techniques for generating antibodies have been described above. One may further select antibodies with certain biological characteristics, as desired.

For example, to identify growth inhibitory anti-ErbB2 antibodies, one may screen for antibodies which inhibit the growth of cancer cells which overexpress ErbB2. In one embodiment, the growth inhibitory antibody of choice is able to inhibit growth of SK-BR-3 cells in cell culture by about 20-100% and preferably by about 50-100% at an antibody concentration of about 0.5 to 30 μg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish). 0.5 to 30 μg/ml of the anti-ErbB2 antibody is added per dish. After six days, the number of cells, compared to untreated cells are counted using an electronic COULTER™ cell counter. Those antibodies which inhibit growth of the SK-BR-3 cells by about 20-100% or about 50-100% may be selected as growth inhibitory antibodies.

To select for antibodies which induce cell death, loss of membrane integrity as indicated by, e.g., PI, trypan blue or 7AAD uptake may be assessed relative to control. The preferred assay is the PI uptake assay using BT474 cells. According to this assay, BT474 cells (which can be obtained from the American Type Culture Collection (Rockville, Md.)) are cultured in Dulbecco's Modified Eagle Medium (D-MEM): Ham's F-12 (50:50) supplemented with 10% heat-inactivated FBS (Hyclone) and 2 mM L-glutamine. (Thus, the assay is performed in the absence of complement and immune effector cells). The BT474 cells are seeded at a density of $3 \times 10^6$ per dish in 100×20 mm dishes and allowed to attach overnight. The medium is then removed and replaced with fresh medium alone or medium containing 10 μg/ml of the appropriate monoclonal antibody. The cells are incubated for a 3 day time period. Following each treatment, monolayers are washed with PBS and detached by trypsinization. Cells are then centrifuged at 1200 rpm for 5 minutes at 4° C., the pellet resuspended in 3 ml ice cold $Ca^{2+}$ binding buffer (10 mM Hepes, pH 7.4, 140 mM NaCl, 2.5 mM $CaCl_2$) and aliquoted into 35 mm strainer-capped 12×75 tubes (1 ml per tube, 3 tubes per treatment group) for removal of cell clumps. Tubes then receive PI (10 μg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

In order to select for antibodies which induce apoptosis, an annexin binding assay using BT474 cells is available. The BT474 cells are cultured and seeded in dishes as discussed in the preceding paragraph. The medium is then removed and replaced with fresh medium alone or medium containing 10 μg/ml of the monoclonal antibody. Following a three day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g. annexin V-FTIC) (1 μg/ml). Samples may be analyzed using a FACSCAN™ flow cytometer and FACSCONVERT™ CellQuest software (Becton Dickinson).

Those antibodies which induce statistically significant levels of annexin binding relative to control are selected as apoptosis-inducing antibodies.

In addition to the annexin binding assay, a DNA staining assay using BT474 cells is available. In order to perform this assay, BT474 cells which have been treated with the antibody of interest as described in the preceding two paragraphs are incubated with 9 μg/ml HOECHST 33342™ for 2 hr at 37° C., then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay.

To identify an antibody which blocks ligand activation of an ErbB receptor, the ability of the antibody to block ErbB ligand binding to cells expressing the ErbB receptor (e.g. in conjugation with another ErbB receptor with which the ErbB receptor of interest forms an ErbB hetero-oligomer) may be determined. For example, cells naturally expressing, or transfected to express, ErbB receptors of the ErbB hetero-oligomer may be incubated with the antibody and then exposed to labeled ErbB ligand. The ability of the anti-ErbB2 antibody to block ligand binding to the ErbB receptor in the ErbB hetero-oligomer may then be evaluated.

For example, inhibition of HRG binding to MCF7 breast tumor cell lines by anti-ErbB2 antibodies may be performed using monolayer MCF7 cultures on ice in a 24-well-plate format essentially as described in Example 1 below. Anti-ErbB2 monoclonal antibodies may be added to each well and incubated for 30 minutes. $^{125}$I-labeled rHRGβ$1_{177-224}$ (25 pm) may then be added, and the incubation may be continued for 4 to 16 hours. Dose response curves may be prepared and an $IC_{50}$ value may be calculated for the antibody of interest. In one embodiment, the antibody which blocks ligand activation of an ErbB receptor will have an $IC_{50}$ for inhibiting HRG binding to MCF7 cells in this assay of about 50 nM or less, more preferably 10 nM or less. Where the antibody is an antibody fragment such as a Fab fragment, the $IC_{50}$ for inhibiting HRG binding to MCF7 cells in this assay may, for example, be about 100 nM or less, more preferably 50 nM or less.

Alternatively, or additionally, the ability of the anti-ErbB2 antibody to block ErbB ligand-stimulated tyrosine phosphorylation of an ErbB receptor present in an ErbB hetero-oligomer may be assessed. For example, cells endogenously expressing the ErbB receptors or transfected to expressed them may be incubated with the antibody and then assayed for ErbB ligand-dependent tyrosine phosphorylation activity using an anti-phosphotyrosine monoclonal (which is optionally conjugated with a detectable label). The kinase receptor activation assay described in U.S. Pat. No. 5,766,863 is also available for determining ErbB receptor activation and blocking of that activity by an antibody.

In one embodiment, one may screen for an antibody which inhibits HRG stimulation of p180 tyrosine phosphorylation in MCF7 cells. For example, the MCF7 cells may be plated in 24-well plates and monoclonal antibodies to ErbB2 may be added to each well and incubated for 30 minutes at room temperature; then rHRGβ$1_{177}$-244 may be added to each well to a final concentration of 0.2 nM, and the incubation may be continued for 8 minutes. Media may be aspirated from each well, and reactions may be stopped by the addition of 100 μl of SDS sample buffer (5% SDS, 25 mM DTT, and 25 mM Tris-HCl, pH 6.8). Each sample (25 μl) may be electrophoresed on a 4-12% gradient gel (Novex) and then electrophoretically transferred to polyvinylidene difluoride membrane. Antiphosphotyrosine (at 1 µg/ml) immunoblots may be developed, and the intensity of the predominant reactive band at $M_r$~180,000 may be quantified by reflectance densitometry. The antibody selected will preferably significantly inhibit HRG stimulation of p180 tyrosine phosphorylation to about 0-35% of control in this assay. A dose-response curve for inhibition of HRG stimulation of p180 tyrosine phosphorylation as determined by reflectance densitometry may be prepared and an $IC_{50}$ for the antibody of interest may be calculated. In one embodiment, the antibody which blocks ligand activation of an ErbB receptor will have an $IC_{50}$ for inhibiting HRG stimulation of p180 tyrosine phosphorylation in this assay of about 50 nM or less, more preferably 10 nM or less. Where the antibody is an antibody fragment such as a Fab fragment, the $IC_{50}$ for inhibiting HRG stimulation of p180 tyrosine phosphorylation in this assay may, for example, be about 100 nM or less, more preferably 50 nM or less.

One may also assess the growth inhibitory effects of the antibody on MDA-MB-175 cells, e.g, essentially as described in Schaefer et al. Oncogene 15:1385-1394 (1997). According to this assay, MDA-MB-175 cells may treated with an anti-ErbB2 monoclonal antibody (10 µg/mL) for 4 days and stained with crystal violet. Incubation with an anti-ErbB2 antibody may show a growth inhibitory effect on this cell line similar to that displayed by monoclonal antibody 2C4. In a further embodiment, exogenous HRG will not significantly reverse this inhibition. Preferably, the antibody will be able to inhibit cell proliferation of MDA-MB-175 cells to a greater extent than monoclonal antibody 4D5 (and optionally to a greater extent than monoclonal antibody 7F3), both in the presence and absence of exogenous HRG.

In one embodiment, the anti-ErbB2 antibody of interest may block heregulin dependent association of ErbB2 with ErbB3 in both MCF7 and SK-BR-3 cells as determined in a co-immunoprecipitation experiment substantially more effectively than monoclonal antibody 4D5, and preferably substantially more effectively than monoclonal antibody 7F3.

To screen for antibodies which bind to an epitope on ErbB2 bound by an antibody of interest, a routine cross-blocking assay such as that described in *Antibodies, A Laboratory Manual*, Cold Spring Harbor Laboratory, Ed Harlow and David Lane (1988), can be performed. Alternatively, or additionally, epitope mapping can be performed by methods known in the art (see, e.g. FIGS. 1A and 1B herein).

The results obtained in the cell-based assays described above can then be followed by testing in animal, e.g. murine, models, and human clinical trials. In particular, the inability or limited ability of an antibody to treat ErbB2 overexpressing tumors can be demonstrated in the transgenic mouse model disclosed in the present application as described in the Examples below.

B. Anti-ErbB Antibody-Maytansinoid Conjugates (Immunoconjugates)

Anti-ErbB antibody-maytansinoid conjugates are prepared by chemically linking an anti-ErbB antibody to a maytansinoid molecule without significantly diminishing the biological activity of either the antibody or the maytansinoid molecule. Maytansinoids are well known in the art and can be synthesized by known techniques or isolated from natural sources. Suitable maytansinoids are disclosed, for example, in U.S. Pat. No. 5,208,020 and in the other patents and non-patent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al *Cancer Research* 52: 127-131 (1992). The linking groups include disulfide groups, thioether groups, acid labile-groups, photolabile groups, peptidase labile groups, or esterase labile groups, as disclosed in the above-identified patents, disulfide and thioether groups being preferred.

In addition, there are many possible sites within the antibody molecule for linking maytansinoid to the antibody. For example, in one embodiment HERCEPTIN® can be linked to the maytansinoid at lysine 13 in the light chain, at lysine 32 in the heavy chain, at lysine 26 in both Fab fragments and at lysine 38 in. the Fc fragment.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

C. Pharmaceutical Formulations

Therapeutic formulations of the antibody-maytansinoid conjugates used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium;

metal complexes (e.g. Zn-protein complexes); and/or non-ionic surfactants such as TWEEN™, PLURONICS™ or polyethylene glycol (PEG). Preferred lyophilized anti-ErbB2 antibody formulations are described in WO 97/04801, expressly incorporated herein by reference.

The formulation herein may also contain more than one active compound as necessary for the particular indication being treated, preferably those with complementary activities that do not adversely affect each other. For example, it may be desirable to further provide antibodies or antibody-maytansinoid conjugates which bind to EGFR, ErbB2 (e.g. an antibody which binds a different epitope on ErbB2), ErbB3, ErbB4, or vascular endothelial factor (VEGF) in the one formulation. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

In one embodiment, the formulation comprises 5 mg/ml HERCEPTIN®-DM1, 100 mg/ml sucrose, 0.1% polysorbate 20 and 10 mM sodium succinate at pH 5.0.

D. Treatment with the Anti-ErbB2 Antibody-Maytansinoid Conjugates

It is contemplated that, according to the present invention, the anti-ErbB2 antibody-maytansinoid conjugates may be used to treat various diseases or disorders. Exemplary conditions or disorders include benign or malignant tumors; leukemias and lymphoid malignancies; other disorders such as neuronal, glial, astrocytal, hypothalamic, glandular, macrophagal, epithelial, stromal, blastocoelic, inflammatory, angiogenic and immunologic disorders.

Generally, the disease or disorder to be treated is cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The cancer will comprise ErbB-expressing cells, such that an anti-ErbB antibody herein is able to bind to the cancer, and will be typically characterized by overexpression of the ErbB receptor. In a preferred embodiment, the cancer comprises ErbB2-expressing cells, even more preferably, cells which are characterized by overexpression of the ErbB2 receptor. To determine ErbB, e.g. ErbB2 expression in the cancer, various diagnostic/prognostic assays are available. In one embodiment, ErbB2 overexpression may be analyzed by IHC, e.g. using the HERCEPTEST® (Dako). Parrafin embedded tissue sections from a tumor biopsy may be subjected to the IHC assay and accorded a ErbB2 protein staining intensity criteria as follows:

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for ErbB2 overexpression assessment may be characterized as not overexpressing ErbB2, whereas those tumors with 2+ or 3+ scores may be characterized as overexpressing ErbB2.

Alternatively, or additionally, fluorescence in situ hybridization (FISH) assays such as the INFORM™ (sold by Ventana, Ariz.) or PATHVISION™ (Vysis, Ill.) may be carried out on formalin-fixed, paraffin-embedded tumor tissue to determine the extent (if any) of ErbB2 overexpression in the tumor. In comparison with IHC assay, the FISH assay, which measures her2 gene amplification, seems to correlate better with response of patients to treatment with HERCEPTIN®, and is currently considered to be the preferred assay to identify patients likely to benefit from HERCEPTIN® treatment or treatment with the immunoconjugates of the present invention.

In one embodiment, the cancer will be one which expresses (and may overexpress) EGFR. Examples of cancers which may express/overexpress EGFR include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Preferably, the immunoconjugates of the present invention and/or ErbB, e.g. ErbB2 or EGFR protein to which they are bound are internalized by the cell, resulting in increased therapeutic efficacy of the immunoconjugate in killing the cancer cell to which they bind. In a preferred embodiment, the cytotoxic agent (maytansinoid) targets or interferes with nucleic acid in the cancer cell.

The treatment of the present invention targets ErbB overexpressing tumors that do not respond, or respond poorly, to treatment with an unconjugated anti-ErbB antibody. Such patients might have received prior treatment with an anti-ErbB antibody not conjugated to a maytansinoid moiety, where the prior treatment either did not result in significant improvement, or resulted in transient response. Prior treatment of any particular patient with an unconjugated anti-ErbB antibody is, however, not a prerequisite of identifying patients who are candidates for treatment in accordance with the present invention. An ordinary skilled physician can readily identify patients who are expected to benefit from treatment with the immunoconjugates of the present invention based on publicly available clinical data and his or her own experience. Treatment of mammals, and in particular human patients, with or without prior treatment with an (unconjugated) anti-ErbB antibody is specifically within the scope of the present invention.

The anti-ErbB antibody-maytansinoid conjugates are administered to a mammal, preferably to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

Other therapeutic regimens may be combined with the administration of the anti-ErbB antibody-maytansinoid conjugates. The combined administration includes coadministration, using separate formulations or a single pharmaceutical formulation, and consecutive administration in either order, wherein preferably there is a time period while both (or all) active agents simultaneously exert their biological activities.

In one preferred embodiment, the patient is treated with two or more different anti-ErbB antibodies, at least one of which is in the form of a maytansinoid conjugate. For example, the patient may be treated with a first anti-ErbB2 antibody-maytansinoid conjugate in which the antibody is growth inhibitory (e.g. HERCEPTIN®), and a second anti-ErbB2 antibody or antibody-immunoconjugate, e.g. an anti-body-maytansinoid conjugate which blocks ligand activation of an ErbB receptor (e.g. 2C4 or a humanized and/or affinity matured variant thereof) or induces apoptosis of an ErbB2-overexpressing cell (e.g. 7C2, 7F3 or humanized variants thereof). In another embodiment, the treatment involves the administration of antibodies that specifically bind two or more different ErbB receptors, such as, for example, ErbB2 and EGFR receptors, where at least one of the anti-ErbB antibodies is administered as a maytansinoid conjugate. Preferably such combined therapy results in a synergistic therapeutic effect.

It may also be desirable to combine administration of the anti-ErbB antibody-maytansinoid conjugates, with administration of an antibody directed against another tumor-associated antigen, which is not member of the ErbB family of receptors. The other antibody in this case may, for example, bind to vascular endothelial growth factor (VEGF), and may be in the form of a maytansinoid conjugate, or another immunoconjugate.

In one embodiment, the treatment of the present invention involves the combined administration of an anti-ErbB2 anti-body-maytansinoid conjugate (or conjugates) and one or more chemotherapeutic agents or growth inhibitory agents, including coadministration of cocktails of different chemotherapeutic agents. Preferred chemotherapeutic agents include taxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

In a preferred embodiment, the treatment is initiated with an anti-ErbB antibody-maytansinoid conjugate, followed by maintenance treatment with an unconjugated or 'naked' anti-ErbB antibody. This strategy may eliminate or reduce tumor cells resistant to the naked antibody in the initial round because of the ability of the antibody-DM1 conjugate to effectively kill such tumor cells.

The antibody-maytansinoid conjugates may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is hormone independent cancer, the patient may previously have been subjected to anti-hormonal therapy and, after the cancer becomes hormone independent, the anti-ErbB2 antibody (and optionally other agents as described herein) may be administered to the patient.

Sometimes, it may be beneficial to also coadminister a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

Suitable dosages for any of the above coadministered agents are those presently used and may be lowered due to the combined action (synergy) of the agent and anti-ErbB2 antibody.

For the prevention or treatment of disease, the appropriate dosage of antibody-maytansinoid conjugates will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody-maytansinoid conjugate is suitably administered to the patient at one time or over a series of treatments. Depending on the type and severity of the disease, about 1 µg/kg to 15 mg/kg (e.g. 0.1-20 mg/kg) of antibody-maytansinoid conjugate is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. A preferred dosing regimen comprises administering an initial loading dose of about 4 mg/kg, followed by a weekly maintenance dose of about 2 mg/kg of the anti-ErbB2 antibody-maytansinoid conjugate.

However, other dosage regimens may be useful. The progress of this therapy is easily monitored by conventional techniques and assays.

Based on the data disclosed herein, it is anticipated that one useful dosing protocol may entail approximately weekly (or less frequent) administration of the anti-ErbB antibody-maytansinoid conjugate where each dose of the conjugate is about 0.2-10 mg/kg, preferably about 1-3 mg/kg of the conjugate (e.g. where there are 1 to about 10, preferably about 3-4, maytansinoid molecules conjugated to each antibody molecule). From about 2-10, preferably about 4-6, dosages of the conjugate may be administered to the patient approximately every week.

In a preferred embodiment, the patients are treated initially with anti-ErbB-maytansinoid conjugate followed by therapy with unconjugated anti-ErbB antibody. Preferably, the anti-ErbB antibody in the conjugate and the unconjugated antibody are the same antibody. For example, treatment could be initiated with weekly injections of HERCEPTIN®-DM1 at about 0.5-5 mg/kg, preferably at about 1-3 mg/kg for 4-6 weeks, with the option of repeating this treatment. Patients can then be rolled over to conventional HERCEPTIN® therapy, which typically consists of treatment with a 4 mg/kg initial dose of HERCEPTIN®, followed by weekly treatment with a maintenance dose of 2 mg/kg. However, the 4 mg/kg initial dose may be omitted, with therapy going straight to the 2 mg/kg maintenance dose.

E. Articles of Manufacture

In another embodiment of the invention, an article of manufacture containing materials useful for the treatment of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an anti-ErbB2 antibody-maytansinoid conjugate. In one embodiment the container is a 10 cc vial containing 10 mL of a solution comprising HERCEPTIN®-DM1.

The label or package insert indicates that the composition is used for treating the condition of choice, such as cancer. In one embodiment, the label or package inserts indicates that the composition comprising the antibody which binds ErbB2 can be used to treat cancer which expresses an ErbB receptor selected from the group consisting of epidermal growth factor receptor (EGFR), ErbB2, ErbB3 and ErbB4, preferably EGFR. In addition, the label or package insert may indicate that the patient to be treated is one having cancer characterized by excessive activation of an ErbB receptor selected from EGFR, ErbB2, ErbB3 or ErbB4. For example, the cancer may be one which overexpresses one of these receptors and/or which overexpresses an ErbB ligand (such as TGF-α). The label or package insert may also indicate that the composition can be used to treat cancer, wherein the cancer is not characterized by overexpression of the ErbB2 receptor. For example, whereas the present package insert for HERCEPTIN® indicates that the antibody is used to treat patients with metastatic breast cancer whose tumors overexpress the ErbB2 protein, the package insert herein may indicate that the antibody or composition is used to treat cancer that does not respond, or respond poorly, to treatment with HERCEPTIN®. In other embodiments, the package insert may indicate that the antibody-maytansinoid conjugate or composition can be used also to treat hormone independent cancer, prostate cancer, colon cancer or colorectal cancer.

Moreover, the article of manufacture may comprise (a) a first container with a composition contained therein, wherein the composition comprises a maytansinoid conjugate of a first antibody which binds ErbB2 and inhibits growth of cancer cells which overexpress ErbB2; and (b) a second container with a composition contained therein, wherein the composition comprises a second antibody which binds ErbB2 and blocks ligand activation of an ErbB receptor, or a conjugate of this second antibody with a maytansinoid. The article of manufacture in this embodiment of the invention may further comprises a package insert indicating that the first and second compositions can be used to treat cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Further details of the invention are illustrated in the following non-limiting examples.

Example 1

Production, Characterization and Humanization of Anti-ErbB2 Monoclonal Antibody 4D5

The murine monoclonal antibody 4D5 which specifically binds the extracellular domain of ErbB2 was produced as described in Fendly et al., *Cancer Research* 50:1550-1558 (1990). Briefly, NIH 3T3/HER2-$3_{400}$ cells (expressing approximately $1 \times 10^5$ ErbB2 molecules/cell) produced as described in Hudziak et al *Proc. Natl. Acad. Sci. (USA)* 84:7158-7163 (1987) were harvested with phosphate buffered saline (PBS) containing 25 mM EDTA and used to immunize BALB/c mice. The mice were given injections i.p. of $10^7$ cells in 0.5 ml PBS on weeks 0, 2, 5 and 7. The mice with antisera that immunoprecipitated $^{32}$P-labeled ErbB2 were given i.p. injections of a wheat germ agglutinin-Sepharose (WGA) purified ErbB2 membrane extract on weeks 9 and 13. This was followed by an i.v. injection of 0.1 ml of the ErbB2 preparation and the splenocytes were fused with mouse myeloma line X63-Ag8.653. Hybridoma supernatants were screened for ErbB2-binding by ELISA and radioimmunoprecipitation.

Epitope Mapping and Characterization

The ErbB2 epitope bound by monoclonal antibody 4D5 was determined by competitive binding analysis (Fendly et al. *Cancer Research* 50:1550-1558 (1990)). Cross-blocking studies were done by direct fluorescence on intact cells using the PANDEX™ Screen Machine to quantitate fluorescence. The monoclonal antibody was conjugated with fluorescein isothiocyanate (FITC), using established procedures (Wofsy et al. *Selected Methods in Cellular Immunology*, p. 287, Mishel and Schiigi (eds.) San Francisco: W. J. Freeman Co. (1980)). Confluent monolayers of NIH 3T3/HER2-$3_{400}$ cells were trypsinized, washed once, and resuspended at $1.75 \times 10^6$ cell/ml in cold PBS containing 0.5% bovine serum albumin (BSA) and 0.1% $NaN_3$. A final concentration of 1% latex particles (IDC, Portland, Oreg.) was added to reduce clogging of the PANDEX™ plate membranes. Cells in suspension, 20 µl, and 20 µl of purified monoclonal antibodies (100 µg/ml to 0.1 µg/ml) were added to the PANDEX™ plate wells and incubated on ice for 30 minutes. A predetermined dilution of the FITC-labeled monoclonal antibody in 20 µl was added to each well, incubated for 30 minutes, washed, and the fluorescence was quantitated by the PANDEX™. Monoclonal antibodies were considered to share an epitope if each blocked binding of the other by 50% or greater in comparison to an irrelevant monoclonal antibody control. In this experiment, monoclonal antibody 4D5 was assigned epitope I (amino acid residues from about 529 to about 625, inclusive within the ErbB2 extracellular domain (see SEQ ID NO: 3).

The growth inhibitory characteristics of monoclonal antibody 4D5 were evaluated using the breast tumor cell line, SK-BR-3 (see Hudziak et al. *Molec. Cell. Biol.* 9(3):1165-1172 (1989)). Briefly, SK-BR-3 cells were detached by using 0.25% (vol/vol) trypsin and suspended in complete medium at a density of $4 \times 10^5$ cells per ml. Aliquots of 100 µl ($4 \times 10^4$ cells) were plated into 96-well microdilution plates, the cells were allowed to adhere, and 100 µl of media alone or media containing monoclonal antibody (final concentration 5 µg/ml) was then added. After 72 hours, plates were washed twice with PBS (pH 7.5), stained with crystal violet (0.5% in methanol), and analyzed for relative cell proliferation as described in Sugarman et al. *Science* 230:943-945 (1985). Monoclonal antibody 4D5 inhibited SK-BR-3 relative cell proliferation by about 56%.

Monoclonal antibody 4D5 was also evaluated for its ability to inhibit HRG-stimulated tyrosine phosphorylation of proteins in the $M_r$ 180,000 range from whole-cell lysates of MCF7 cells (Lewis et al. *Cancer Research* 56:1457-1465 (1996)). MCF7 cells are reported to express all known ErbB receptors, but at relatively low levels. Since ErbB2, ErbB3, and ErbB4 have nearly identical molecular sizes, it is not possible to discern which protein is becoming tyrosine phosphorylated when whole-cell lysates are evaluated by Western blot analysis. However, these cells are ideal for HRG tyrosine phosphorylation assays because under the assay conditions used, in the absence of exogenously added HRG, they exhibit low to undetectable levels of tyrosine phosphorylation proteins in the $M_r$ 180,000 range.

MCF7 cells were plated in 24-well plates and monoclonal antibodies to ErbB2 were added to each well and incubated for 30 minutes at room temperature; then rHRGβ1$_{177}$-244 was added to each well to a final concentration of 0.2 nM, and the incubation was continued for 8 minutes. Media was carefully aspirated from each well, and reactions were stopped by the addition of 100 µl of SDS sample buffer (5% SDS, 25 mM DTT, and 25 mM Tris-HCl, pH 6.8). Each sample (25 µl) was electrophoresed on a 4-12% gradient gel (Novex) and then electrophoretically transferred to polyvinylidene difluoride membrane. Antiphosphotyrosine (4G10, from UBI, used at 1 µg/ml) immunoblots were developed, and the intensity of the predominant reactive band at $M_r \sim 180,000$ was quantified by reflectance densitometry, as described previously (Holmes et al. *Science* 256:1205-1210 (1992); Sliwkowski et al. *J. Biol. Chem.* 269:14661-14665 (1994))

Monoclonal antibody 4D5 significantly inhibited the generation of a HRG-induced tyrosine phosphorylation signal at $M_r$ 180,000. In the absence of HRG, but was unable to stimulate tyrosine phosphorylation of proteins in the $M_r$ 180,000 range. Also, this antibody does not cross-react with EGFR (Fendly et al. *Cancer Research* 50:1550-1558 (1990)), ErbB3, or ErbB4. Monoclonal antibody 4D5 was able to block HRG stimulation of tyrosine phosphorylation by ~50%.

The growth inhibitory effect of monoclonal antibody 4D5 on MDA-MB-175 and SK-BR-3 cells in the presence or absence of exogenous rHRGβ1 was assessed (Schaefer et al. *Oncogene* 15:1385-1394 (1997)). ErbB2 levels in MDA-MB-175 cells are 4-6 times higher than the level found in normal breast epithelial cells and the ErbB2-ErbB4 receptor is constitutively tyrosine phosphorylated in MDA-MB-175 cells. Monoclonal antibody 4D5 was able to inhibit cell proliferation of MDA-MB-175 cells, both in the presence and absence of exogenous HRG. Inhibition of cell proliferation by 4D5 is dependent on the ErbB2 expression level (Lewis et al. *Cancer Immunol. Immunother.* 37:255-263 (1993)). A maximum inhibition of 66% in SK-BR-3 cells could be detected. However this effect could be overcome by exogenous HRG.

Humanization

The murine monoclonal antibody 4D5 was humanized, using a novel "gene conversion mutagenesis" strategy, as described in U.S. Pat. No. 5,821,337, the entire disclosure of which is hereby expressly incorporated by reference. The humanized monoclonal antibody 4D5 used in the following experiments is designated huMAb4D5-8. This antibody is of IgG1 isotype.

Example 2

HERCEPTIN®-DM1 Conjugates

1. Purification of HERCEPTIN®

HERCEPTIN® (huMAb4D5-8, rhuMAb HER2, U.S. Pat. No. 5,821,337) (1 vial containing 440 mg antibody) was dissolved in 50 ml MES buffer (25 mM MES, 50 mM NaCl, pH 5.6). The sample was loaded on a cation exchange column (Sepharose S, 15 cm×1.7 cm) that had been equilibrated in the same buffer. The column was then washed with the same buffer (5 column volumes). HERCEPTIN® was eluted by raising the NaCl concentration of the buffer to 200 mM. Fractions containing the antibody were pooled, diluted to 10 mg/mL, and dialyzed into a buffer containing 50 mm potassium phosphate, 50 mM NaCl, 2 mM EDTA, pH 6.5.

2. Modification of HERCEPTIN® with SPP

The purified HERCEPTIN® antibody was modified with N-succinimidyl-4-(2-pyridylthio)pentanoate (SPP) to introduce dithiopyridyl groups. The antibody (376.0 mg, 8 mg/mL) in 44.7 mL of 50 mM potassium phosphate buffer (pH 6.5) containing NaCl (50 mM) and EDTA (1 mM) was treated with SPP (5.3 molar equivalents in 2.3 mL ethanol). After incubation for 90 minutes under argon at ambient temperature, the reaction mixture was gel filtered through a Sephadex G25 column equilibrated with 35 mM sodium citrate, 154 mM NaCl, 2 mM EDTA. Antibody containing fractions were pooled and assayed. The degree of modification of the antibody was determined as described above. Recovery of the modified antibody (HERCEPTIN®-SPP-Py) was 337 mg (89.7%) with 4.5 releasable 2-thiopyridine groups linked per antibody.

3. Conjugation of HERCEPTIN®-SPP-Py with DM1

Figure 4:
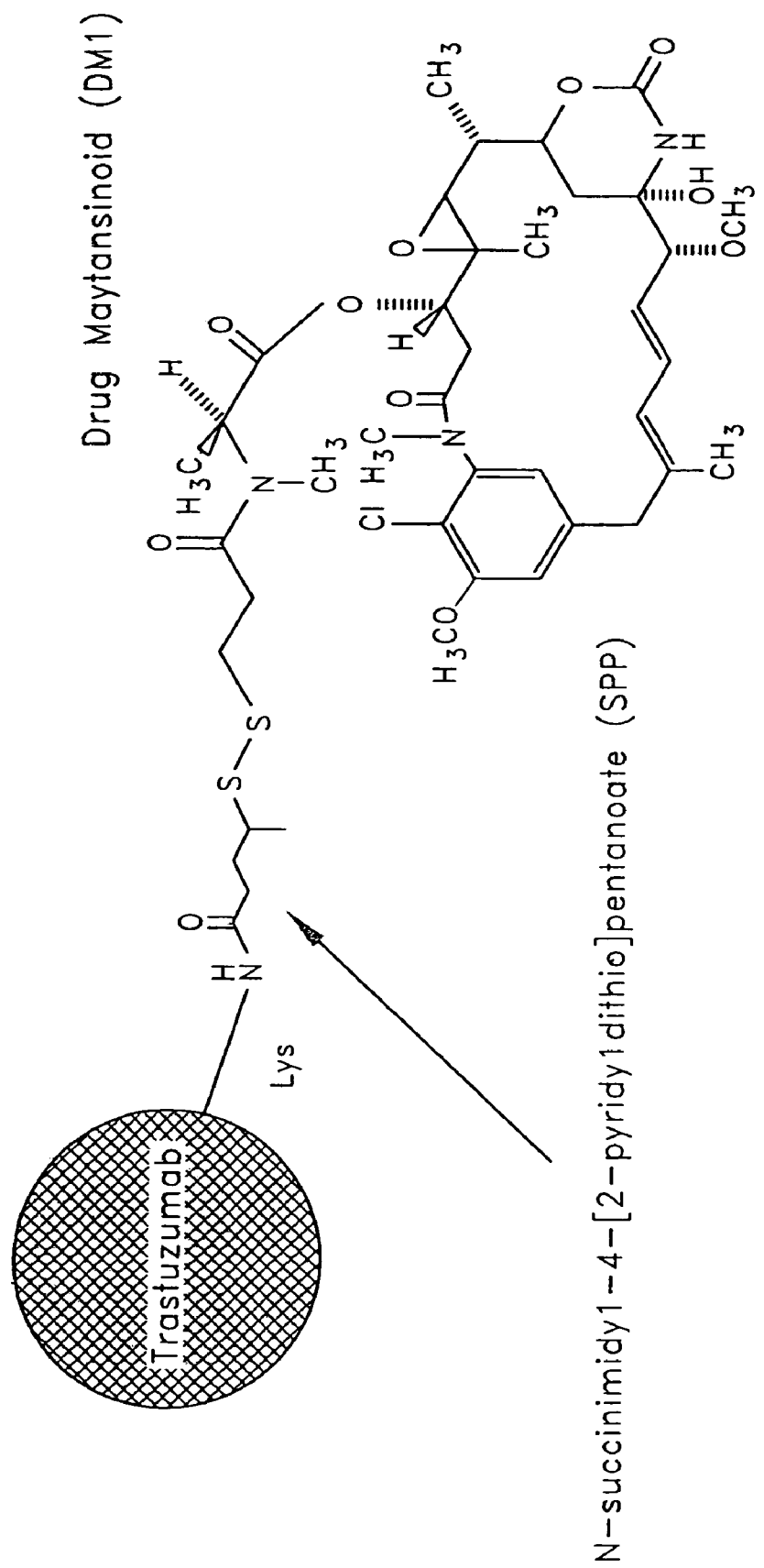
FIG. 4 illustrates the structure of a HERCEPTIN®-DM1 conjugate.

The modified antibody (337.0 mg, 9.5 µmols of releasable 2-thiopyridine groups) was diluted with the above 35 mM sodium citrate buffer, pH 6.5, to a final concentration of 2.5 mg/mL. DM1 (1.7 equivalents, 16.1 µmols) in 3.0 mM dimethylacetamide (DMA, 3% v/v in the final reaction mixture) was then added to the antibody solution. The structure of DM1 is shown in FIG. 3, where the nature of the "R" group is not critical and can be occupied, for example, by a variety of groups capable of forming a chemical bond with a linker. DM1 used in the present reaction was stored as an S—S form, which is more stable, and was reduced to the SH form for conjugation with the HERCEPTIN® antibody. The reaction proceeded at ambient temperature under argon for 20 hours. The structure of HERCEPTIN®-DM1 conjugates is illustrated in FIG. 4.

Figure 5:
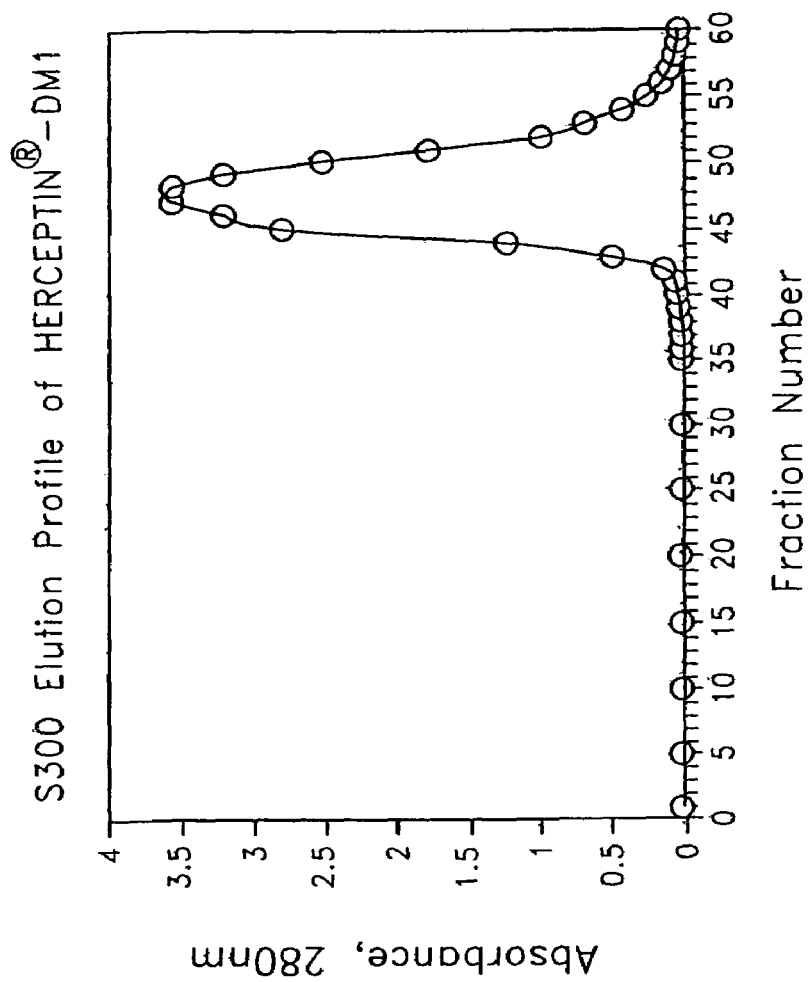
FIG. 5 is the elution profile of HERCEPTIN®-DM1 conjugate on a Sephacryl S300 gel filtration column.

The reaction was loaded on a Sephacryl S300 gel filtration column (5.0 cm×90.0 cm, 1.77 L) equilibrated with 35 mM sodium citrate, 154 mM NaCl, pH 6.5. The flow rate was 5.0 mL/min and 65 fractions (20.0 mL each) were collected. A major peak centered around fraction No. 47 (FIG. 5). The major peak comprises monomeric HERCEPTIN®-DM1. Fractions 44-51 were pooled and assayed. The number of DM1 drug molecules linked per antibody molecule was determined by measuring the absorbance at 252 nm and 280 nm, and found to be 3.7 drug molecules per antibody molecule.

4. Anti-Proliferative Effect of HERCEPTIN®-DM1 Conjugate In Vitro

Figure 6:
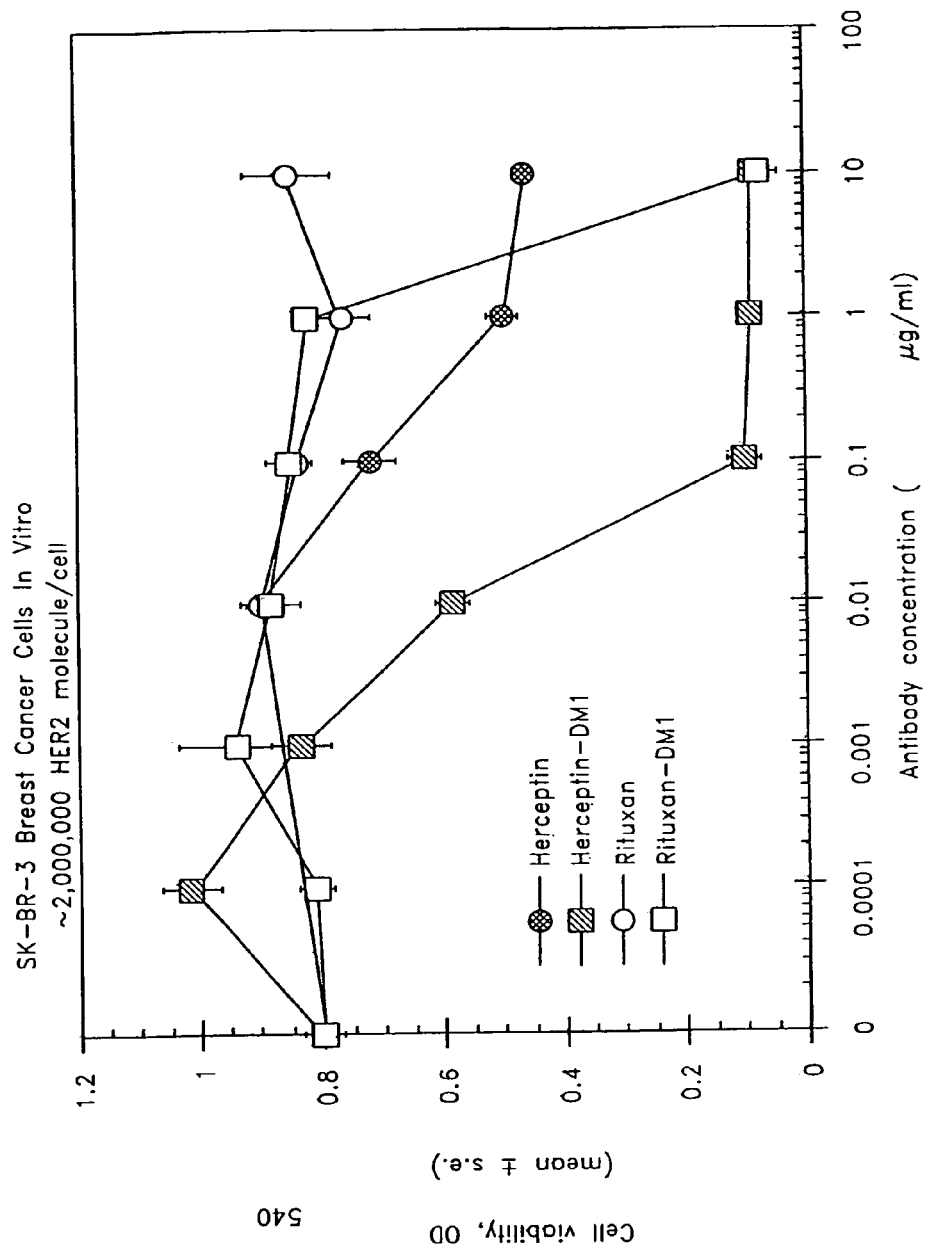
FIG. 6 shows the anti-proliferative effect of HERCEPTIN® and HERCEPTIN®-DM1 conjugate on SK-BR3 cells in vitro. As control, the unrelated monoclonal antibody RITUXAN® or RITUXAN®-DM1 conjugate was used.

SK-BR3 cells, which express 3+ level of HER2 on cell surface, were treated with HERCEPTIN®, HERCEPTIN®-DM1 conjugate, control mAb RITUXAN® or RITUXAN®-DM1 conjugates, and the effect of these treatments on cell proliferation was monitored. As shown in FIG. 6, the extent of cell growth inhibition by treatment with HERCEPTIN®-DM1 was dramatically more pronounced than that with HERCEPTIN®, while the control RITUXAN® antibody did not inhibit cell growth. Although the RITUXAN®-DM1 did inhibit cell growth, it did so only at high concentrations. For example, the RITUXAN®-DM1 conjugate did not inhibit growth at concentration up to 1 µg/ml. In contrast, the HERCEPTIN®-DM1 conjugate was highly potent and significantly inhibited cell growth starting from 0.01 µg/ml and reaching a plateau at 0.1 µg/ml. The RITUXAN®-DM1 conjugate required 100 times higher concentration to achieve the same level of cell growth inhibition as HERCEPTIN®-DM1 conjugate. This is also reflected in a 100-fold difference in $IC_{50}$ value, concentration required to inhibit cell growth by 50%, of the respective conjugates.

Example 3

Transgenic Animals

In order to improve the clinical activity of HERCEPTIN®, a transgenic HER2 mouse model was developed in which novel HER2-directed therapies could be tested preclinically. Tumors arise readily in transgenic mice that express a mutationally activated form of neu, the rat homolog of HER2, but the HER2 that is overexpressed in breast cancers is not mutated and tumor formation is much less robust in transgenic mice that overexpress nonmutated HER2 (Webster et al., *Semin. Cancer Biol.* 5: 69-76 [1994]). To improve tumor formation with nonmutated HER2, a strategy was used to further enhance overexpression of nonmutated HER2 in a transgenic mouse.

Any promoter that promotes expression of HER2 in epithelial cells in the mouse mammary gland can be used in the disclosed constructs. Many of the milk protein genes are transcribed by promoter/enhancer elements that are specifically active in mammary glands. Milk protein genes include those genes encoding caseins (α–$S_1$ and β), β-lactoglobulin, α-lactalbumin, and whey acidic protein. The ovine β-lactoglobulin promoter is well characterized and widely used in the art (Whitelaw et al., *Biochem J.* 286: 31-39, [1992]). However, similar fragments of promoter DNA from other species are also suitable. A preferred promoter is the promoter derived from the Long Terminal Repeat (LTR) of the Mouse Mammary Tumor Virus (MMTV). A HER2 transgene construct of the present invention was generated using the MMTV LTR promoter.

To improve tumor formation with nonmutated HER2, we have made transgenic mice using a HER2 cDNA plasmid in which an upstream ATG was deleted in order to prevent initiation of translation at such upstream ATG codons, which would otherwise reduce the frequency of translation initiation from the downstream authentic initiation codon of HER2 (for example, see Child et al., *J. Biol. Chem.* 274: 24335-24341 [1999]). Additionally, a chimeric intron was added to the 5' end, which should also enhance the level of expression as reported earlier (Neuberger and Williams, *Nucleic Acids Res.* 16: 6713 [1988]; Buchman and Berg, *Mol. Cell. Biol.* 8: 4395 [1988]; Brinster et al., *Proc. Natl. Acad. Sci. USA* 85: 836 [1988]). The chimeric intron was derived from a Promega vector, pCI-neo mammalian expression vector (bp 890-1022). The cDNA 3'-end is flanked by human growth hormone exons 4 and 5, and polyadenylation sequences. Moreover, FVB mice were used because this strain is more susceptible to tumor development. The promoter from MMTV-LTR was used to ensure tissue-specific HER2 expression in the mammary gland. Animals were fed the AIN 76A diet in order to increase susceptibility to tumor formation (Rao et al., *Breast Cancer Res. and Treatment* 45: 149-158 [1997]). The nucleotide sequence of this transgene plasmid construct (SEQ ID NO: 1) is shown in FIG. 7.

Animals suitable for transgenic experiments can be obtained from standard commercial sources such as Taconic (Germantown, N.Y.). Many strains are suitable, but FVB female mice are preferred because of their higher susceptibility to tumor formation. FVB males were used for mating and vasectomized CD.1 studs were used to stimulate pseudopregnancy. Vasectomized mice can be obtained from any commercial supplier. Founders were bred with either FVB mice or with 129/BL6×FVB p53 heterozygous mice. The mice with heterozygosity at p53 allele were used to potentially increase tumor formation. However, this has proven unnecessary. Therefore, some F1 tumors are of mixed strain. Founder tumors are FVB only. Six founders were obtained with some developing tumors without having litters.

Example 4

HER2 Transgenic Mouse as a Tumor Model to Evaluate HER2-Directed Therapies

Figures 8A, 8B:
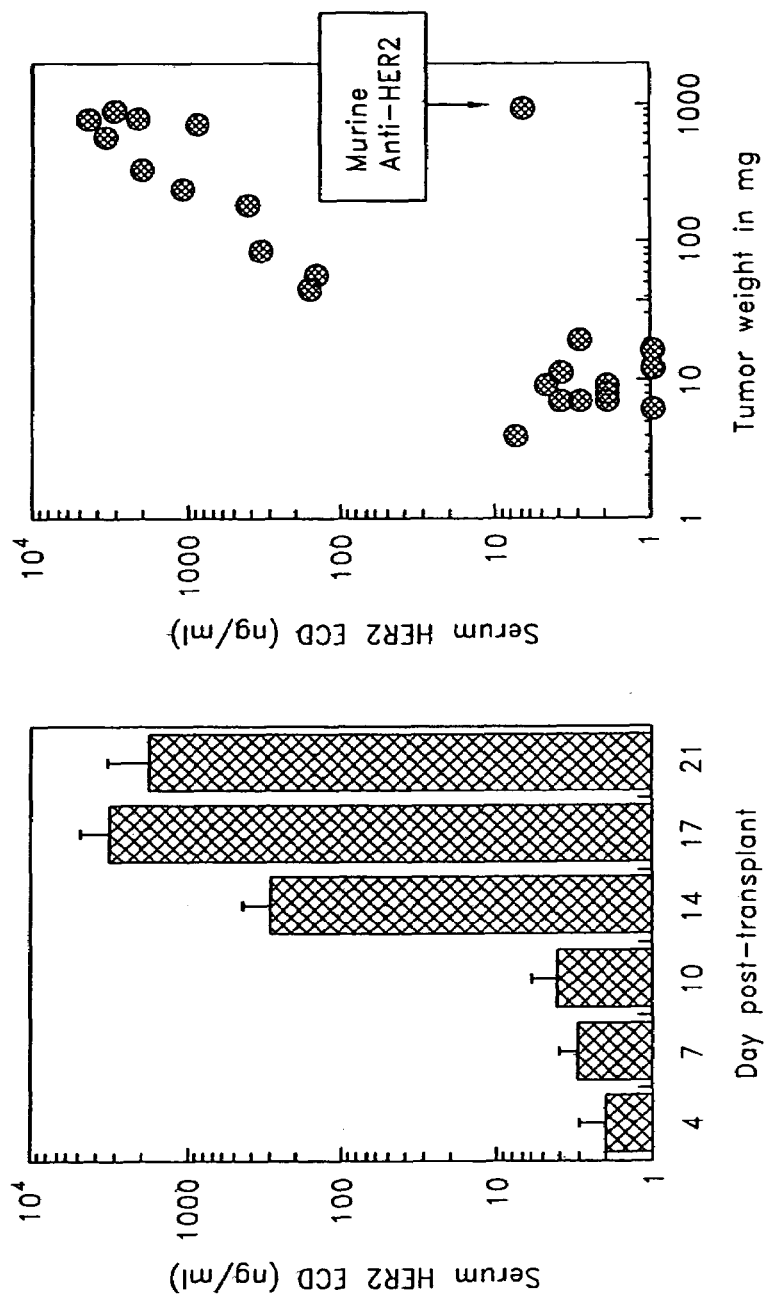
FIGS. 8A and B show that the amount of HER2 extracellular domain (ECD) shed into serum increases following transplant (FIG. 8A) and is proportional to the weight of the resulting tumor (FIG. 8B).

Mammary gland biopsies of one founder transgenic mouse made as described in Example 3, showed 3+ expression of HER2, as determined by immunohistochemical staining, at about 2 months of age. The amount of HER2 extracellular domain (ECD) shed into serum was measured and found to be about 1.2 ng/ml (Huang et al., supra). This mouse subsequently developed a mammary tumor at 5 months of age, after bearing 4 litters. The tumor was surgically resected under aseptic conditions and minced into small pieces, 2 mm³, which were then transplanted into the mammary fat pad of wild-type FVB female mice. As can be seen in FIG. 8A, the amount of HER2 ECD shed into serum increased over time following transplant and was found to be directly proportional to the weight of the tumor that developed (FIG. 8B). Tumors developed in 22 of 31 recipient mice, with a latency of 5 weeks. With subsequent passage, tumors developed with shorter latency and grew more rapidly, and tumor incidence increased to >95% of recipients. HER2 expression, as determined by immunohistochemical staining, was 3+ but heterogeneous in the primary tumor, but became uniformly 3+ after the first passage.

Figure 9:
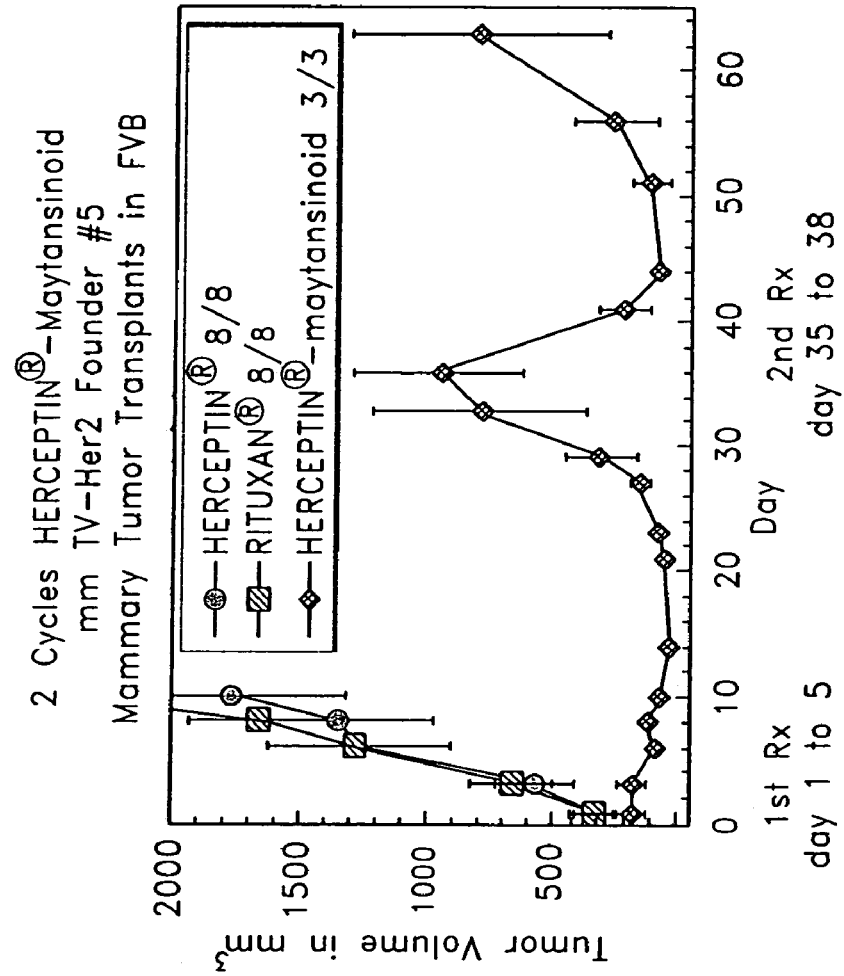
FIG. 9 illustrates the effect of HERCEPTIN®-DM1 on HER2-transgenic tumors. Two $mm^3$ pieces of MMTV-HER2-transgenic tumors were transplanted into the mammary fat pad of FVB mice. When tumors reached 250 $mm^3$, groups of 8 mice were injected i.v. on 5 consecutive days with a HERCEPTIN®-DM1 conjugate. Two other groups of mice were treated IP twice per week with 10 mg/kg of either HERCEPTIN® or RITUXAN®.
Figure 10:
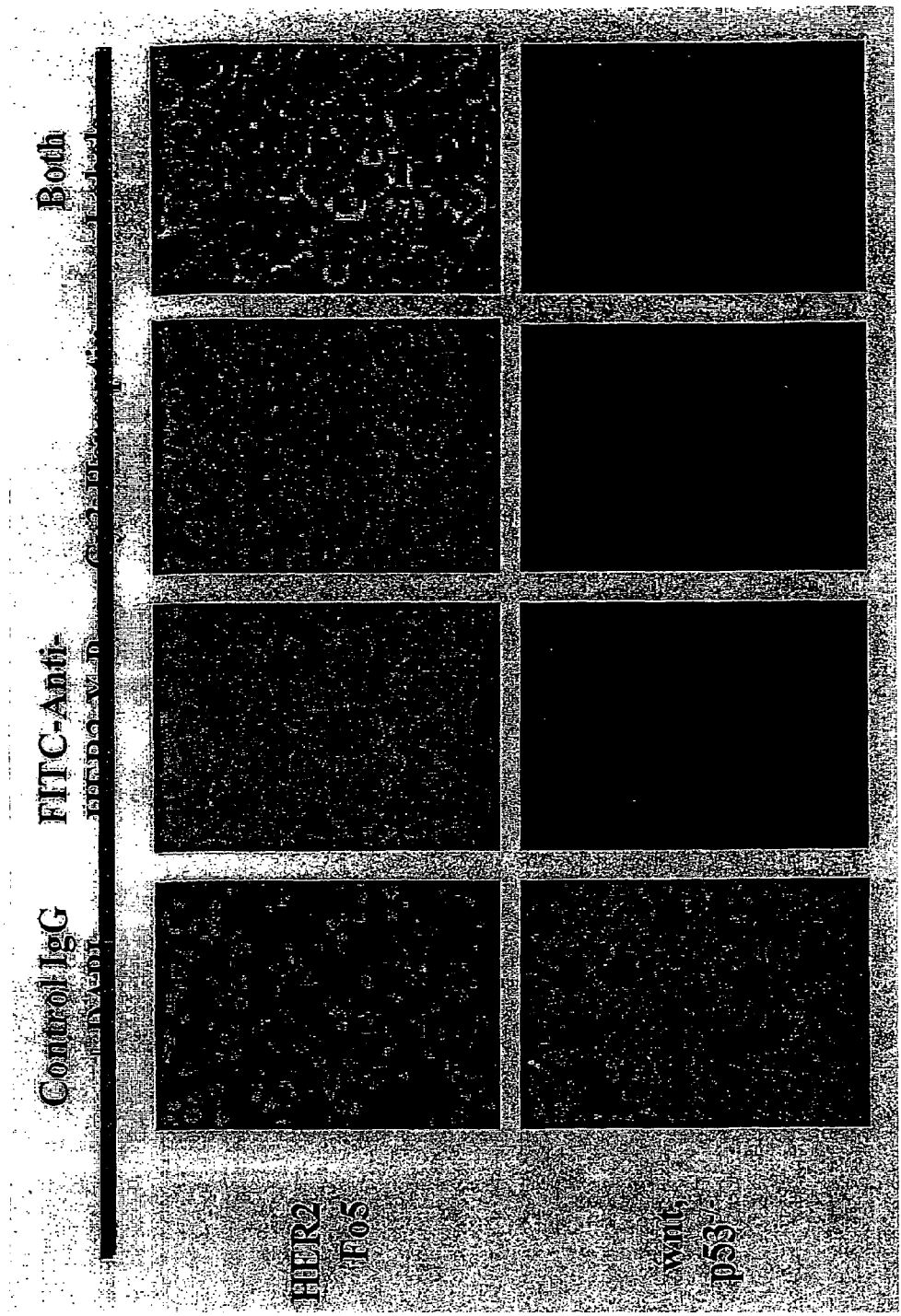
FIG. 10 shows that tumor cells originating from Founder 5 show binding to cy3-HERCEPTIN® and to an anti-tyrosine-phosphorylated-HER2 antibody. Antibodies were injected intravenously into transgenic mice and the next day tumors were collected and sectioned. Antibody binding was visualized by fluoresence microscopy.

Treatment of tumor-bearing mice with HERCEPTIN® or 4D5, the murine antibody from which humanized HERCEPTIN® was derived, had only a is modest effect on the growth of the transplanted tumors (FIG. 9). HER2 expression was 3+ in tumors that grew during HERCEPTIN® or 4D5 therapy, indicating that there was no selection of HER2-negative tumors. Moreover, as can be seen in FIG. 10, cy3-HERCEPTIN® was detected decorating tumor cells after injection into tumor-bearing mice, indicating that the lack of efficacy was not due to failure of the antibody to access the tumor. In addition, HER2 appears to be activated in the tumor cells, as evidenced by the binding of an anti-tyrosine phosphorylated HER2 antibody (FIG. 10).

Based on the persistent expression of HER2 and the failure of this tumor model to respond to HERCEPTIN®, a novel approach was tested, using HERCEPTIN® conjugated to maytansinoid DM1 as described in Example 3. FIG. 9 shows that the HERCEPTIN®-DM1 conjugate has dramatic anti-tumor activity in this model. RITUXAN®, an unrelated anti-CD20 monoclonal antibody, was used as a negative control for these studies. There was little response to HERCEPTIN® compared to the control antibody, RITUXAN®, but there was striking anti-tumor activity of the maytansinoid conjugate of HERCEPTIN®. As shown in FIG. 9, all of the mice treated with HERCEPTIN®-maytansinoid showed striking shrinkage of their tumors, though none of the tumors disappeared. After approximately 4 weeks, tumors began to regrow. Five animals were sacrificed at this time. Their tumors were found to express HER2 at 3+ levels. Thus, there was no selection for HER2-negative tumors. Based on this observation, the remaining 3 mice were treated with HERCEPTIN®-maytansinoid for 5 consecutive days. The tumors again regressed in response to the treatment.

Despite its effectiveness at shrinking tumors and suppressing tumor growth, HERCEPTIN®-DM1 does not kill normal human cells, indicating a selective activity. The effect of various concentrations of HERCEPTIN®-DM1 on human mammary epithelial cells, human hepatocytes and human small airway epithelial cells was investigated. At antibody concentrations of up to 10 µg/ml, the conjugate had no significant effect on cell number.

The pharmacokinetics of HERCEPTIN®-DM1 was evaluated in mice and cynomolgous monkeys. It was determined that the HERCEPTIN®-DM1 pharmacokinetics was linear with respect to dose in both mouse and cynomolgous monkeys following i.v. administration. Dose response analysis in mice indicated that tumor suppression increased with increasing exposure to HERCEPTIN®-DM1 and reached maximum suppression following a dose of at least 18 mg/kg given once a week. The concentration-effect relationship will be further characterized in future studies.

Figure 11:
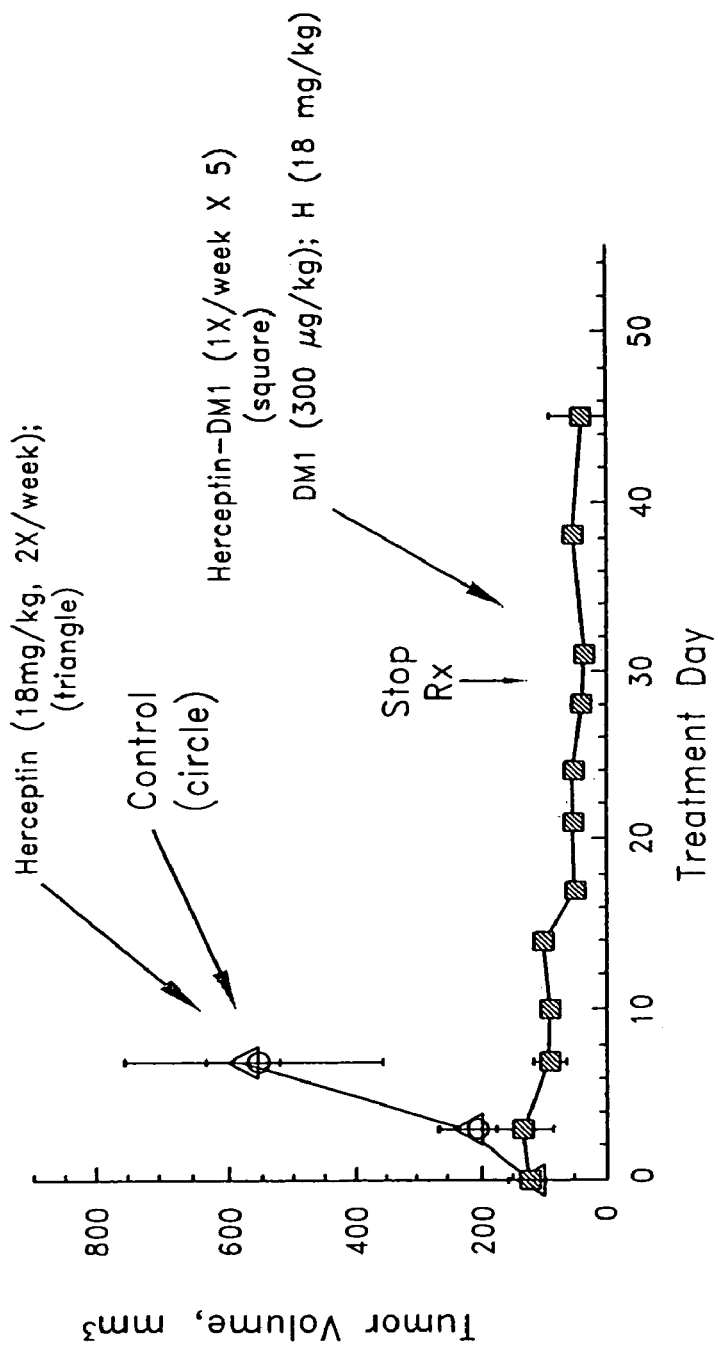
FIG. 11 shows the effect of HERCEPTIN® and HERCEPTIN®-DM1 conjugate on the growth of HER2 transgenic tumor transplant. HERCEPTIN®-DM1 was administered once a week for 5 weeks at 300 µg DM1/kg or 18 mg/kg of HERCEPTIN®. HERCEPTIN® or a control mAb (RITUXAN®) was administered twice a week at 18 mg/kg.

FIG. 11 shows the results of treating mice with HER-2 over-expressing tumors with HERCEPTIN®-DM1 once a week for 5 weeks. Each dose contained 300 µg/kg of DM1 and 18 mg/kg of HERCEPTIN®. Another group of animals received HERCEPTIN® twice a week at a dose of 18 mg/kg body weight. Animals that did not receive any treatment were used as control. As shown in FIG. 11, in animals that received HERCEPTIN®-DM1 tumor size was dramatically controlled and, perhaps more importantly, the tumor size was kept under control even after the therapy was stopped.

Figure 12:
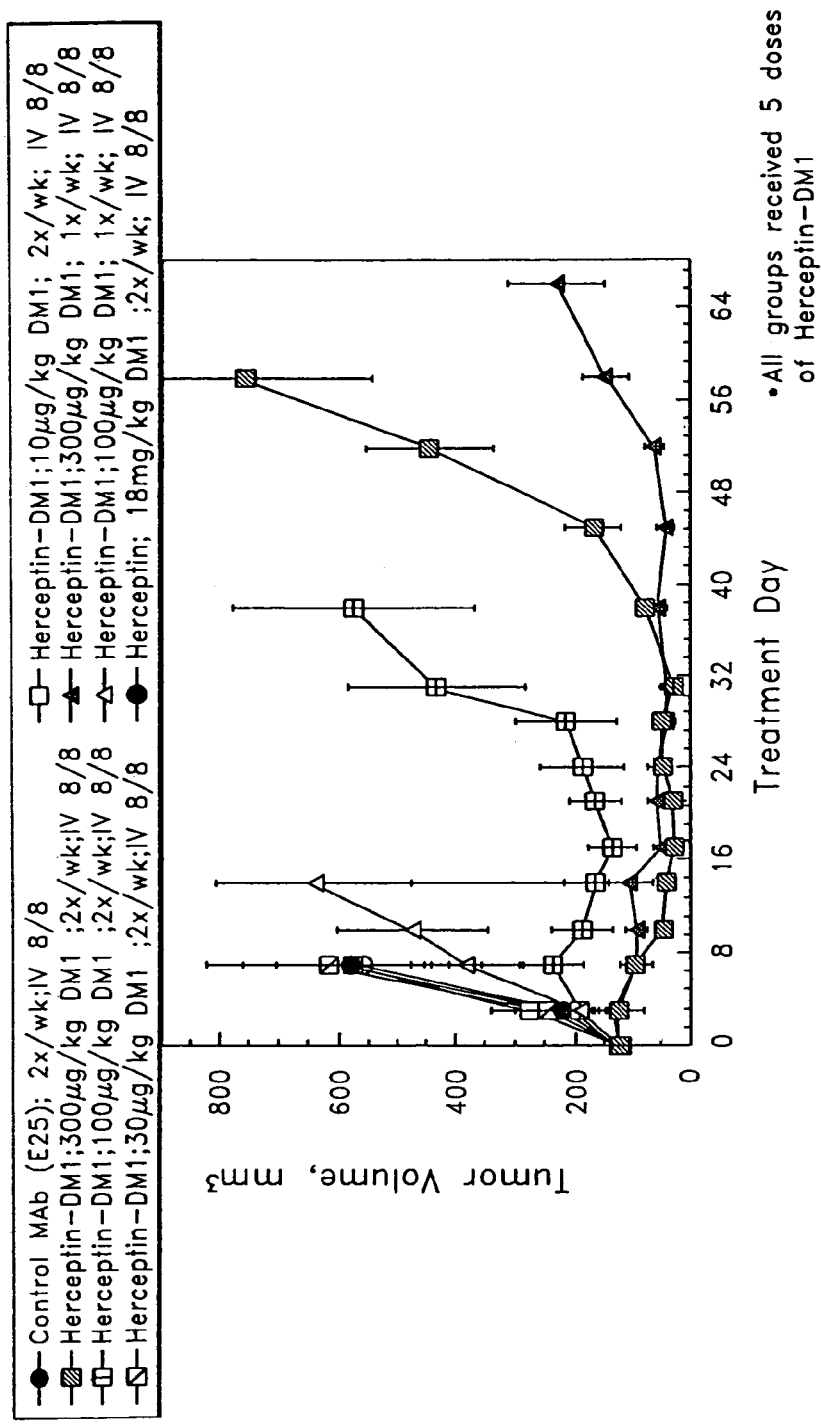
FIG. 12 shows evaluation of doses and schedule of treatment with HERCEPTIN®-DM1 conjugate in HER2 transgenic tumor transplant in nude mice. HERCEPTIN®-DM1 conjugate was administered either twice a week at various doses (300, 100, 30 or 10 µg DM1/kg) or once a week at various doses (300 or 100 µg DM1/kg) for 5 weeks. HERCEPTIN® or a control mAb E25 (RITUXAN®) was administered twice a week at 18 mg/kg.

In yet another experiment, the amount of HERCEPTIN®-DM1 conjugate as well as the frequency of administration were varied while keeping the total number of doses at five. The evaluation was carried out in nude mice containing HER2 tumor transplants in mammary pads. As shown in FIG. 12, some animals received HERCEPTIN®-DM1 at 300, 100, 30 or 10 µg DM1/kg twice a week for the total of 5 doses. Another group of animals received HERCEPTIN®-DM1 at 300 or 100 µg DM1/kg once a week for the total of 5 doses. For comparison, HERCEPTIN® alone was administered at 18 mg/kg twice a week or a control monoclonal antibody (E25 directed against CD20, also known as RITUXAN®) was administered twice a week. Consistent with earlier results in this HERCEPTIN® insensitive model, HERCEPTIN® failed to control the growth of mammary tumors. However, HERCEPTIN®-DM1 conjugate showed dramatic anti-tumor activity in a dose-dependent manner. For example, higher doses showed more potent anti-tumor activity than lower doses in both of the groups, i.e. those receiving treatments twice a week and once a week. Furthermore, twice a week treatment was more effective in keeping the tumor size smaller than once a week treatment schedule. Interestingly, however, there was no significant difference in the profile of tumor growth inhibition at 300 µg DM1/kg dose of HERCEPTIN®-DM1 conjugate whether administered twice a week or once a week. This suggests that at 300 µg DM1/kg dose, once a week schedule of treatment is effective in controlling tumor growth and that a higher frequency of administration is not necessary.

Figure 13:
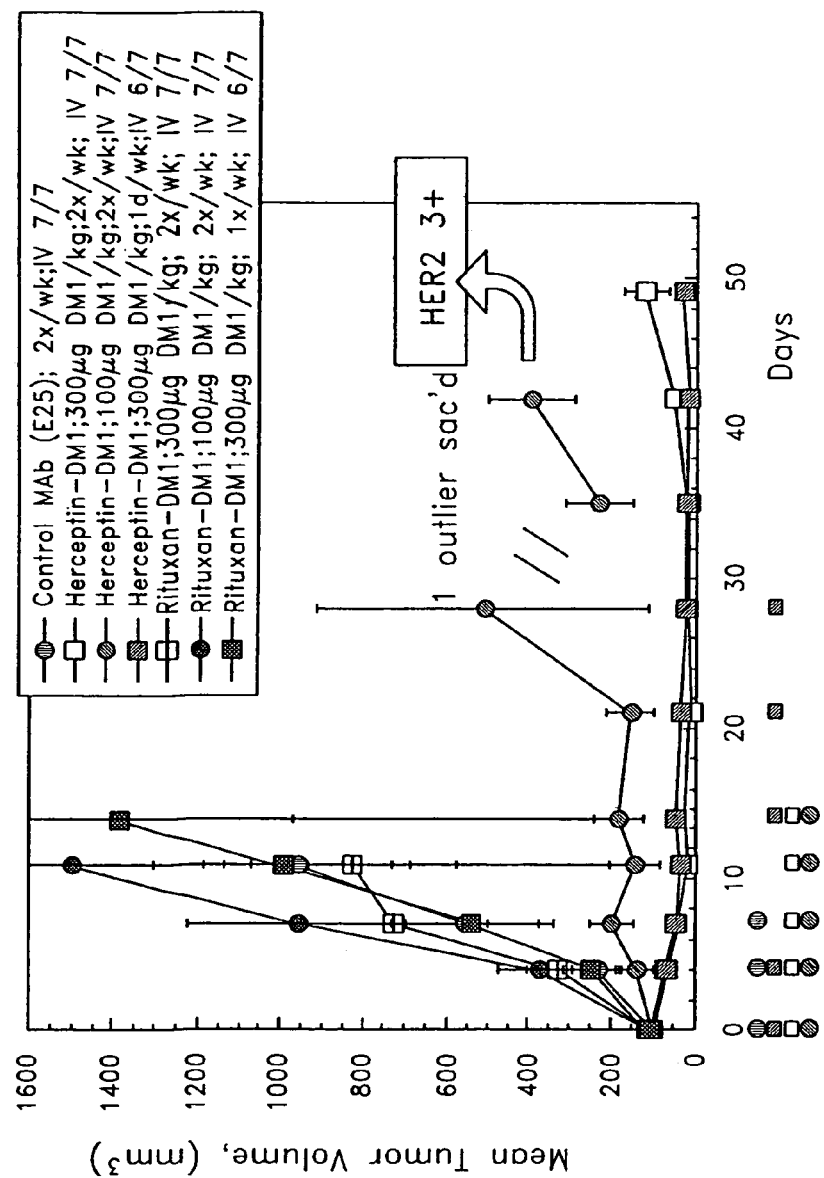
FIG. 13 shows the effect of different HERCEPTIN®-DM1 dosing regimens on HER2-transgenic tumors compared to matching doses of RITUXAN®-DM1. Mice with 100 $mm^3$ tumors were injected i.v. with HERCEPTIN®-DM1 or RITUXAN®-DM1 at doses of 100 or 300 µg DM1/kg twice a week or 300 µg DM1/kg once a week. All animals received 5 doses.

The results of a similar experiment are depicted in FIG. 13. The results of three different dosing regimens of HERCEPTIN®-DM1 conjugate on tumor size are shown compared to matching dosing regimens of RITUXAN®-DM1. Tumor size was reduced and tumor growth was suppressed for at least about 50 days by treatment with 5 doses of HERCEPTIN®-DM1 at a concentration of 300 µg DM1/kg. This was true both when the HERCEPTIN®-DM1 was administered once a week and when it was administered twice a week. By contrast, administration of 5 doses of HERCEPTIN®-DM1 twice a week at a concentration of 100 µg DM1/kg did not shrink tumor size and suppressed tumor growth for somewhat less time. Matched RITUXAN®-DM1 treatment showed little effect on tumor size, indicating that the observed effect is specific to HERCEPTIN®-DM1. Similarly, unconjugated RITUXAN® (control MAb E25) showed no efficacy.

Figure 14:
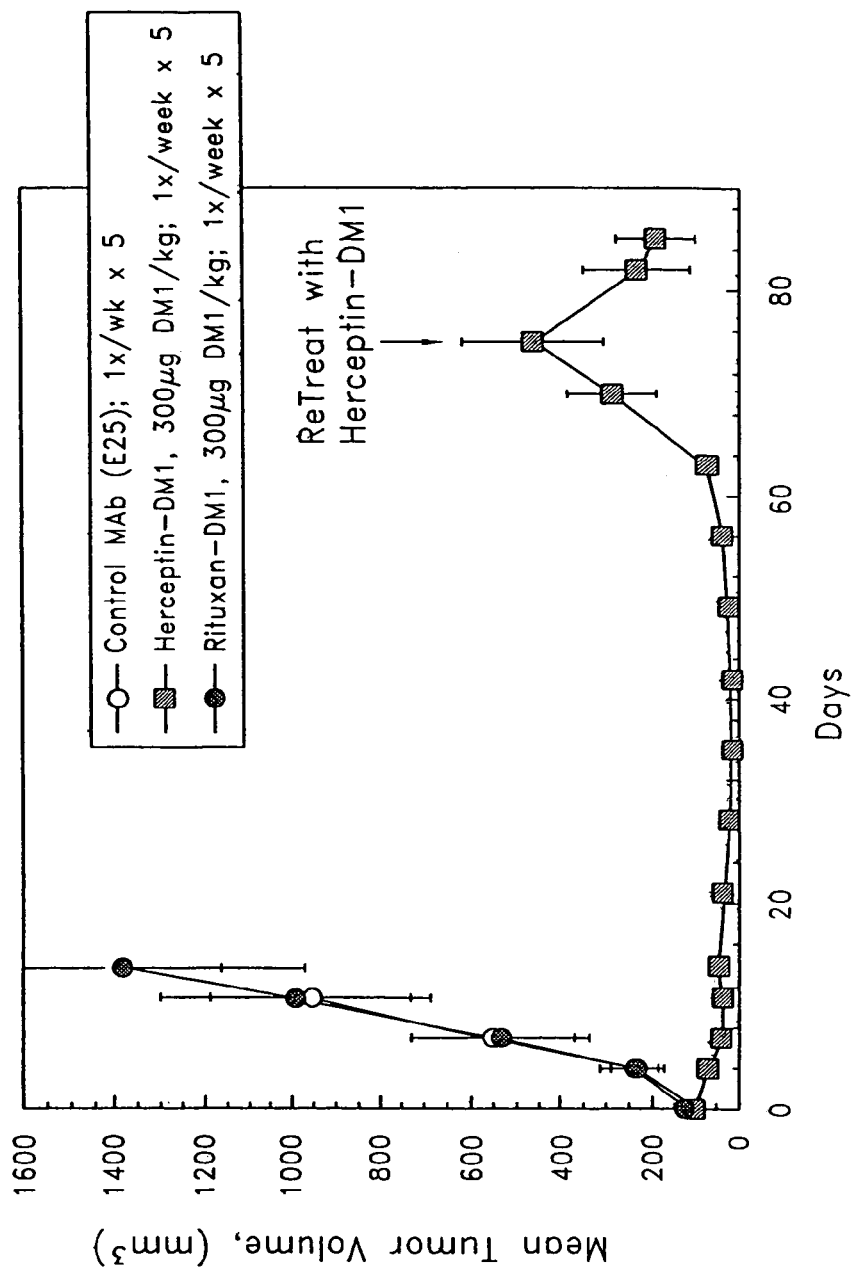
FIG. 14 is a comparison of the most effective observed dose of HERCEPTIN®-DM1 and RITUXAN®-DM1. A second dose of HERCEPTIN®-DM1 following the beginning of tumor regrowth was effective in shrinking the tumors again.

As can be seen clearly in FIG. 14, a dose of HERCEPTIN®-DM1 (300 µg DM1/kg) once a week for five weeks caused tumors to shrink and prevented regrowth for more than 60 days. FIG. 14 also shows that a second round of treatment with HERCEPTIN®-DM1 after tumor regrowth begins is capable of shrinking tumors a second time. Neither unconjugated RITUXAN® (control MAb E25) nor RITUXAN®-DM1 had any obvious effect on tumor growth.

As shown here, the mammary tumor transplanted from HER2 transgenic mouse serves as a very useful model in evaluating various anti-tumor compounds as well as in establishing efficacy of different treatment regimens in preclinical studies. The model is particularly unique as it shares an important attribute of a fraction of human mammary tumors which are either completely or partially refractory to the treatment of HERCEPTIN® inspite of overexpression of HER2 at 2+ or 3+ levels. Thus, HER2 transgenic model described herein provides a valuable tool not only to study the mechanism of resistance to the anti-tumor activity of HERCEPTIN®, but also for screening compounds or modified HERCEPTIN®, including conjugates, for anti-tumor activity. The insight gained from such studies is likely to help in developing effective breast cancer therapies with broad coverage including HERCEPTIN®-resistant metastatic HER2 overexpressing breast carcinomas. The present HER2 transgenic model is particularly suited for preclinical research as well as drug development, and is a better alternative to in vitro studies carried out using breast carcinoma cell lines. It is an in vivo system with normal stroma and microenvironment of breast epithelium with cell-cell and cell-matrix interactions that are typical of a tissue. It also takes into account local factors and cytokines produced in the normal course of mammary gland development and attendant regulatory networks. It is also suitable to carry out pharmacokinetics studies of drug candidates at a smaller scale, which can then be scaled up for studies in non-human primate models. The results provide a sound basis for actual clinical trials in human subjects. As per the strategy described herein, the development of a HER2 transgenic model does not need to involve any in vitro selection, and requires minimal in vivo selection, the latter being limited to the extent of serial passage of the mammary tissue in order to reduce the duration of time needed to develop tumors and obtaining homogenous overexpression of HER2 in mammary cells. Moreover, breeding of these mice provides a continuous source of tissues for various follow-up or supplemental studies. This is particularly significant since the availability of clinical samples of tissues from breast cancer patients is highly limited.

The HERCEPTIN®-DM1 conjugate as described herein was found to have superior activity over HERCEPTIN® in this HER2 transgenic model that mimics HERCEPTIN®-resistant metastatic HER2 overexpressing breast carcinomas. Approximately, 85% of breast cancer patients either do not respond to HERCEPTIN® therapy or respond poorly. The molecular basis of the resistance is not clearly understood. However, it is not due to a lower level of HER2 expression since these tumors also overexpress HER2 at 2+ or 3+ levels. Nevertheless, this significant proportion of breast cancer patients is not able to avail themselves of the powerful potential of HERECEPTIN® therapy. Preclinical studies carried out using the HERCEPTIN®-insensitive HER2 transgenic mouse model as outlined in this application shows a dramatic response of these tumors to HERCEPTIN®-DM1 conjugate as compared to HERCEPTIN®.

The HERCEPTIN®-DM1 conjugate was found to effectively control the growth of HERCEPTIN®-resistant tumors in a dose-dependent manner at a dosage of 100 µg DM1/kg and above. Administration of the tested conjugate at 300 µg DM1/kg once a week brought about a very impressive inhibition of tumor growth. Five such doses completely prevented the emergence of tumor for more than 60 days, and when the tumor did begin to reemerge, a second round of HERCEPTIN®-DM1 was able to control the growth. This is in contrast with a rapid growth of tumors in animals treated with control monoclonal antibody (RITUXAN®), maytansinoid conjugated control monoclonal antibody (RITUXAN®-DM1) or unconjugated HERCEPTIN®. Thus, the preclinical studies presented herein clearly show that the HERCEPTIN®-DM1 conjugate is able to elicit a dramatic anti-tumor response even in HERCEPTIN®-resistant breast tumors. The better objective response rate obtained with the HERCEPTIN®-DM1 conjugate will allow a higher fraction of breast cancer patients to benefit from this powerful therapy. The fact that the effect of HERCEPTIN®-DM1 is dose-dependent suggests that in an actual clinical setting, the strategy is likely to provide a considerable maneuver of doses to achieve the best anti-tumor activity. Moreover, the duration of anti-tumor response is significantly longer, permitting less frequent administration of the conjugate without compromising the therapeutic efficacy. The resultant cost-effectiveness and convenience is quite significant. Furthermore, the conjugate is likely to improve survival rate among the responders. For example, the median time to disease progression in HERCEPTIN® treated patients was only 3.1 months. With the superior therapeutic efficay of HERCEPTIN®-DM1 as compared to HERCEPTIN®, survival rate is likely to be increased.

All references cited through the specification, and the references cited therein, are hereby expressly incorporated by reference.

Deposit of Biological Material

The following hybridoma cell lines have been deposited with the American Type Culture Collection, 10801 University Boulevard, Manassas, Va. 20110-2209, USA (ATCC):

| Antibody Designation | ATCC No. | Deposit Date |
| --- | --- | --- |
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |
| 2C4 | ATCC HB-12697 | Apr. 8, 1999 |

This deposit was made under the provisions of the Budapest Treaty on the International Recognition of the Deposit of Microorganisms for the Purpose is of Patent Procedure and the Regulations thereunder (Budapest Treaty). This assures maintenance of viable cultures for 30 years from the date of the deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.12 with particular reference to 886 OG 638).

In respect of those designations in which a European patent is sought, a sample of the deposited microorganism will be made available until the publication of the mention of the grant of the European patent or until the date on which the application has been refused or withdrawn or is deemed to be withdrawn, only by the issue of such a sample to an expert nominated by the person requesting the sample. (Rule 28(4) EPC)

The assignee of the present application has agreed that if the cultures on deposit should die or be lost or destroyed when cultivated under suitable conditions, they will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the constructs deposited, since the deposited embodiments are intended to illustrate only certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that they represent. Indeed, various modifications of the invention in addition to those shown and described herein will become apparent to those skilled in the art from the foregoing description and fall within the scope of the appended claims.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below, but should not be construed to limit the invention.

SEQUENCE LISTING

<160> NUMBER OF SEQ ID NOS: 11

<210> SEQ ID NO 1
<211> LENGTH: 119
<212> TYPE: PRT
<213> ORGANISM: Artificial Sequence
<220> FEATURE:
<223> OTHER INFORMATION: Humanized Antibody Sequence

<400> SEQUENCE: 1

```
Glu Val Gln Leu Gln Gln Ser Gly Pro Glu Leu Val Lys Pro Gly Thr
 1               5                  10                  15

Ser Val Lys Ile Ser Cys Lys Ala Ser Gly Phe Thr Phe Thr Asp Tyr
            20                  25                  30

Thr Met Asp Trp Val Lys Gln Ser His Gly Lys Ser Leu Glu Trp Ile
        35                  40                  45

Gly Asp Val Asn Pro Asn Ser Gly Gly Ser Ile Tyr Asn Gln Arg Phe
    50                  55                  60

Lys Gly Lys Ala Ser Leu Thr Val Asp Arg Ser Ser Arg Ile Val Tyr
65                  70                  75                  80

Met Glu Leu Arg Ser Leu Thr Phe Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115
```

<210> SEQ ID NO 2
<211> LENGTH: 119
<212> TYPE: PRT
<213> ORGANISM: Artificial Sequence
<220> FEATURE:
<223> OTHER INFORMATION: Humanized Antibody Sequence

<400> SEQUENCE: 2

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

<210> SEQ ID NO 3
<211> LENGTH: 119
<212> TYPE: PRT
<213> ORGANISM: Artificial Sequence
<220> FEATURE:
<223> OTHER INFORMATION: Humanized Antibody Sequence

<400> SEQUENCE: 3

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ala Val Ile Ser Gly Asp Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Val Gly Tyr Ser Leu Tyr Asp Tyr Trp Gly Gln Gly
             100                 105                 110

Thr Leu Val Thr Val Ser Ser
            115
```

<210> SEQ ID NO 4
<211> LENGTH: 109
<212> TYPE: PRT
<213> ORGANISM: Artificial Sequence
<220> FEATURE:
<223> OTHER INFORMATION: Humanized Antibody Sequence

<400> SEQUENCE: 4

```
Asp Thr Val Met Thr Gln Ser His Lys Ile Met Ser Thr Ser Val Gly
  1               5                  10                  15

Asp Arg Val Ser Ile Thr Cys Lys Ala Ser Gln Asp Val Ser Ile Gly
             20                  25                  30

Val Ala Trp Tyr Gln Gln Arg Pro Gly Gln Ser Pro Lys Leu Leu Ile
         35                  40                  45

Tyr Ser Ala Ser Tyr Arg Tyr Thr Gly Val Pro Asp Arg Phe Thr Gly
     50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln Tyr Tyr Ile Tyr Pro Tyr
                 85                  90                  95

Thr Phe Gly Gly Gly Thr Lys Leu Glu Ile Lys Arg Thr
             100                 105
```

<210> SEQ ID NO 5
<211> LENGTH: 109
<212> TYPE: PRT
<213> ORGANISM: Artificial Sequence
<220> FEATURE:
<223> OTHER INFORMATION: Humanized Antibody Sequence

<400> SEQUENCE: 5

```
Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Val Ser Ile Gly
             20                  25                  30

Val Ala Trp Tyr Gln Gln Lys Pro Gly Lys Ala Pro Lys Leu Leu Ile
         35                  40                  45

Tyr Ser Ala Ser Tyr Arg Tyr Thr Gly Val Pro Ser Arg Phe Ser Gly
     50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr
            100                 105
```

<210> SEQ ID NO 6
<211> LENGTH: 109
<212> TYPE: PRT
<213> ORGANISM: Artificial Sequence
<220> FEATURE:
<223> OTHER INFORMATION: Humanized Antibody Sequence

<400> SEQUENCE: 6

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys Arg Thr
            100                 105
```

<210> SEQ ID NO 7
<211> LENGTH: 9274
<212> TYPE: DNA
<213> ORGANISM: Artificial Sequence
<220> FEATURE:
<223> OTHER INFORMATION: Vector Sequence

<400> SEQUENCE: 7

```
aagctcgatc ggtgcacatt aattcatgat cgcgagctag cagcttgcat gcctgcagca     60
gaaatggttg aactcccgag agtgtcctac acctagggga gaagcagcca aggggttgtt    120
tcccaccaag gacgacccgt ctgcgcacaa acggatgagc ccatcagaca agacatatt     180 cattctctgc tgcaaacttg gcatagctct gctttgctgg ggcattgggg gaagttgcgg    240
ttcgtgctcg cagggctctc acccttgact cttttaatag ctcttctgtg caagattaca    300
atctaaacaa ttcggagaac tcgaccttcc tctcctgagg caaggaccac agccaacttc    360
ctcttacaag ccgcatcgat tttgtccttc agaaatagaa ataagaatgc ttgctaaaaa    420
ttatattttt accaataaga ccaatccaat aggtagatta ttagttacta tgttaagaaa    480
tgaatcatta tcttttagta ctattttac tcaaattcag aagttagaaa tgggaataga    540
aaatagaaag agacgctcaa cctcaattga agaacaggtg caaggactat tgaccacagg    600
cctagaagta aaaagggaa aaaagagtgt ttttgtcaaa ataggagaca ggtggtggca    660
accagggact tataggggac cttacatcta cagaccaaca gatgcccct taccatatac    720 aggaagatat gacttaaatt gggataggtg ggttacagtc aatggctata agtgttata    780 tagatccctc ccttttcgtg aaagactcgc cagagctaga cctccttggt gtatgttgtc    840
tcaagaagaa aaagacgaca tgaaacaaca ggtacatgat tatatttatc taggaacagg    900
```

```
aatgcacttt tggggaaaga ttttccatac caaggagggg acagtggctg gactaataga       960
acattattct gcaaaaactt atggcatgag ttattatgaa tagcctttat tggcccaacc      1020
ttgcggttcc caaggcttaa gtaagttttt ggttacaaac tgttcttaaa acgaggatgt      1080
gagacaagtg gtttcctgac ttggtttggt atcaaaggtt ctgatctgag ctctgagtgt      1140
tctatttttcc tatgttcttt tggaatttat ccaaatctta tgtaaatgct tatgtaaacc      1200
aagatataaa agagtgctga tttttgagt aaacttgcaa cagtcctaac attcacctct       1260
tgtgtgtttg tgtctgttcg ccatcccgtc tccgctcgtc acttatcctt cactttccag      1320
agggtccccc cgcagacccc ggatcgctag ctcgcgaatc gataagcttg cggccgctta      1380
actgcagaag ttggtcgtga ggcactgggc aggtaagtat caaggttaca agacaggttt      1440
aaggagacca atagaaactg ggcttgtcga gacagagaag actcttgcgt ttctgatagg      1500
cacctattgg tcttactgac atccactttg cctttctctc cacaggtgtc cactcccagg      1560
ttcaattaca gctcttaagc ggccgcaagc ttgatatcga attcctgcag cccgggggat      1620
ccactagtgg atccaaagaa ttcaaaaagc ttctcgaggg cgcgcgcccg gccccacccc      1680
ctcgcagcac cccgcgcccc gcgccctccc agccgggtcc agccggagcc atggagctgg      1740
cggccttgtg ccgctggggg ctcctcctcg ccctcttgcc ccccggagcc gcgagcaccc      1800
aagtgtgcac cggcacagac atgaagctgc ggctccctgc cagtcccgag acccacctgg      1860
acatgctccg ccacctctac cagggctgcc aggtggtgca gggaaacctg gaactcacct      1920
acctgcccac caatgccagc ctgtccttcc tgcaggatat ccaggaggtg cagggctacg      1980
tgctcatcgc tcacaaccaa gtgaggcagg tcccactgca gaggctgcgg attgtgcgag      2040
gcacccagct cttttgaggac aactatgccc tggccgtgct agacaatgga gacccgctga      2100
acaataccac ccctgtcaca ggggcctccc caggaggcct gcgggagctg cagcttcgaa      2160
gcctcacaga gatcttgaaa ggaggggtct tgatccagcg gaaccccag ctctgctacc       2220
aggacacgat tttgtggaag gacatcttcc acaagaacaa ccagctggct ctcacactga      2280
tagacaccaa ccgctctcgg gcctgccacc cctgttctcc gatgtgtaag ggctcccgct      2340
gctggggaga gagttctgag gattgtcaga gcctgacgcg cactgtctgt gccggtggct      2400
gtgcccgctg caaggggcca ctgcccactg actgctgcca tgagcagtgt gctgccggct      2460
gcacgggccc caagcactct gactgcctgg cctgcctcca cttcaaccac agtggcatct      2520
gtgagctgca ctgcccagcc ctggtcacct acaacacaga cacgtttgag tccatgccca      2580
atccccgaggg ccggtataca ttcggcgcca gctgtgtgac tgcctgtccc tacaactacc      2640
tttctacgga cgtgggatcc tgcacccctcg tctgccccct gcacaaccaa gaggtgacag      2700
cagaggatgg aacacagcgg tgtgagaagt gcagcaagcc ctgtgcccga gtgtgctatg      2760
gtctgggcat ggagcacttg cgagaggtga gggcagttac cagtgccaat atccaggagt      2820
ttgctggctg caagaagatc tttgggagcc tggcatttct gccggagagc tttgatgggg      2880
acccagcctc caacactgcc ccgctccagc cagagcagct ccaagtgttt gagactctgg      2940
aagagatcac aggttaccta tacatctcag catggccgga cagcctgcct gacctcagcg      3000
tcttccagaa cctgcaagta atccggggac gaattctgca caatggcgcc tactcgctga      3060
ccctgcaagg gctgggcatc agctggctgg ggctgcgctc actgagggaa ctgggcagtg      3120
gactggccct catccaccat aacacccacc tctgcttcgt gcacacggtg ccctgggacc      3180
agctcttcocg gaacccgcac caagctctgc tccacactgc caaccggcca gaggacgagt      3240
gtgtgggcga gggcctggcc tgccaccagc tgtgcgcccg agggcactgc tggggtccag      3300
```

-continued

```
ggcccaccca gtgtgtcaac tgcagccagt tccttcgggg ccaggagtgc gtggaggaat    3360
gccgagtact gcaggggctc cccagggagt atgtgaatgc caggcactgt ttgccgtgcc    3420
accctgagtg tcagcccag aatggctcag tgacctgttt tggaccggag gctgaccagt    3480
gtgtggcctg tgcccactat aaggaccctc ccttctgcgt ggcccgctgc cccagcggtg    3540
tgaaacctga cctctcctac atgcccatct ggaagtttcc agatgaggag ggcgcatgcc    3600
agccttgccc catcaactgc acccactcct gtgtggacct ggatgacaag ggctgccccg    3660
ccgagcagag agccagccct ctgacgtcca tcgtctctgc ggtggttggc attctgctgg    3720
tcgtggtctt gggggtggtc tttgggatcc tcatcaagcg acggcagcag aagatccgga    3780
agtacacgat gcggagactg ctgcaggaaa cggagctggt ggagccgctg acacctagcg    3840
gagcgatgcc caaccaggcg cagatgcgga tcctgaaaga gacggagctg aggaaggtga    3900
aggtgcttgg atctggcgct tttggcacag tctacaaggg catctggatc cctgatgggg    3960
agaatgtgaa aattccagtg gccatcaaag tgttgaggga aaacacatcc cccaaagcca    4020
acaaagaaat cttagacgaa gcatacgtga tggctggtgt gggctcccca tatgtctccc    4080
gccttctggg catctgcctg acatccacgg tgcagctggt gacacagctt atgccctatg    4140
gctgcctctt agaccatgtc cgggaaaacc gcggacgcct gggctcccag gacctgctga    4200
actggtgtat gcagattgcc aagggatga gctacctgga ggatgtgcgg ctcgtacaca    4260
gggacttggc cgctcggaac gtgctggtca agagtcccaa ccatgtcaaa attacagact    4320
tcgggctggc tcggctgctg gacattgacg agacagagta ccatgcagat ggggcaagg    4380
tgcccatcaa gtggatggcg ctggagtcca ttctccgccg gcggttcacc caccagagtg    4440
atgtgtggag ttatggtgtg actgtgtggg agctgatgac tttggggcc aaaccttacg    4500
atgggatccc agcccgggag atccctgacc tgctggaaaa gggggagcgg ctgccccagc    4560
cccccatctg caccattgat gtctacatga tcatggtcaa atgttggatg attgactctg    4620
aatgtcggcc aagattccgg gagttggtgt ctgaattctc ccgcatggcc agggaccccc    4680
agcgctttgt ggtcatccag aatgaggact tgggcccagc cagtccctttg acagcacct    4740
tctaccgctc actgctggag gacgatgaca tgggggacct ggtggatgct gaggagtatc    4800
tggtacccca gcagggcttc ttctgtccag accctgcccc gggcgctggg ggcatggtcc    4860
accacaggca ccgcagctca tctaccagga gtggcggtgg ggacctgaca ctagggctgg    4920
agccctctga agaggaggcc cccaggtctc cactggcacc ctccgaaggg gctggctccg    4980
atgtatttga tggtgacctg ggaatggggg cagccaaggg gctgcaaagc ctccccacac    5040
atgaccccag ccctctacag cggtacagtg aggaccccac agtaccccctg ccctctgaga    5100
ctgatggcta cgttgccccc ctgacctgca gcccccagct gaatatgtg aaccagccag    5160
atgttcggcc ccagcccct tcgccccgag agggccctct gcctgctgcc cgacctgctg    5220
gtgccactct ggaaagggcc aagactctct ccccagggaa gaatgggtc gtcaaagacg    5280
tttttgcctt tgggggtgcc gtggagaacc ccgagtactt gacacccccag ggaggagctg    5340
cccctcagcc ccaccctcct cctgccttca gcccagcctt cgacaacctc tattactggg    5400
accaggaccc accagagcgg ggggctccac ccagcacctt caaagggaca cctacggcag    5460
agaacccaga gtacctgggt ctggacgtgc cagtgtgaac cagaaggcca agtccgcaga    5520
agccctgatg tgtcctcagg gagcaggaa ggcggcctct gagctattcc agaagtagtg    5580
aggaggcttt tttggaggcc taggcttttg caaaaagctt atcgataccg tcgactcgag    5640
agtacttcta gagcggccgc gggcccatcg cctctgacag caacgtctat gacctcctaa    5700
```

```
aggacctaga ggaaggcatc caaacgctga tggggaggct ggaagatggc agccccggga    5760
ctgggcagat cttcaagcag acctacagca agttcgacac aaaactcacac aacgatgacg   5820 cactactcaa gaactacggg ctgctctact gcttcaggaa ggacatggac aaggtcgaga    5880
cattcctgcg catcgtgcag tgccgctctg tggagggcag ctgtggcttc tagctgcccg    5940
ggtggcatcc ctgtgacccc tccccagtgc ctctcctggc cctggaagtt gccactccag    6000
tgcccaccag ccttgtccta ataaaattaa gttgcatcat tttgtctgac taggtgtcct    6060
tctataatat tatggggtgg aggggggtgg tatggagcaa ggggcccaag ttgggaagac    6120
aacctgtagg gcctgcgggg tctattcggg aaccaagctg gagtgcagtg cacaatcttt    6180
ggctcactgc aatctccgcc tcctgggttc aagcgattct cctgcctcag cctcccgagt    6240 tgtgggatt ccaggcatgc atgaccaggc tcagctaatt tttgtttttt tggtagagac     6300
ggggtttcac catattggcc aggctggtct ccaactccta atctcaggtg atctacccac    6360
cttggcctcc caaattgctg ggattacagg cgtgaaccac tgctcccttc cctgtccttc    6420
tgattttaaa ataactatac cagcaggagg acgtccagac acagcatagg ctacctgcca    6480
tggcccaacc ggtgggacat ttgagttgct tgcttggcac tgtcctctca tgcgttgggt    6540
ccactcagta gatgcctgtt gaattacgat cggtgcacat taattcatga aattcgtaat    6600
catggtcata gctgtttcct gtgtgaaatt gttatccgct cacaattcca cacaacatac    6660
gagccggaag cataaagtgt aaagcctggg gtgcctaatg agtgaggtaa ctcacattaa    6720
ttgcgttgcg ctcactgccc gctttccagt cgggaaacct gtcgtgccag ctggattaat    6780
gaatcggcca acgcgcgggg agaggcggtt tgcgtattgg gcgctcttcc gcttcctcgc    6840
tcactgactc gctgcgctcg tcgttcggc tgcggcgagc ggtatcagct cactcaaagg     6900
cggtaatacg gttatccaca gaatcagggg ataacgcagg aaagaacatg tgagcaaaag    6960
gccagcaaaa ggccaggaac cgtaaaaagg ccgcgttgct ggcgttttc cataggctcc     7020 gccccctga cgagcatcac aaaaatcgac gctcaagtca gaggtggcga acccgacag      7080 gactataaag ataccaggcg tttccccctg gaagctccct cgtgcgctct cctgttccga    7140
ccctgccgct taccggatac ctgtccgcct ttctccttc gggaagcgtg gcgctttctc     7200
aatgctcacg ctgtaggtat ctcagttcgg tgtaggtcgt tcgctccaag ctgggctgtg    7260
tgcacgaacc ccccgttcag cccgaccgct gcgccttatc cggtaactat cgtcttgagt    7320
ccaacccggt aagacacgac ttatcgccac tggcagcagc cactggtaac aggattagca    7380
gagcgaggta tgtaggcggt gctacagagt tcttgaagtg gtggcctaac tacggctaca    7440
ctagaaggac agtatttggt atctgcgctc tgctgaagcc agttaccttc ggaaaaagag    7500
ttggtagctc ttgatccggc aaacaaacca ccgctgtag cggtggtttt tttgtttgca     7560
agcagcagat tacgcgcaga aaaaaggat ctcaagaaga tcctttgatc ttttctacgg     7620
ggtctgacgc tcagtggaac gaaaactcac gttaaggat tttggtcatg agattatcaa     7680
aaaggatctt cacctagatc cttttaaatt aaaaatgaag ttttaaatca atctaaagta    7740
tatatgagta aacttggtct gacagttacc aatgcttaat cagtgaggca cctatctcag    7800
cgatctgtct atttcgttca tccatagttg cctgactccc cgtcgtgtag ataactacga    7860
tacgggaggg cttaccatct ggccccagtg ctgcaatgat accgcgagac ccacgctcac    7920
cggctccaga tttatcagca ataaaccagc cagccggaag ggccgagcgc agaagtggtc    7980
ctgcaacttt atccgcctcc atccagtcta ttaattgttg ccgggaagct agagtaagta    8040
gttcgccagt taatagtttg cgcaacgttg ttgccattgc tgctggcatc gtggtgtcac    8100
```

-continued

```
gctcgtcgtt tggtatggct tcattcagct ccggttccca acgatcaagg cgagttacat    8160
gatcccccat gttgtgcaaa aaagcggtta gctccttcgg tcctccgatc gttgtcagaa    8220
gtaagttggc cgcagtgtta tcactcatgg ttatggcagc actgcataat tctcttactg    8280
tcatgccatc cgtaagatgc ttttctgtga ctggtgagta ctcaaccaag tcattctgag    8340
aatagtgtat gcggcgaccg agttgctctt gcccggcgtc atcacgggat aataccgcgc    8400
cacatagcag aactttaaaa gtgctcatca ttggaaaacg ttcttcgggg cgaaaactct    8460
caaggatctt accgctgttg agatccagtt cgatgtaacc cactcgtgca cccaactgat    8520
cttcagcatc ttttactttc accagcgttt ctgggtgagc aaaaacagga aggcaaaatg    8580
ccgcaaaaaa gggaataagg gcgacacgga aatgttgaat actcatactc ttcctttttc    8640
aatattattg aagcatttat cagggttatt gtctcatgag cggatacata tttgaatgta    8700
tttagaaaaa taaacaaata ggggttccgc gcacatttcc ccgaaaagtg ccacctgacg    8760
tctaagaaac cattattatc atgacattaa cctataaaaa taggcgtatc acgaggccct    8820
ttcgtcttca agaatactgc ctcgcgcgtt tcggtgatga cggtgaaaac ctctgacaca    8880
tgcagctccc ggagacggtc acagcttgtc tgtaagcgga tgccgggagc agacaagccc    8940
gtcagggcgc gtcagcgggt gttggcgggt gtcggggcgc agccatgacc cagtcacgta    9000
gcgatagcgg agtggctta actatgcggc atcagagcag attgtactga gagtgcacca    9060
tatgcggtgt gaaataccgc acagatgcgt aaggagaaaa taccgcatca ggcgccattc    9120
gccattcagg ctacgcaact gttgggaagg gcgatcggtg cgggcctctt cgctattacg    9180
ccagctggcg aaggggggat gtgctgcaag gcgattaagt tgggtaacgc cagggttttc    9240
ccagtcacga cgttgtaaaa cgacggccag tgcc                                9274
```

<210> SEQ ID NO 8
<211> LENGTH: 3768
<212> TYPE: DNA
<213> ORGANISM: Homo sapiens
<400> SEQUENCE: 8

```
atggagctgg cggccttgtg ccgctggggg ctcctcctcg ccctcttgcc ccccggagcc      60
gcgagcaccc aagtgtgcac cggcacagac atgaagctgc ggctccctgc cagtcccgag     120
acccacctgg acatgctccg ccacctctac cagggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gaggctgcgg    300
attgtgcgag gcacccagct cttttgagga caactatgccc tggccgtgct agacaatgga    360
gacccgctga caataccacc cctgtcaca ggggcctccc caggaggcct gcgggagctg    420
cagcttcgaa gcctcacaga gatcttgaaa ggaggggtct tgatccagcg gaaccccag    480 ctctgctacc aggacacgat tttgtggaag gacatcttcc acaagaacaa ccagctggct    540
ctcacactga tagacaccaa ccgctctcgg gcctgccacc cctgttctcc gatgtgtaag    600
ggctcccgct gctggggaga gagttctgag gattgtcaga gcctgacgcg cactgtctgt    660
gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgccccct gcacaaccaa    960
```

```
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt tgctggctg caagaagatc tttgggagcc tggcatttct gccggagagc    1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccgggac gaattctgca caatggcgcc    1320
tactcgctga ccctgcaagg gctgggcatc agctggctgg gctgcgctc actgagggaa    1380 ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccaggagt atgtgaatgc caggcactgt    1680
ttgccgtgcc accctgagtg tcagcccag aatggctcag tgacctgttt tggaccggag    1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactcct gtgtggacct ggatgacaag   1920
ggctgccccg ccgagcagag agccagccct ctgacgtcca tcgtctctgc ggtggttggc   1980
attctgctgg tcgtggtctt gggggtggtc tttgggatcc tcatcaagcg acggcagcag   2040
aagatccgga agtacacgat gcggagactg ctgcaggaaa cggagctggt ggagccgctg   2100
acacctagcg gagcgatgcc caaccaggcg cagatgcgga tcctgaaaga cgcgagctg    2160 aggaaggtga aggtgcttgg atctggcgct tttggcacag tctacaaggg catctggatc   2220
cctgatgggg agaatgtgaa aattccagtg gccatcaaag tgttgaggga aaacacatcc   2280
cccaaagcca acaaagaaat cttagacgaa gcatacgtga tggctggtgt gggctcccca   2340
tatgtctccc gccttctggg catctgcctg acatccacgg tgcagctggt gacacagctt   2400 atgcccctatg gctgcctctt agaccatgtc cgggaaaacc gcggacgcct gggctcccag   2460
gacctgctga actggtgtat gcagattgcc aaggggatga gctacctgga ggatgtgcgg   2520
ctcgtacaca gggacttggc cgctcggaac gtgctggtca agagtcccaa ccatgtcaaa   2580
attacagact cgggctggc tcggctgctg acattgacg agacagagta ccatgcagat    2640
gggggcaagg tgcccatcaa gtggatggcg ctggagtcca ttctccgccg gcggttcacc   2700
caccagagtg atgtgtggag ttatggtgtg actgtgtggg agctgatgac ttttggggcc   2760
aaaccttacg atgggatccc agcccgggag atccctgacc tgctggaaaa ggggagcgg   2820 ctgcccagc cccccatctg caccattgat gtctacatga tcatggtcaa atgttggatg   2880
attgactctg aatgtcggcc aagattccgg agttggtgt ctgaattctc ccgcatggcc    2940
agggaccccc agcgctttgt ggtcatccag aatgaggact gggcccagc cagtcccttg    3000 gacagcacct tctaccgctc actgctggag gacgatgaca tggggacct ggtggatgct    3060 gaggagtatc tggtacccca gcagggcttc ttctgtccag accctgcccc gggcgctggg   3120
ggcatggtcc accacaggca ccgcagctca tctaccagga gtggcggtgg ggacctgaca   3180
ctagggctgg agccctctga agaggaggcc cccaggtctc cactggcacc ctccgaaggg   3240
gctggctccg atgtatttga tggtgacctg ggaatggggg cagccaaggg gctgcaaagc   3300 ctcccccacac atgaccccag ccctctacag cggtacagtg aggaccccac agtaccccctg   3360
```

-continued

```
ccctctgaga ctgatggcta cgttgccccc ctgacctgca gcccccagcc tgaatatgtg    3420
aaccagccag atgttcggcc ccagccccct tcgcccccgag agggccctct gcctgctgcc    3480
cgacctgctg gtgccactct ggaaagggcc aagactctct ccccaggaa gaatggggtc      3540 gtcaaagacg tttttgcctt tggggggtgcc gtggagaacc ccgagtactt gacaccccag    3600
ggaggagctg cccctcagcc ccaccctcct cctgccttca gcccagcctt cgacaacctc    3660
tattactggg accaggaccc accagagcgg ggggctccac ccagcacctt caaagggaca    3720
cctacggcag agaacccaga gtacctgggt ctggacgtgc cagtgtga                  3768
```

<210> SEQ ID NO 9
<211> LENGTH: 1255
<212> TYPE: PRT
<213> ORGANISM: Homo sapiens

<400> SEQUENCE: 9

```
Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
             20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
     50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300
```

-continued

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
        340                 345                 350

Val Arg Ala Val Thr Ser Ala Asn Ile Gln Glu Phe Ala Gly Cys Lys
    355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Phe Gln Asn Leu Gln Val Ile Arg
        420                 425                 430

Gly Arg Ile Leu His Asn Gly Ala Tyr Ser Leu Thr Leu Gln Gly Leu
    435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
        500                 505                 510

Gln Leu Cys Ala Arg Gly His Cys Trp Gly Pro Gly Pro Thr Gln Cys
    515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
        580                 585                 590

Pro Pro Phe Cys Val Ala Arg Cys Pro Ser Gly Val Lys Pro Asp Leu
    595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Val Ser
            645                 650                 655

Ala Val Val Gly Ile Leu Leu Val Val Val Leu Gly Val Val Phe Gly
        660                 665                 670

Ile Leu Ile Lys Arg Arg Gln Gln Lys Ile Arg Lys Tyr Thr Met Arg
    675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

```
Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
                755                 760                 765

Asp Glu Ala Tyr Val Met Ala Gly Val Gly Ser Pro Tyr Val Ser Arg
        770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Arg Leu Pro Gln Pro
                930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr Leu
        1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
        1075                1080                1085

Asp Leu Gly Met Gly Ala Ala Lys Gly Leu Gln Ser Leu Pro Thr His
    1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135
```

-continued

Pro Glu Tyr Val Asn Gln Pro Asp Val Arg Pro Gln Pro Pro Ser Pro
         1140                1145                1150

Arg Glu Gly Pro Leu Pro Ala Ala Arg Pro Ala Gly Ala Thr Leu Glu
    1155                1160                1165

Arg Ala Lys Thr Leu Ser Pro Gly Lys Asn Gly Val Val Lys Asp Val
    1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
         1205                1210                1215

Phe Asp Asn Leu Tyr Tyr Trp Asp Gln Asp Pro Glu Arg Gly Ala
         1220                1225                1230

Pro Pro Ser Thr Phe Lys Gly Thr Pro Thr Ala Glu Asn Pro Glu Tyr
         1235                1240                1245

Leu Gly Leu Asp Val Pro Val
    1250                1255

<210> SEQ ID NO 10
<211> LENGTH: 9274
<212> TYPE: DNA
<213> ORGANISM: Artificial Sequence
<220> FEATURE:
<223> OTHER INFORMATION: Vector Sequence

<400> SEQUENCE: 10
ttcgagctag ccacgtgtaa ttaagtacta gcgctcgatc gtcgaacgta cggacgtcgt      60
ctttaccaac ttgagggctc tcacaggatg tggatcccct cttcgtcggt tccccaacaa     120
agggtggttc ctgctgggca gacgcgtgtt tgcctactcg ggtagtctgt ttctgtataa     180
gtaagagacg acgtttgaac cgtatcgaga cgaaacgacc ccgtaacccc cttcaacgcc     240
aagcacgagc gtcccgagag tgggaactga gaaaattatc gagaagacac gttctaatgt     300
tagatttgtt aagcctcttg agctggaagg agaggactcc gttcctggtg tcggttgaag     360
gagaatgttc ggcgtagcta aaacaggaag tctttatctt tattcttacg aacgattttt     420
aatataaaaa tggttattct ggttaggtta tccatctaat aatcaatgat acaattcttt     480
acttagtaat agaaaatcat gataaaaatg agtttaagtc ttcaatcttt acccttatct     540
tttatctttc tctgcgagtt ggagttaact tcttgtccac gttcctgata actggtgtcc     600
ggatcttcat tttttccctt ttttctcaca aaaacagttt tatcctctgt ccaccaccgt     660
tggtccctga atatccccctg gaatgtagat gtctggttgt ctacggggga atggtatatg     720
tccttctata ctgaatttaa ccctatccac ccaatgtcag ttaccgatat ttcacaatat     780
atctagggag ggaaaagcac tttctgagcg gtctcgatct ggaggaacca catacaacag     840
agttcttctt tttctgctgt actttgttgt ccatgtacta atataaatag atccttgtcc     900
ttacgtgaaa acccctttct aaaaggtatg gttcctcccc tgtcaccgac ctgattatct     960
tgtaataaga cgttttttgaa taccgtactc aataatactt atcggaaata accgggttgg    1020
aacgccaagg gttccgaatt cattcaaaaa ccaatgtttg acaagaattt tgctcctaca    1080
ctctgttcac caaaggactg aaccaaacca tagtttccaa gactagactc gagactcaca    1140
agataaaagg atacaagaaa accttaaata ggtttagaat acatttacga atacatttgg    1200
ttctatattt tctcacgact aaaaaactca tttgaacgtt gtcaggattg taagtggaga    1260
acacacaaac acagacaagc ggtagggcag aggcgagcag tgaataggaa gtgaaaggtc    1320
tcccaggggg gcgtctgggg cctagcgatc gagcgcttag ctattcgaac gccggcgaat    1380

```
tgacgtcttc aaccagcact ccgtgacccg tccattcata gttccaatgt tctgtccaaa    1440
ttcctctggt tatctttgac ccgaacagct ctgtctcttc tgagaacgca aagactatcc    1500
gtggataacc agaatgactg taggtgaaac ggaaagagag gtgtccacag gtgagggtcc    1560
aagttaatgt cgagaattcg ccggcgttcg aactatagct taaggacgtc gggcccccta    1620
ggtgatcacc taggtttctt aagttttttcg aagagctccc gcgcgcgggc cggggtggg    1680 gagcgtcgtg gggcgcgggg cgcggaggg tcggcccagg tcggcctcgg tacctcgacc    1740
gccggaacac ggcgaccccc gaggaggagc gggagaacgg ggggcctcgg cgctcgtggg    1800
ttcacacgtg gccgtgtctg tacttcgacg ccgagggacg tcagggctc tgggtggacc    1860 tgtacgaggc ggtggagatg gtcccgacgg tccaccacgt ccctttggac cttgagtgga    1920
tggacgggtg gttacggtcg gacaggaagg acgtcctata ggtcctccac gtcccgatgc    1980
acgagtagcg agtgttggtt cactccgtcc agggtgacgt ctccgacgcc taacacgctc    2040
cgtgggtcga gaaactcctg ttgatacggg accggcacga tctgttacct ctgggcgact    2100
tgttatggtg gggacagtgt ccccggaggg gtcctccgga cgccctcgac gtcgaagctt    2160
cggagtgtct ctagaacttt cctccccaga actaggtcgc cttggggtc gagacgatgg    2220 tcctgtgcta aaacaccttc ctgtagaagg tgttcttgtt ggtcgaccga gagtgtgact    2280
atctgtggtt ggcgagagcc cggacggtgg ggacaagagg ctacacattc cgagggcga    2340 cgaccctct ctcaagactc ctaacagtct cggactgcgc gtgacagaca cggccaccga    2400
cacgggcgac gttccccggt gacgggtgac tgacgacggt actcgtcaca cgacggccga    2460
cgtgcccggg gttcgtgaga ctgacggacc ggacggaggt gaagttggtg tcaccgtaga    2520
cactcgacgt gacgggtcgg gaccagtgga tgttgtgtct gtgcaaactc aggtacgggt    2580
tagggctccc ggccatatgt aagccgcggt cgacacactg acggacaggg atgttgatgg    2640
aaagatgcct gcaccctagg acgtgggagc agacggggga cgtgttggtt ctccactgtc    2700
gtctcctacc ttgtgtcgcc acactcttca cgtcgttcgg gacacgggct cacacgatac    2760
cagacccgta cctcgtgaac gctctccact cccgtcaatg gtcacggtta taggtcctca    2820
aacgaccgac gttcttctag aaaccctcgg accgtaaaga cggcctctcg aaactacccc    2880
tgggtcggag gttgtgacgg ggcgaggtcg gtctcgtcga ggttcacaaa ctctgagacc    2940
ttctctagtg tccaatggat atgtagagtc gtaccggcct gtcggacgga ctggagtcgc    3000
agaaggtctt ggacgttcat taggcccctg cttaagacgt gttaccgcgg atgagcgact    3060
gggacgttcc cgacccgtag tcgaccgacc ccgacgcgag tgactccctt gacccgtcac    3120
ctgaccggga gtaggtggta ttgtgggtgg agacgaagca cgtgtgccac gggaccctgg    3180
tcgagaaagc cttgggcgtg gttcgagacg aggtgtgacg gttggccggt ctcctgctca    3240
cacacccgct cccggaccgg acggtggtcg acacgcgggc tcccgtgacg accccaggtc    3300
ccgggtgggt cacacagttg acgtcggtca aggaagcccc ggtcctcacg cacctcctta    3360
cggctcatga cgtccccgag gggtccctca tacacttacg gtccgtgaca acggcacgg    3420 tgggactcac agtcggggtc ttaccgagtc actggacaaa acctggcctc cgactggtca    3480
cacaccggac acgggtgata ttcctgggag ggaagacgca ccgggcgacg gggtcgccac    3540
actttggact ggagaggatg tacgggtaga ccttcaaagg tctactcctc ccgcgtacgg    3600
tcggaacggg gtagttgacg tgggtgagga cacacctgga cctactgttc ccgacggggc    3660
ggctcgtctc tcggtcggga gactgcaggt agcagagacg ccaccaaccg taagacgacc    3720
agcaccagaa ccccaccag aaaccctagg agtagttcgc tgccgtcgtc ttctaggcct    3780
```

-continued

```
tcatgtgcta cgcctctgac gacgtcctttt gcctcgacca cctcggcgac tgtggatcgc   3840
ctcgctacgg gttggtccgc gtctacgcct aggactttct ctgcctcgac tccttccact   3900
tccacgaacc tagaccgcga aaaccgtgtc agatgttccc gtagacctag ggactacccc   3960
tcttacactt ttaaggtcac cggtagtttc acaactccct tttgtgtagg gggtttcggt   4020
tgtttctttta gaatctgctt cgtatgcact accgaccaca cccgaggggt atacagaggg   4080
cggaagaccc gtagacggac tgtaggtgcc acgtcgacca ctgtgtcgaa tacgggatac   4140
cgacggagaa tctggtacag gccctttgg cgcctgcgga cccgagggtc ctggacgact   4200
tgaccacata cgtctaacgg ttcccctact cgatggacct cctacacgcc gagcatgtgt   4260
ccctgaaccg gcgagccttg cacgaccagt tctcagggtt ggtacagttt taatgtctga   4320
agcccgaccg agccgacgac ctgtaactgc tctgtctcat ggtacgtcta cccccgttcc   4380
acgggtagtt cacctaccgc gacctcaggt aagaggcggc cgccaagtgg gtggtctcac   4440
tacacacctc aataccacac tgacacaccc tcgactactg aaaacccgg tttggaatgc   4500
taccctaggg tcgggccctc tagggactgg acgacctttt cccctcgcc gacggggtcg   4560
gggggtagac gtggtaacta cagatgtact agtaccagtt tacaacctac taactgagac   4620
ttacagccgg ttctaaggcc ctcaaccaca gacttaagag ggcgtaccgg tccctggggg   4680
tcgcgaaaca ccagtaggtc ttactcctga acccgggtcg gtcagggaac ctgtcgtgga   4740
agatggcgag tgacgacctc ctgctactgt acccctgga ccacctacga ctcctcatag   4800
accatggggt cgtcccgaag aagacaggtc tgggacgggg cccgcgaccc ccgtaccagg   4860
tggtgtccgt ggcgtcgagt agatggtcct caccgccacc cctggactgt gatcccgacc   4920
tcggagagct tctcctccgg gggtccagag gtgaccgtgg gaggcttccc cgaccgaggc   4980
tacataaact accactggac ccttaccccc gtcggttccc cgacgtttcg gagggtgtg   5040
tactgggggtc gggagatgtc gccatgtcac tcctgggtg tcatgggac gggagactct   5100
gactaccgat gcaacggggg gactggacgt cggggtcgg acttatacac ttggtcggtc   5160
tacaagccgg ggtcggggga agcggggctc tcccgggaga cggacgacgg gctgacgac   5220
cacggtgaga cctttcccgg ttctgagaga ggggtccctt cttaccccag cagtttctgc   5280
aaaaacggaa accccacgg cacctcttgg ggctcatgaa ctgtggggtc cctcctcgac   5340
ggggagtcgg ggtgggagga ggacggaagt cgggtcggaa gctgttggag ataatgaccc   5400
tggtcctggg tggtctcgcc ccccgaggtg ggtcgtggaa gtttccctgt ggatgccgtc   5460
tcttgggtct catggaccca gacctgcacg gtcacacttg gtcttccggt tcaggcgtct   5520
tcgggactac acaggagtcc ctcgtcccctt ccgccggaga ctcgataagg tcttcatcac   5580
tcctccgaaa aaacctccgg atccgaaaac gttttttcgaa tagctatggc agctgagctc   5640
tcatgaagat ctcgccggcg cccgggtagc ggagactgtc gttgcagata ctggaggatt   5700
tcctggatct ccttccgtag gtttgcgact accctcccga ccttctaccg tcgggggcct   5760
gacccgtcta gaagttcgtc tggatgtcgt tcaagctgtg tttgagtgtg ttgctactgc   5820
gtgatgagtt cttgatgccc gacgagatga cgaagtcctt cctgtacctg ttccagctct   5880
gtaaggacgc gtagcacgtc acggcgagac acctcccgtc gacaccgaag atcgacgggc   5940
ccaccgtagg gacactgggg aggggtcacg gagaggaccg ggaccttcaa cggtgaggtc   6000
acgggtggtc ggaacaggat tatttttaatt caacgtagta aaacagactg atccacagga   6060
agatattata atacccccacc tccccccacc atacctcgtt ccccgggttc aacccttctg   6120
ttggacatcc cggacgcccc agataagccc ttggttcgac ctcacgtcac cgtgttagaa   6180
```

-continued

```
ccgagtgacg ttagaggcgg aggacccaag ttcgctaaga ggacggagtc ggagggctca   6240
acaaccctaa ggtccgtacg tactggtccg agtcgattaa aaacaaaaaa accatctctg   6300
ccccaaagtg gtataaccgg tccgaccaga ggttgaggat tagagtccac tagatgggtg   6360
gaaccggagg gtttaacgac cctaatgtcc gcacttggtg acgagggaag ggacaggaag   6420
actaaaattt tattgatatg gtcgtcctcc tgcaggtctg tgtcgtatcc gatggacggt   6480
accgggttgg ccaccctgta aactcaacga acgaaccgtg acaggagagt acgcaaccca   6540
ggtgagtcat ctacggacaa cttaatgcta gccacgtgta attaagtact ttaagcatta   6600
gtaccagtat cgacaaagga cacactttaa caataggcga gtgttaaggt gtgttgtatg   6660
ctcggccttc gtatttcaca tttcggaccc cacggattac tcactccatt gagtgtaatt   6720
aacgcaacgc gagtgacggg cgaaaggtca gccctttgga cagcacggtc gacctaatta   6780
cttagccggt tgcgcgcccc tctccgccaa acgcataacc cgcgagaagg cgaaggagcg   6840
agtgactgag cgacgcgagc cagcaagccg acgccgctcg ccatagtcga gtgagtttcc   6900
gccattatgc caataggtgt cttagtcccc tattgcgtcc tttcttgtac actcgttttc   6960
cggtcgtttt ccggtccttg gcatttttcc ggcgcaacga ccgcaaaaag gtatccgagg   7020
cggggggact gctcgtagtg tttttagctg cgagttcagt ctccaccgct ttgggctgtc   7080
ctgatatttc tatggtccgc aaagggggac cttcgaggga gcacgcgaga ggacaaggct   7140
gggacggcga atggcctatg gacaggcgga aagagggaag cccttcgcac cgcgaaagag   7200
ttacgagtgc gacatccata gagtcaagcc acatccagca agcgaggttc gacccgacac   7260
acgtgcttgg ggggcaagtc gggctggcga cgcggaatag gccattgata gcagaactca   7320
ggttgggcca ttctgtgctg aatagcggtg accgtcgtcg gtgaccattg tcctaatcgt   7380
ctcgctccat acatccgcca cgatgtctca agaacttcac caccggattg atgccgatgt   7440
gatcttcctg tcataaacca tagacgcgag acgacttcgg tcaatggaag cctttttctc   7500
aaccatcgag aactaggccg tttgtttggt ggcgaccatc gccaccaaaa aaacaaacgt   7560
tcgtcgtcta atgcgcgtct ttttttccta gagttcttct aggaaactag aaaagatgcc   7620
ccagactgcg agtcaccttg cttttgagtg caattcccta aaaccagtac tctaatagtt   7680
tttcctagaa gtggatctag gaaaatttaa tttttacttc aaaatttagt tagatttcat   7740
atatactcat ttgaaccaga ctgtcaatgg ttacgaatta gtcactccgt ggatagagtc   7800
gctagacaga taaagcaagt aggtatcaac ggactgaggg gcagcacatc tattgatgct   7860
atgccctccc gaatggtaga ccggggtcac gacgttacta tggcgctctg ggtgcgagtg   7920
gccgaggtct aaatagtcgt tatttggtcg gtcggccttc ccggctcgcg tcttcaccag   7980
gacgttgaaa taggcggagg taggtcagat aattaacaac ggcccttcga tctcattcat   8040
caagcggtca attatcaaac gcgttgcaac aacggtaacg acgaccgtag caccacagtg   8100
cgagcagcaa accataccga agtaagtcga ggccaagggt tgctagttcc gctcaatgta   8160
ctagggggta caacacgttt tttcgccaat cgaggaagcc aggaggctag caacagtctt   8220
cattcaaccg gcgtcacaat agtgagtacc aataccgtcg tgacgtatta agagaatgac   8280
agtacggtag gcattctacg aaaagacact gaccactcat gagttggttc agtaagactc   8340
ttatcacata cgccgctggc tcaacgagaa cgggccgcag tagtgcccta ttatggcgcg   8400
gtgtatcgtc ttgaaatttt cacgagtagt aaccttttgc aagaagcccc gcttttgaga   8460
gttcctagaa tggcgacaac tctaggtcaa gctacattgg gtgagcacgt gggttgacta   8520
gaagtcgtag aaaatgaaag tggtcgcaaa gacccactcg tttttgtcct tccgttttac   8580
```

-continued

```
ggcgtttttt cccttattcc cgctgtgcct ttacaactta tgagtatgag aaggaaaaag     8640
ttataataac ttcgtaaata gtcccaataa cagagtactc gcctatgtat aaacttacat     8700 aaatctttt  atttgtttat ccccaaggcg cgtgtaaagg ggcttttcac ggtggactgc     8760
agattctttg gtaataatag tactgtaatt ggatattttt atccgcatag tgctccggga     8820
aagcagaagt tcttatgacg gagcgcgcaa agccactact gccacttttg gagactgtgt     8880
acgtcgaggg cctctgccag tgtcgaacag acattcgcct acggccctcg tctgttcggg     8940
cagtcccgcg cagtcgccca caaccgccca cagcccgcg tcggtactgg gtcagtgcat       9000
cgctatcgcc tcaaccgaat tgatacgccg tagtctcgtc taacatgact ctcacgtggt     9060
atacgccaca ctttatggcg tgtctacgca ttcctcttt atggcgtagt ccgcggtaag      9120
cggtaagtcc gatgcgttga caaccottcc cgctagccac gcccggagaa gcgataatgc    9180
ggtcgaccgc ttccccccta cacgacgttc cgctaattca acccattgcg gtcccaaaag    9240
ggtcagtgct gcaacatttt gctgccggtc acgg                                9274
```

<210> SEQ ID NO 11
<211> LENGTH: 16
<212> TYPE: PRT
<213> ORGANISM: human

<400> SEQUENCE: 11

Cys Val Asp Leu Asp Asp Lys Gly Cys Pro Ala Glu Gln Arg Ala Ser
1               5                   10                  15

What is claimed is:

1. A method for the treatment of a tumor in a mammal, comprising the steps of (i) identifying said tumor as being characterized by overexpression of an ErbB2 receptor and as being a tumor that does not respond, or responds poorly, to treatment with an anti-ErbB antibody, and (ii) intravenously administering to the mammal a therapeutically effective amount of a conjugate of a humanized antibody huMab 4D5-8 covalently linked via a thioether linking group with a maytansinoid DM1 having the structure

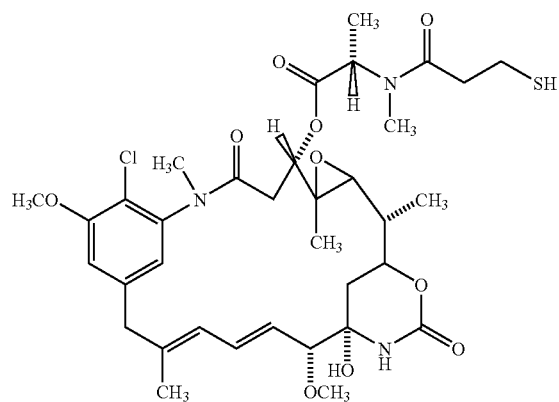

at a dose of between about 0.2 mg/kg and about 10 mg/kg (antibody-maytansinoid conjugate weight/body weight) and at a frequency of dosing selected from the group of dosing frequencies consisting of bolus, less than about 1 time per week, one time per week, two times per week, more than two times per week, and continuous infusion, whereby said tumor characterized by overexpression of an ErbB2 receptor and that does not respond, or responds poorly, to treatment with an anti-ErbB antibody, is treated.

2. A method for the treatment of a tumor in a human, comprising the steps of (i) identifying said tumor as being characterized by overexpression of an ErbB2 receptor and as being a tumor that does not respond, or responds poorly, to treatment with an anti-ErbB antibody, and (ii) intravenously administering to the human a therapeutically effective amount of a conjugate of a humanized antibody huMab 4D5-8 covalently linked via a thioether linking group with a maytansinoid DM1 having the structure

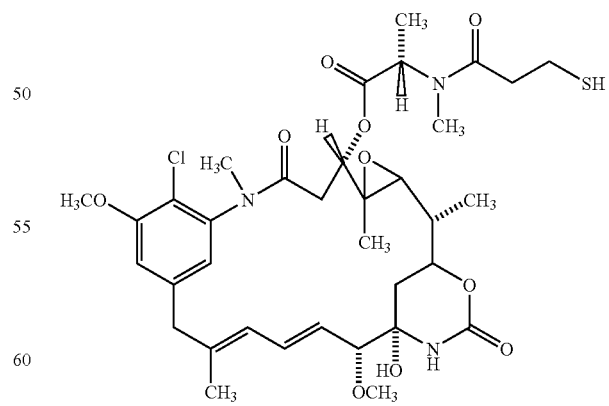

at a dose of between about 0.2 mg/kg and about 10 mg/kg (antibody-maytansinoid conjugate weight/body weight) and at a frequency of dosing selected from the group of dosing frequencies consisting of bolus, less than about 1 time per week, one time per week, two times per week, more than two times per week, and continuous infusion, whereby said tumor characterized by overexpression of an ErbB2 receptor and that does not respond, or responds poorly, to treatment with an anti-ErbB antibody, is treated.

3. The method of claim 1 wherein the dose is between about 0.5 mg/kg and about 5 mg/kg.

4. The method of claim 1 wherein the dose is between about 1 mg/kg and about 3 mg/kg.

5. The method of claim 1 wherein the dose is about 4 mg/kg.

6. The method of claim 1 method wherein dose is 2 mg/kg.

7. The method of claim 1 wherein the dosing frequency is less than about 1 time per week.

8. The method of claim 2 wherein the tumor is cancer.

9. The method of claim 8 wherein the cancer is selected from the group consisting of breast, ovarian, stomach, endometrial, salivary gland, lung, kidney, colon, colorectal, thyroid, pancreatic, prostate and bladder cancer.

10. The method of claim 9 wherein the cancer is breast cancer.

11. The method of claim 10 wherein the breast cancer overexpresses ErbB2 at a 2+ level or more.

12. The method of claim 11 wherein the breast cancer overexpresses ErbB2 at a 3+ level.

13. The method of claim 12 wherein the breast cancer is a metastatic breast cancer.

14. The method of claim 1 wherein the thioether linking group is succinimidyl-4-(N-maleimidomethyl)cyclohexane-1-carboxylate (SMCC).

15. The method of claim 1 wherein the conjugate comprises 1 to about 10 maytansinoid molecules per antibody molecule.

16. The method of claim 15 wherein the conjugate comprises from about 3 to about 5 maytansinoid molecules per antibody molecule.

17. The method of claim 1 further comprising the administration of a cytotoxic agent.

18. The method of claim 17 wherein the cytotoxic agent is selected from the group consisting of radioactive isotopes, chemotherapeutic agents, toxins, and fragments and/or variants thereof.

19. The method of claim 17 wherein the cytotoxic agent is a chemotherapeutic agent selected from the group consisting of alkylating agents, alkyl sulfonates, aziridines, ethylenimines, methylamelamines, nitrogen mustards, nitrosureas, antibiotics, anti-metabolites, folic acid analogues, purine analogs, pyrimidine analogs, androgens, anti-adrenals, folic acid replenishers, taxanes, platinum analogs, esperamicins, aromatase inhibiting 4(5)-imidazoles, anti-hormonal agents, anti-estrogens and anti-androgens.

20. The method of claim 17 wherein the chemotherapeutic agent is selected from the group consisting of thiotepa, cyclophosphamide, busulfan, improsulfan, piposulfan, benzodopa, carboquone, meturedopa, uredopa, altretamine, triethylenemelamine, trietylenephosphoramide, triethylenethiophosphaoramide, trimethylolomelamine, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, methotrexate, 5-fluorouracil (5-FU), denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, frolinic acid, aceglatone, aldophosphamide glycoside, aminolevulinic acid, amsacrine, bestrabucil, bisantrene, edatraxate, defofamine, demecolcine, diaziquone, elformithine, elliptinium acetate, etoglucid, gallium nitrate, hydroxyurea, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, tenuazonic acid, triaziquone, 2, 2',2'-trichlorotriethylamine, urethan, vindesine, dacarbazine, mannomustine, mitobronitol, mitolactol, pipobroman, gacytosine, arabinoside ("Ara-C"), paclitaxel, doxetaxel, chlorambucil, gemcitabine, 6-thioguanine, mercaptopurine, methotrexate, cisplatin, carboplatin, vinblastine, platinum, etoposide (VP-16), ifosfamide, mitomycin C, mitoxantrone, vincristine, vinorelbine, navelbine, novantrone, teniposide, daunomycin, aminopterin, xeloda, ibandronate, CPT-11, topoisomerase inhibitor RFS 2000, difluoromethylornithine (DMFO), retinoic acid, capecitabine, tamoxifen, raloxifene, aromatase inhibiting 4(5)-imidazoles, 4-hydroxytamoxifen, trioxifene, keoxifene, LY117018, onapristone, toremifene (Fareston), flutamide, nilutamide, bicalutamide, leuprolide, goserelin and pharmaceutically acceptable salts, acids or derivatives thereof.

21. The method of claim 1 wherein the conjugate is administered at a dose of between about 0.1 mg/kg and about 20 mg/kg body weight.

22. The method of claim 21 wherein the conjugate is administered at a dose of between about 0.5 mg/kg and about 5 mg/kg body weight.

23. The method of claim 1 wherein the conjugate is administered at a dose of between about 0.01 mg/kg and about 0.3 mg/kg.

24. The method of claim 1 wherein the conjugate is administered at a dose of between about 0.1 mg/kg and about 0.3 mg/kg.

25. The method of claim 1 wherein the conjugate comprises about 3 to 4 maytansinoid molecules per antibody molecule.

26. The method of claim 2 wherein the conjugate comprises about 3 to 4 maytansinoid molecules per antibody molecule.

27. The method of claim 2 wherein the thioether linking group is succinimidyl-4-(N-maleimidomethyl)cyclohexane-1-carboxylate (SMCC).

* * * * *

UNITED STATES PATENT AND TRADEMARK OFFICE
CERTIFICATE OF CORRECTION

PATENT NO. : 7,575,748 B1  
APPLICATION NO. : 11/488545  
DATED : August 18, 2009  
INVENTOR(S) : Erickson et al.

Page 1 of 1

It is certified that error appears in the above-identified patent and that said Letters Patent is hereby corrected as shown below:

On title page amend assignee:
Item (73) Assignee: Genentech, Inc. (South San Francisco, CA) <u>and ImmunoGen, Inc. (Cambridge, MA (US))</u>

Amend claim 20:
Column 83, line 52-53
20. The method of claim 17 wherein the <u>cytotoxic agent is a</u> chemotherapeutic agent [[is]] selected from the group consisting of thiotepa,
Column 83, line 56
ethylenemelamine, ~~trietylenephosphoramide~~ <u>triethylenephosphoramide,</u> triethyleneth
Column 83, line 57
~~iophosphaoramide~~ <u>iophosphoramide,</u> trimethylolomelamine, chlorambucil,

Delete claims 21, 22, 23, and 24

Signed and Sealed this
Twenty-eighth Day of December, 2010

David J. Kappos
*Director of the United States Patent and Trademark Office*